United States Patent
Dekel et al.

(10) Patent No.: US 10,465,004 B2
(45) Date of Patent: Nov. 5, 2019

(54) FRIZZLED RECEPTOR ANTIBODIES FOR TREATMENT OF CANCER

(71) Applicants: Tel HaShomer Medical Research Infrastructure and Services Ltd., Ramat-Gan (IL); Ramot at Tel-Aviv University Ltd., Tel-Aviv (IL)

(72) Inventors: Benjamin Dekel, Tel-Aviv (IL); Naomi Pode-Shakked, Tel-Aviv (IL); Orit Harai-Steinberg, RaAnana (IL); Michal Mark-Danieli, Moshav Zur Moshe (IL); Einav Vax, Rishon-LeZion (IL)

(73) Assignees: Tel HaShomer Medical Research Infrastructure and Services Ltd., Ramat-Gan (IL); Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/109,173

(22) PCT Filed: Jan. 1, 2015

(86) PCT No.: PCT/IL2015/050009
§ 371 (c)(1),
(2) Date: Jun. 30, 2016

(87) PCT Pub. No.: WO2015/101998
PCT Pub. Date: Jul. 9, 2015

(65) Prior Publication Data
US 2016/0326245 A1    Nov. 10, 2016

Related U.S. Application Data

(60) Provisional application No. 61/922,893, filed on Jan. 2, 2014.

(51) Int. Cl.
*C07K 16/30* (2006.01)
*C07K 16/28* (2006.01)
*A61K 39/00* (2006.01)

(52) U.S. Cl.
CPC .............. *C07K 16/28* (2013.01); *C07K 16/30* (2013.01); *C07K 16/3038* (2013.01); *A61K 2039/505* (2013.01); *C07K 2317/24* (2013.01); *C07K 2317/34* (2013.01); *C07K 2317/73* (2013.01)

(58) Field of Classification Search
CPC ................................ C07K 16/28; C07K 16/30
USPC ........................................................ 424/133.1
See application file for complete search history.

(56) References Cited

U.S. PATENT DOCUMENTS

2010/0104574 A1*  4/2010  Gurney .................. A61K 31/00
424/139.1

FOREIGN PATENT DOCUMENTS

| JP | 2012-503990 | 2/2012 |
|---|---|---|
| WO | WO 2006/036179 | 4/2006 |
| WO | WO 2007/053577 | 5/2007 |
| WO | WO 2007053577 | 5/2007 |
| WO | WO 2010/037041 | 4/2010 |
| WO | WO 2011/004379 | 1/2011 |
| WO | WO 2011004379 | 1/2011 |
| WO | WO 2015/101998 | 7/2015 |

OTHER PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
International Search report for PCT/IL2015/050009 dated Apr. 16, 2015.
Pode-Shakked N, et al Resistance or sensitivity of Wilms' tumor to anti-FZD7 antibody highlights the Wnt pathway as a possible therapeutic target, *Oncogene* (2011) 30, 1664-1680; doi:10.1038/onc.2010.549; published online Jan. 17, 2011.
Pode-Shakked N, et al Developmental tumourigenesis: NCAM as a putative marker for the malignant renal stem/progenitor cell population, *J. Cell. Mol. Med.* vol. 13, No. 8B, 2009 pp. 1792-1808.
Communication Pursuant to Rule 164(1) EPC [Supplementary Partial European Search Report and the Provisional Opinion] dated Jul. 19, 2017 From the European Patent Office Re. Application No. 15733130.7. (14 Pages).
Aviva Systems Biology "ARP41251 P050—FZD7 Antibody—C-Terminal Region (ARP41251_P050)", Aviva Systems Biology, XP055388620, Product Datasheet, 2 P., Jul. 6, 2017.
Ueno et al. "Frizzled-7 as a Potential Therapeutic Target in Colorectal Cancer", Neoplasia, XP002612805, 10(7): 697-705, Jul. 2008. p. 699, r-h Col., Lines 3-4.
International Preliminary Report on Patentability dated Jul. 14, 2016 From the International Bureau of WIPO Re. Application No. PCT/IL2015/050009.
International Search Report and the Written Opinion dated Apr. 16, 2015 From the International Searching Authority Re. Application No. PCT/IL2015/050009.
Pode-Shakked et al. "Developmental Tumourigenesis: NCAM as a Putative Marker for the Malignant Renal Stem/Progenitor Cell Population", Journal of Cellular and Molecular Medicine, XP002581529, 13(8B): 1792-1808, Published Online Dec. 16, 2008. Abstract, p. 1800.
Pode-Shakked et al. "Resistance or Sensitivity of Wilms' Tumor to Anti-FZD7 Antibody Highlights the Wnt Pathway as a Possible Therapeutic Target", Oncogene, 30(14): 1664-1680, Published Online Jan. 17, 2011. p. 1665, Left Col., 2nd Para—p. 1667, Right Col., 1st Para, Fig.1.
Notification of Grounds for Rejection dated Oct. 30, 2018 From the Japan Patent Office Re. Application No. 2016-544451 and Its Translation Into English. (10 Pages).
King et al. "Frizzled7 as an Emerging Target for Cancer Therapy", Cellular Signaling, 24(4): 846-851, Published Online Dec. 13, 2011.

* cited by examiner

*Primary Examiner* — Yan Xiao

(57) ABSTRACT

The invention provides antibodies or an antigen-binding portion thereof, which recognize the human Frizzled 7 receptor. Further, the invention provides methods of using these antibodies for the treatment cancer in a subject.

12 Claims, 23 Drawing Sheets
Specification includes a Sequence Listing.

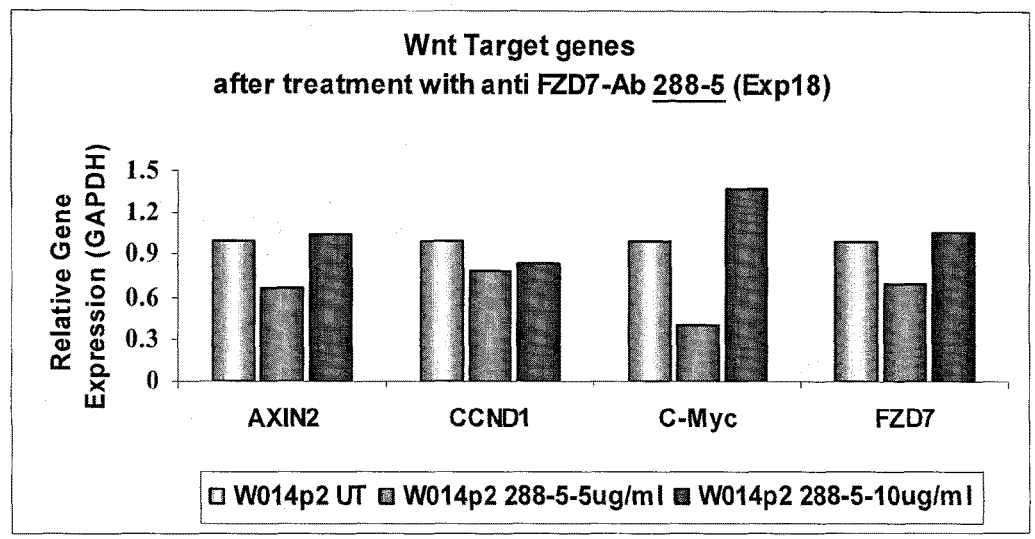
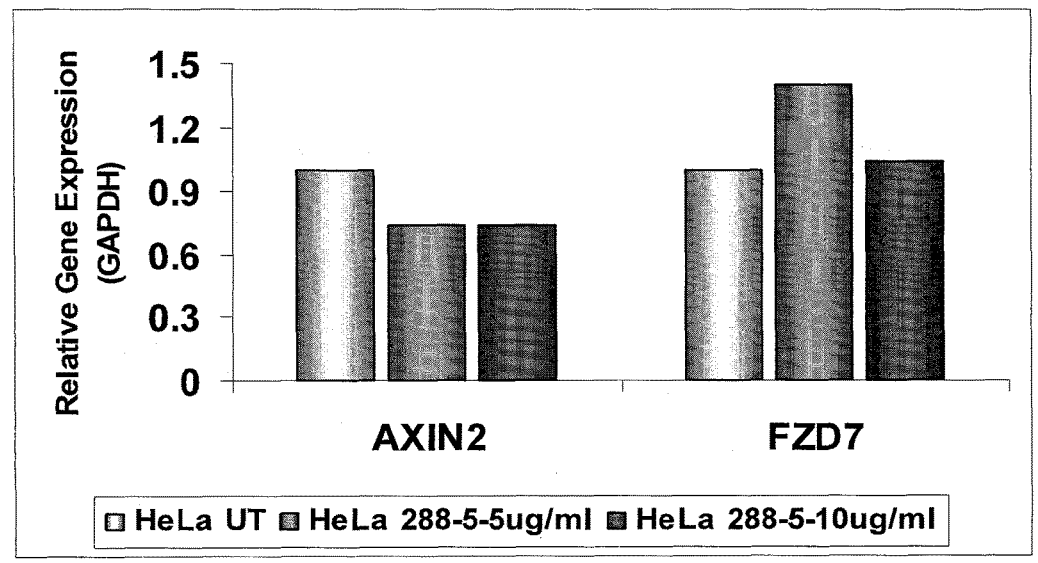
Figure 7B (cont.)

FRIZZLED RECEPTOR ANTIBODIES FOR TREATMENT OF CANCER

CROSS-REFERENCE TO RELATED APPLICATIONS

This application is a National Phase Application of PCT International Application No. PCT/IL2015/050009, International Filing Date Jan. 1, 2015, claiming priority to and benefit of U.S. Provisional Application Ser. No. 61/922,893 filed on Jan. 2, 2014, the contents of which are herein incorporated by reference in their entireties.

FIELD OF THE INVENTION

The present invention relates to compositions for treatment of diseases such as cancer. Specifically, the invention relates to antibodies that bind to human frizzled receptors, as well as to methods of using the antibodies or for the treatment cancer.

BACKGROUND OF THE INVENTION

It is becoming clear that many, if not most, malignancies arise from a population of cells that exclusively maintain the ability to self-renew and sustain the tumor via the expression of tumor progenitor genes. These "cancer stem cells" are often biologically distinct from the differentiated cancer cells that comprise most of the tumor bulk. Because cancer stem cells are believed to be primarily responsible for tumor initiation as well as resistance to chemo- and radiotherapy, their persistence may account for relapsing disease in cancer patients.

Wilms' tumor, a type of kidney cancer or nephroblastoma is one of the most common solid tumors of childhood, occurring in 1 in 10,000 children and accounting for 8% of childhood cancers. With improved multimodality therapy, WT survival rates have risen over the last 40 years to 85%-90%; however, for those whose disease relapses or metastasizes, even intensive salvage regimens result in subsequent survival closer to 50%. Moreover, survivors are at increased risk for a broad spectrum of adverse outcomes caused by chemotherapy and radiation therapy, such as late mortality and secondary cancers.

Wilms tumor is believed to result from malignant transformation of abnormally persistent renal stem cells which retain embryonic differentiation potential. Indeed, recent molecular data obtained by microarrays demonstrate that Wilms' tumor and Wilms' tumor-stem like xenografts systematically overexpress nephric-progenitor genes corresponding to the earliest stages of normal metanephric kidney development connecting tumorigenesis and organogenesis in the kidney.

In addition to genes that specify the renal lineage, Wnt pathway-related molecules including β-catenin (CTNNB1), frizzled7 (FZD7) and frizzled2 (FZD2), are concomitantly induced in Wilms' tumor. In general, the binding of Wnt ligand to frizzled cell surface receptors normally leads to inhibition of a "destruction complex" consisting of APC/Axin/GSK-3β/Ckl/Dvl and other factors, with subsequent accumulation of dephosphorylated stabilized β-catenin, and transcription of its target genes. Interestingly, recent data have demonstrated an essential role for the Wnt-β-catenin signaling pathway in nephrogenesis. Also, a genomic screen of Wilms' tumor identified FZD7, a Wnt receptor, to be a biomarker of cancer stem cells in Wilms' tumor. Additionally, a striking link between β-catenin signaling and the development of Wilms tumor has been demonstrated.

In recent years the involvement of the Wnt pathway has been shown in various other tumors (e.g. colon, breast) and in the self-renewal mechanism of stem cells. Unregulated activation of the Wnt can alter the developmental fate of tumor cells to maintain them in an undifferentiated and proliferative state. Thus carcinogenesis can proceed in the context of altered homeostatic mechanisms controlling normal development and tissue repair by stem cells.

Secreted Wnt ligands activate a receptor complex consisting of a Fzd receptor family member and low-density lipoprotein (LDL) receptor-related protein 5 or 6 (LPR5/6). The Fzd receptors are seven transmembrane domain receptors of the G-protein coupled receptor (GPCR) superfamily and contain a large extracellular N-terminal ligand binding domain with 10 conserved cysteines, known as the cysteine rich domain. There are ten known human FZD receptors: FZD1-10. Different Fzd cysteine rich domains have different binding affinities for specific Wnts. Fat receptors have been grouped into those that activate the canonical β-catenin pathway and those that activate noncanonical pathways.

To form the receptor complex that binds the FZD ligands, FZD receptors interact with LRP5/6, single pass transmembrane proteins. The canonical Wnt signaling pathway activated upon receptor binding is mediated by the cytoplasmic protein Dishevelled (Dsh) interacting directly with the Fzd receptor and results in the cytoplasmic stabilization and accumulation of β-catenin. In the absence of a Wnt signal, β-catenin is localized to a cytoplasmic destruction complex that includes the tumor suppressor proteins adenomatous polyposis coli (APC) and Axin. Activation of Dsh results in the dissociation of the destruction complex.

In addition to the canonical signaling pathway, Wnt ligands also activate β-catenin—independent pathways (i.e. non-canonical Wnt signaling). Non-canonical Wnt signaling has been implicated in the process of gastrulation. Antagonism is often reported between the canonical and non-canonical pathways, and some evidence indicates that non-canonical signaling can suppress cancer formation. Thus, in certain contexts, Fzd receptors act as negative regulators of the canonical Wnt signaling pathway. For example, FZD6 represses Wnt canonical signaling when co-expressed with FZD1.

The canonical Wnt signaling pathway also plays a central role in the maintenance of stem cell populations in the small intestine and colon, and the inappropriate activation of this pathway plays a prominent role in colorectal cancers; colorectal cancer is most commonly initiated by activating mutations in the Wnt signaling cascade. Approximately 5-10% of all colorectal cancers are hereditary with one of the main forms being familial adenomatous polyposis (FAP), an autosomal dominant disease in which about 80% of affected individuals contain a germline mutation in the adenomatous polyposis coli (APC) gene. Mutations have also been identified in other Wnt pathway components including Axin and β-catenin.

In human breast cancer, β-catenin accumulation implicates activated Wnt signaling in over 50% of carcinomas, and though specific mutations have not been identified, upregulation of Frizzled receptor expression has been observed.

Thus, there remains a need to identify molecules that may halt the inappropriate activation of the Wnt signaling pathway in cancers, including but not limited to colorectal cancer, melanomas and breast cancer. The present invention addresses this need by providing an antibody specific to the FZD7 receptor.

SUMMARY OF THE INVENTION

In one embodiment, the invention provides an isolated antibody or antigen-binding portion thereof that binds specifically to a Frizzled7 receptor, wherein the antibody binds to the cytoplasmic portion and optionally, the transmembrane portion of said receptor. In another embodiment the antibody may be selected from the group consisting of:
  a) the antibody produced by the hybridoma cell line 288-1;
  b) the antibody produced by the hybridoma cell line 288-2;
  c) the antibody produced by the hybridoma cell line 288-3; and
  d) the antibody produced by the hybridoma cell line 288-5.

In another embodiment, the invention provides an isolated antibody or antigen-binding portion thereof that binds to a sequence comprising at least a 5 amino acid (AA) portion of SEQ ID NO:1, wherein said portion of SEQ ID NO:1 is present on a Frizzled receptor. In another embodiment the antibody may be selected from the group consisting of:
  a) the antibody produced by the hybridoma cell line 288-1;
  b) the antibody produced by the hybridoma cell line 288-2;
  c) the antibody produced by the hybridoma cell line 288-3; and
  d) the antibody produced by the hybridoma cell line 288-5.

In another embodiment, the invention provides an isolated antibody or antigen-binding portion thereof that binds to a sequence comprising at least a 5 AA portion of SEQ ID NO:2, wherein said portion of SEQ ID NO:2 is present on a Frizzled receptor.

In another embodiment, the invention provides an isolated antibody or antigen-binding portion thereof that binds to a sequence comprising at least a 5 AA portion of SEQ ID NO:3, wherein said portion of SEQ ID NO:3 is present on a Frizzled receptor.

In another embodiment, the invention provides an isolated antibody or antigen-binding portion thereof that binds to a sequence comprising at least a 5 AA portion of SEQ ID NO:4, wherein said portion of SEQ ID NO:4 is present on a Frizzled receptor. In another embodiment the antibody may be selected from the group consisting of:
  a) the antibody produced by the hybridoma cell line 289-6;
  b) the antibody produced by the hybridoma cell line 289-12; and
  c) the antibody produced by the hybridoma cell line 289-18.

In another embodiment, the invention provides a method for treating a tumor in a subject. The method comprises the step of administering a therapeutically effective dose of an isolated antibody or antigen-binding portion thereof that binds to a Frizzled7 receptor, wherein the antibody binds to the cytoplasmic portion and optionally, the transmembrane portion of the receptor. In another embodiment the antibody used in this method may be selected from the group consisting of:
  a) the antibody produced by the hybridoma cell line 288-1;
  b) the antibody produced by the hybridoma cell line 288-2;
  c) the antibody produced by the hybridoma cell line 288-3; and
  d) the antibody produced by the hybridoma cell line 288-5.

In another embodiment, the invention provides a method for treating a tumor in a subject. The method comprises the step of administering a therapeutically effective dose of an isolated antibody or antigen-binding portion thereof to a subject, wherein said isolated antibody binds to a sequence comprising at least a 5 AA portion of SEQ ID NO: 1, wherein said portion of SEQ ID NO:1 is present on a Frizzled receptor, and wherein said tumor has elevated expression or activity of Frizzled receptors. In another embodiment the antibody used in this method may be selected from the group consisting of:
  a) the antibody produced by the hybridoma cell line 288-1;
  b) the antibody produced by the hybridoma cell line 288-2;
  c) the antibody produced by the hybridoma cell line 288-3; and
  d) the antibody produced by the hybridoma cell line 288-5.

In another embodiment, the invention provides a method for treating a tumor in a subject. The method comprises the step of administering a therapeutically effective dose of an isolated antibody or antigen-binding portion thereof to a subject, wherein said isolated antibody binds to a sequence comprising at least a 5 AA portion of SEQ ID NO: 2, wherein said portion of SEQ ID NO:1 is present on a Frizzled receptor, and wherein said tumor has elevated expression or activity of Frizzled receptors.

In another embodiment, the invention provides a method for treating a tumor in a subject. The method comprises the step of administering a therapeutically effective dose of an isolated antibody or antigen-binding portion thereof to a subject, wherein said isolated antibody binds to a sequence comprising at least a 5 AA portion of SEQ ID NO: 3, wherein said portion of SEQ ID NO:3 is present on a Frizzled receptor, and wherein said tumor has elevated expression or activity of Frizzled receptors.

In another embodiment, the invention provides a method for treating a tumor in a subject. The method comprises the step of administering a therapeutically effective dose of an isolated antibody or antigen-binding portion thereof to a subject, wherein said isolated antibody binds to a sequence comprising at least a 5 AA portion of SEQ ID NO: 4, wherein said portion of SEQ ID NO:4 is present on a Frizzled receptor, and wherein said tumor has elevated expression or activity of Frizzled receptors. In another embodiment the antibody used in this method may be selected from the group consisting of:
  a) the antibody produced by the hybridoma cell line 289-6;
  b) the antibody produced by the hybridoma cell line 289-12; and
  c) the antibody produced by the hybridoma cell line 289-18.

In another embodiment, the invention provides a method of detecting a tumor in a subject. The method comprises the steps of obtaining a biological sample from the subject; and testing the biological sample for Frizzled7 by an isolated antibody or antigen-binding portion thereof that binds to a Frizzled7 receptor, wherein the antibody binds to the cytoplasmic portion and optionally, the transmembrane portion of said receptor. In another embodiment the antibody used in this method may be selected from the group consisting of:
a) the antibody produced by the hybridoma cell line 288-1;
b) the antibody produced by the hybridoma cell line 288-2;
c) the antibody produced by the hybridoma cell line 288-3; and
d) the antibody produced by the hybridoma cell line 288-5.

In another embodiment, the invention provides a method of detecting a tumor in a subject. The method comprises the steps of obtaining a biological sample from the subject; and testing the biological sample for a Frizzled receptor by. an isolated antibody or antigen-binding portion thereof that binds to a sequence comprising at least a 5 AA portion of SEQ ID NO:1, wherein said portion of SEQ ID NO:1 is present on the Frizzled receptor. In another embodiment the antibody used in this method may be selected from the group consisting of:
a) the antibody produced by the hybridoma cell line 288-1;
b) the antibody produced by the hybridoma cell line 288-2;
c) the antibody produced by the hybridoma cell line 288-3; and
d) the antibody produced by the hybridoma cell line 288-5.

In another embodiment, the invention provides a method of detecting a tumor in a subject. The method comprises the steps of obtaining a biological sample from the subject; and testing the biological sample for a Frizzled receptor by. an isolated antibody or antigen-binding portion thereof that binds to a sequence comprising at least a 5 AA portion of SEQ ID NO:2, wherein said portion of SEQ ID NO:2 is present on the Frizzled receptor.

In another embodiment, the invention provides a method of detecting a tumor in a subject. The method comprises the steps of obtaining a biological sample from the subject; and testing the biological sample for a Frizzled receptor by. an isolated antibody or antigen-binding portion thereof that binds to a sequence comprising at least a 5 AA portion of SEQ ID NO:3, wherein said portion of SEQ ID NO:3 is present on the Frizzled receptor.

In another embodiment, the invention provides a method of detecting a tumor in a subject. The method comprises the steps of obtaining a biological sample from the subject; and testing the biological sample for a Frizzled receptor by. an isolated antibody or antigen-binding portion thereof that binds to a sequence comprising at least a 5 AA portion of SEQ ID NO:4, wherein said portion of SEQ ID NO:4 is present on the Frizzled receptor. In another embodiment the antibody used in this method may be selected from the group consisting of:
a) the antibody produced by the hybridoma cell line 289-6;
b) the antibody produced by the hybridoma cell line 289-12; and
c) the antibody produced by the hybridoma cell line 289-18.

In some embodiments, methods of this invention are directed to a Wilm's tumor, a colorectal tumor, a colon cancer, a tumor comprising melanoma cells, or a breast tumor, or any combination thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

SK-MEL-28 and SK-MEL-28 melanoma cells were seeded in 96-well plates and were incubated with antibodies for 48 hours and then were assayed for viability by trypan blue. Absolute cell counts of live cells are shown.

Figure 4A:
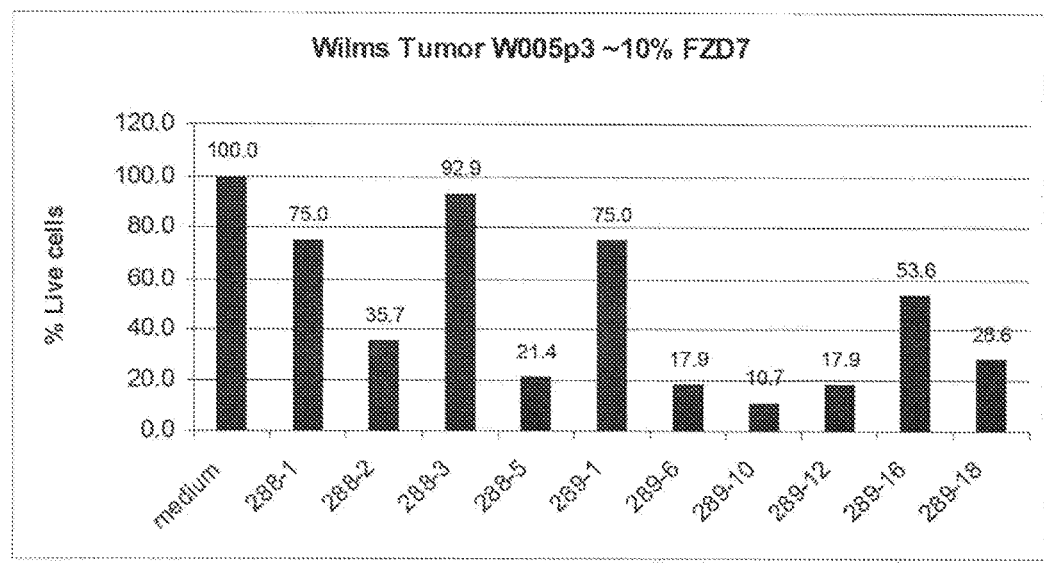
FIG. 4A shows killing of primary tumor malignant cells by FZD7-specific monoclonal antibodies. Primary tumor was Wilms' tumor and antibodies were FZD7-specific monoclonal antibodies produced by hybridoma clones generated with selected epitopes. Numbers indicate the hybridoma clone from which an antibody was taken (for example, 288-1 indicates a monoclonal antibody generated by hybridoma clone 288-1). Wilms' Tumor cells (W005) were seeded in 96-well plates and were incubated with antibodies for 48 hours and then were assayed for viability by trypan blue. Percent of live cells from total cells is indicated.
Figure 4B:
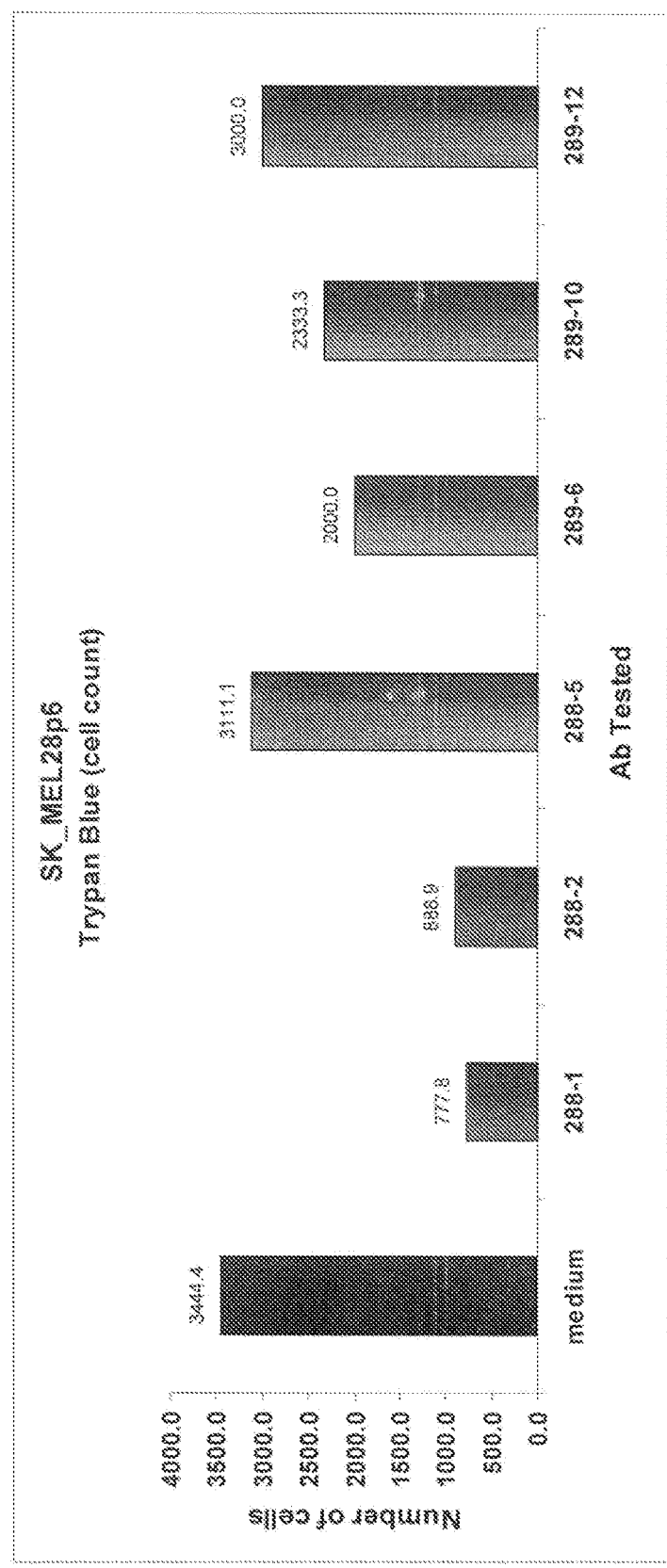
FIG. 4B shows killing of SK-MEL-28 and SK-MEL-28 melanoma cells by FZD7-specific monoclonal antibodies produced by hybridoma clones generated with selected epitopes. Numbers indicate the hybridoma clone from which an antibody was taken (for example, 288-1 indicates a monoclonal antibody generated by hybridoma clone 288-1).
Figure 4B:
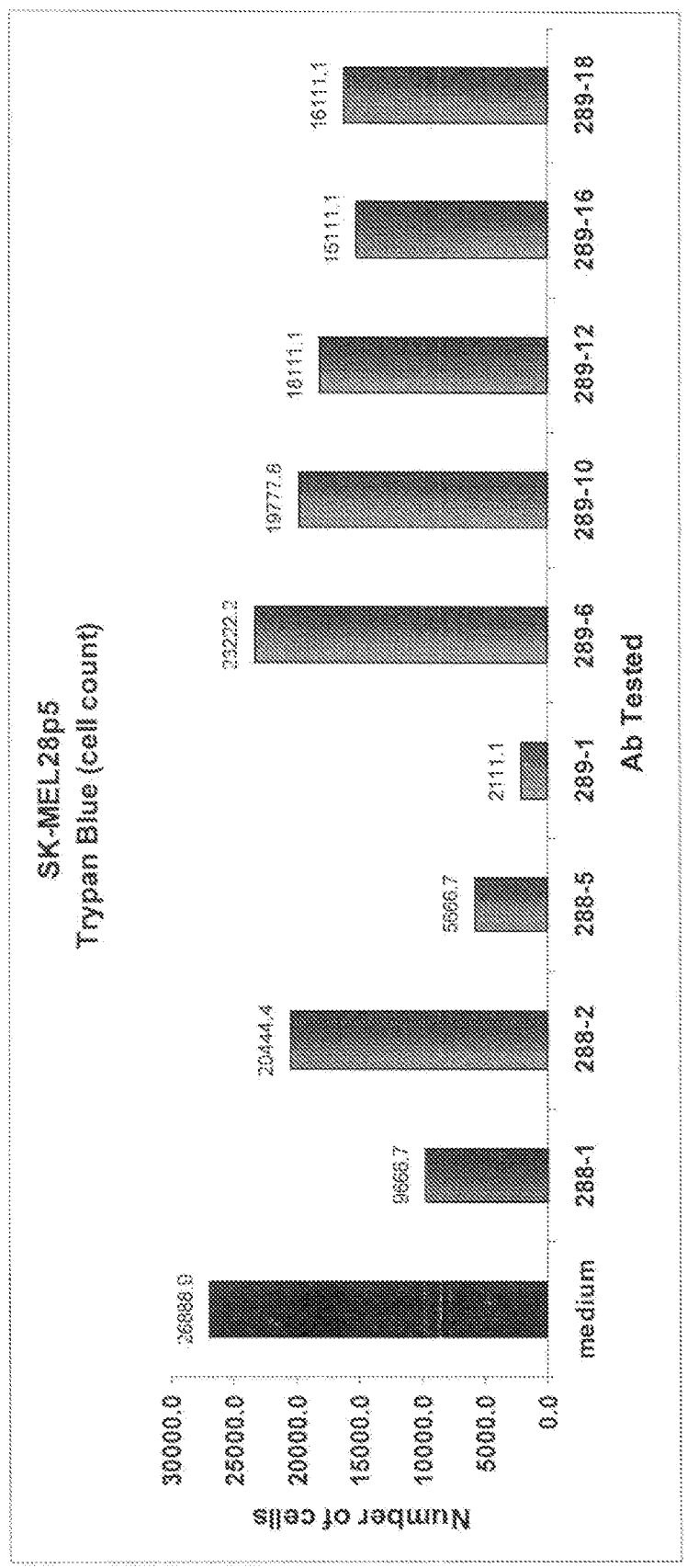
Figure 4C:
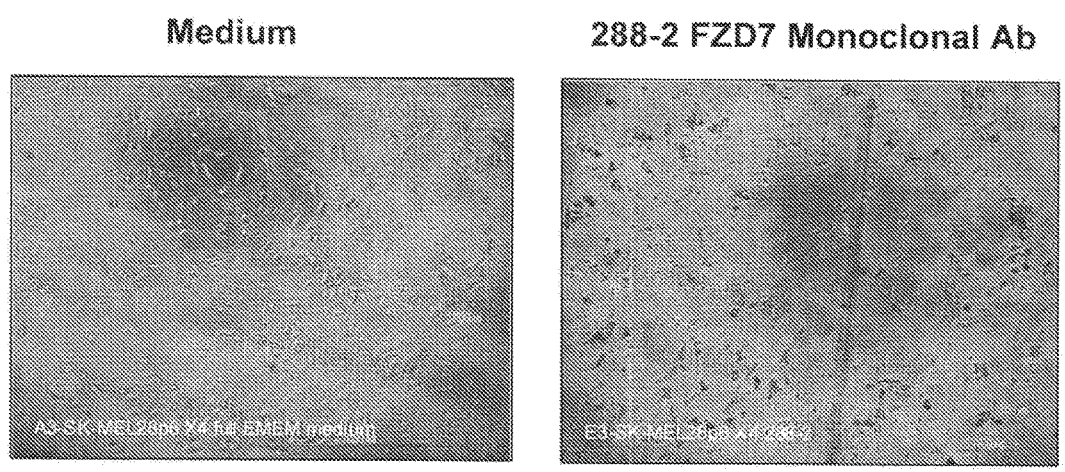

FIG. 4C shows representative micro-images of SK-MEL-28 cells after treatment with one of the monoclonal antibodies (clone 288-2, right image) or without antibody treatment (left). Cell death and is visible in treated cells (right).

Figure 5A:
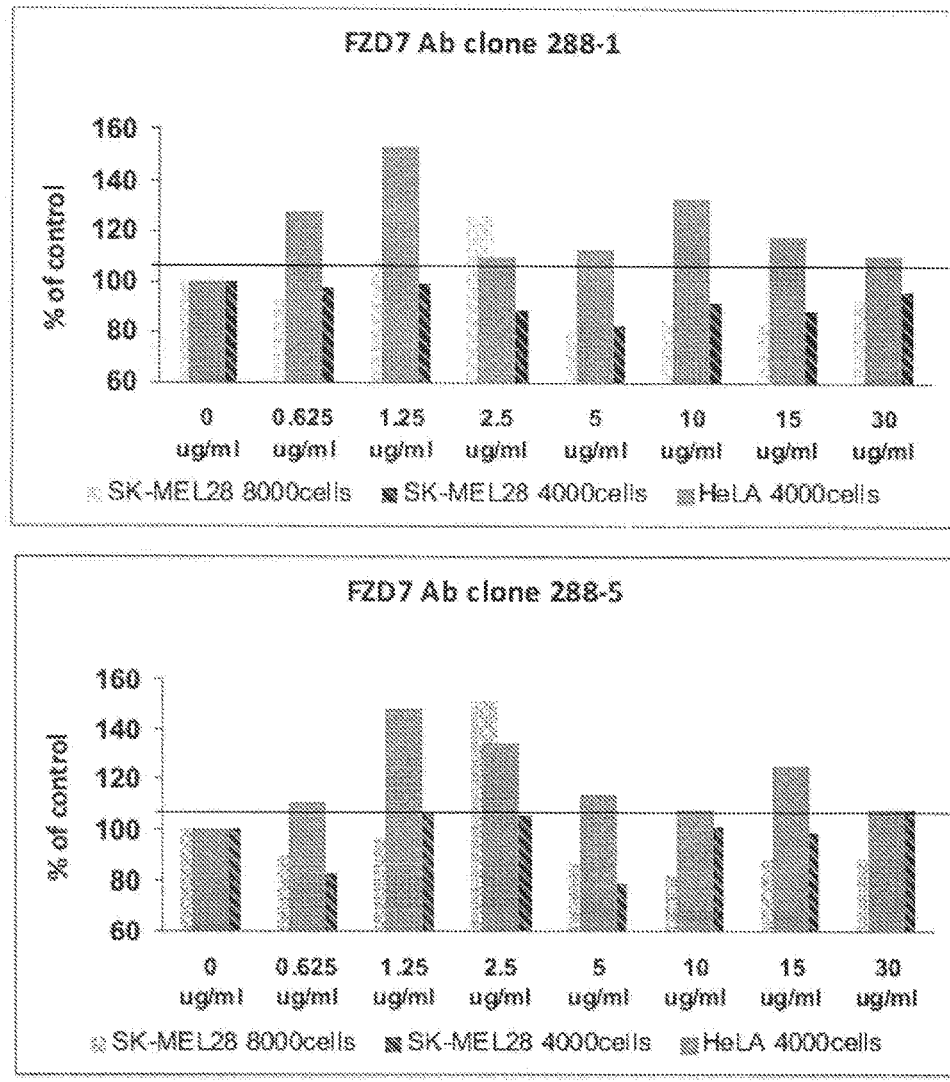

FIG. 5A shows the dose response in terms of inhibition of cell proliferation upon exposure to different concentrations of anti FZD7 monoclonal antibody produced in clones 288-1 (top) and 288-5 (bottom). The response of a high FZD7-expressing malignant tissue (SK-MEL28, melanoma cells) is compared with that of a low FZD7-expressing malignant tissue (HeLa, cervical cancer cells). Cells were exposed to antibody for 48 h and proliferation was assessed by the MTS assay and compared to cells not treated with antibody. Proliferation was inhibited in the presence of either FZD7 antibody in high FZD7 expressing cells but not in low expressing cells (HeLA). Optimal inhibition of proliferation was observed at an antibody concentration of about 5 ug/ml. Data shown is normalized to control untreated cells for each cell line.

Figure 5B:
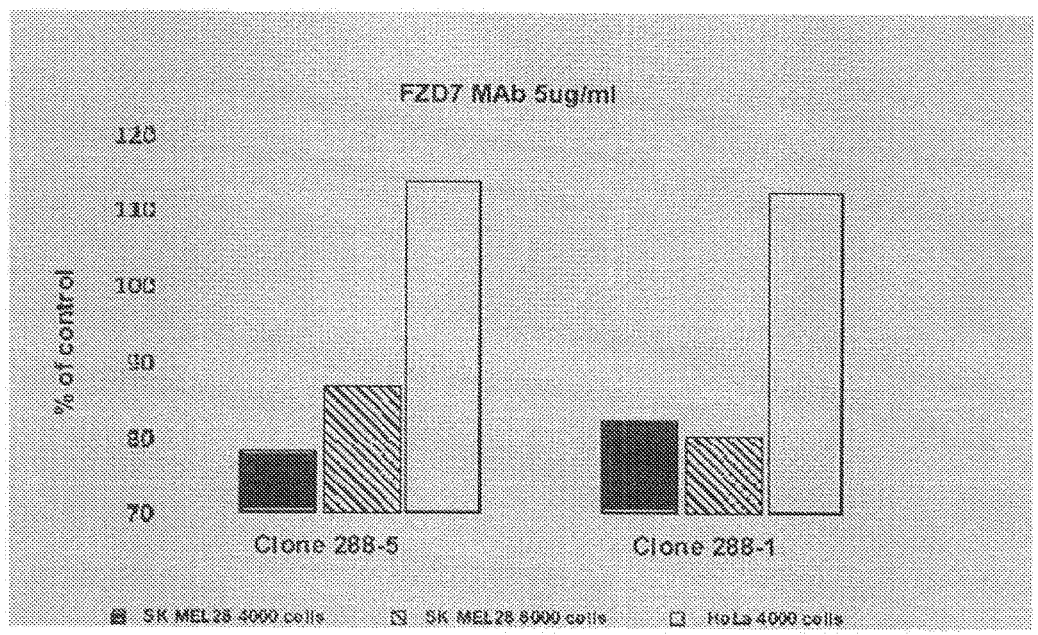

FIG. 5B shows the data from FIG. 5A in a way which highlights the effect the culturing density of SK-MEL28 melanoma cells has on the level of inhibition of proliferation by 5 ug/ml of the FZD7 monoclonal Ab produced by hybridoma clones 288-1 and 288-5. It is observed that at this Ab concentration, inhibition is greater when a 4000 cell/well density is employed in the case of 288-5 and similar in the case of 288-1.

Figure 6:
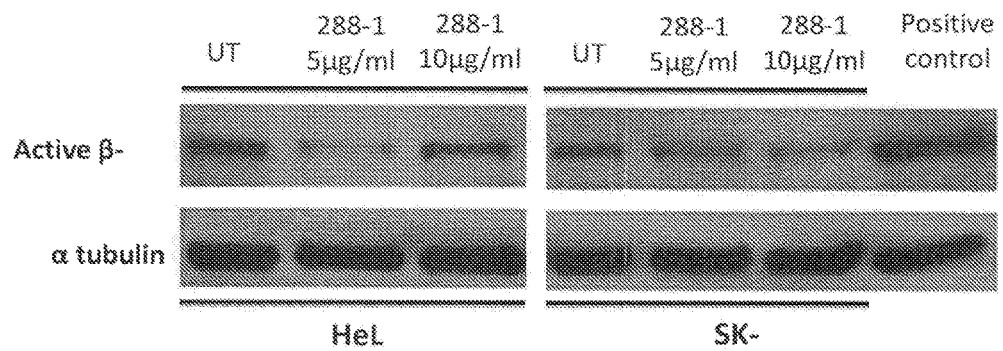

FIG. 6 shows Western blot analysis for active β-Catenin (Millipore 05665) in HeLa and SK-MEL28 cells after 48 h treatment with 288-1 Ab at the indicated concentration. β-Catenin inhibition by the 288-1 FZD7 mAb is demonstrated.

Figure 7A:
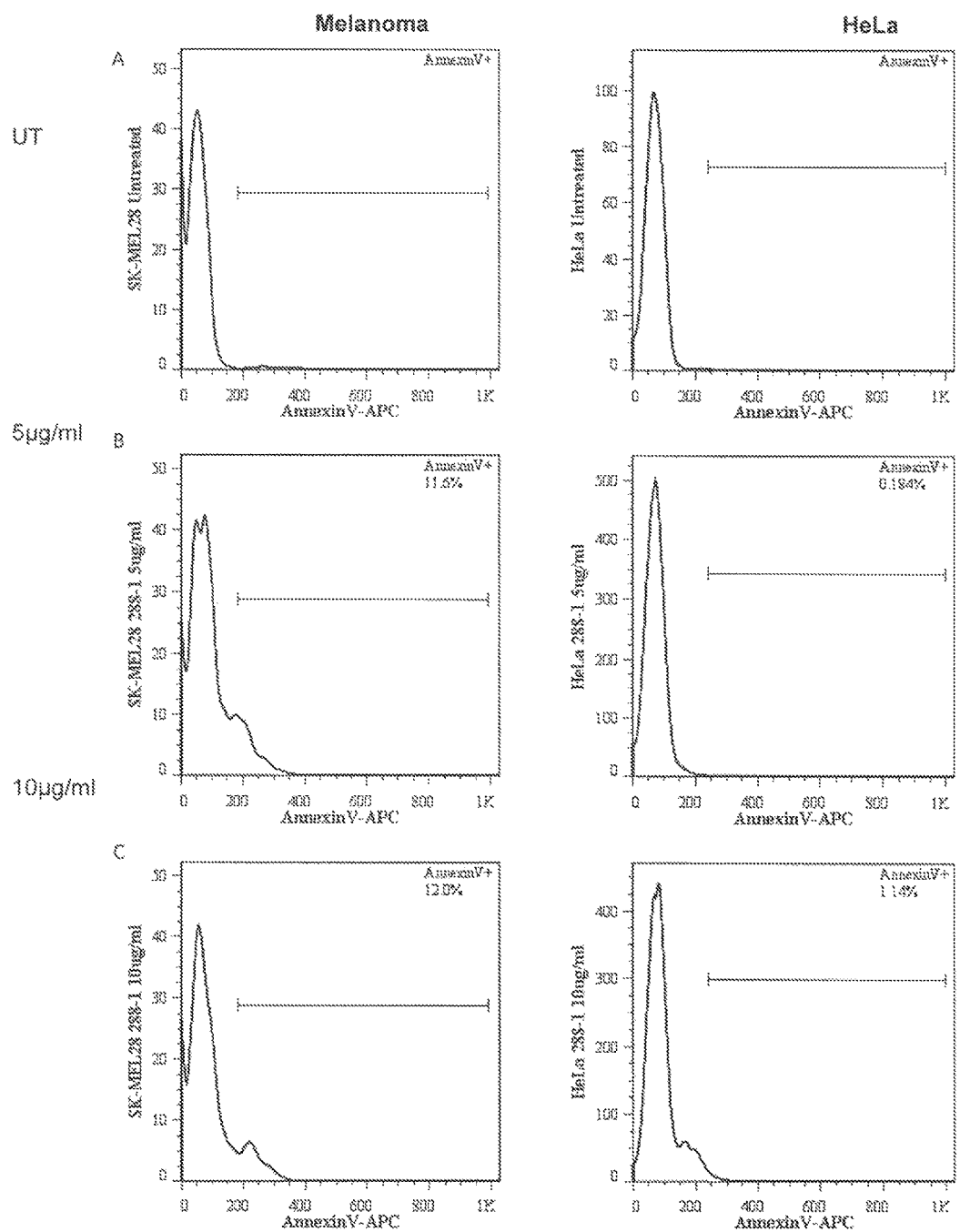

FIG. 7A shows apoptosis of malignant cells treated with antibodies of the invention. Specifically, Flow cytometry of APC conjugated Annexin V to Melanoma and HeLa cells is shown. Levels of Annexin staining are compared in the presence of the monoclonal antibody produced by hybridoma 288-1 at different concentrations or without antibody.

Figure 7B:
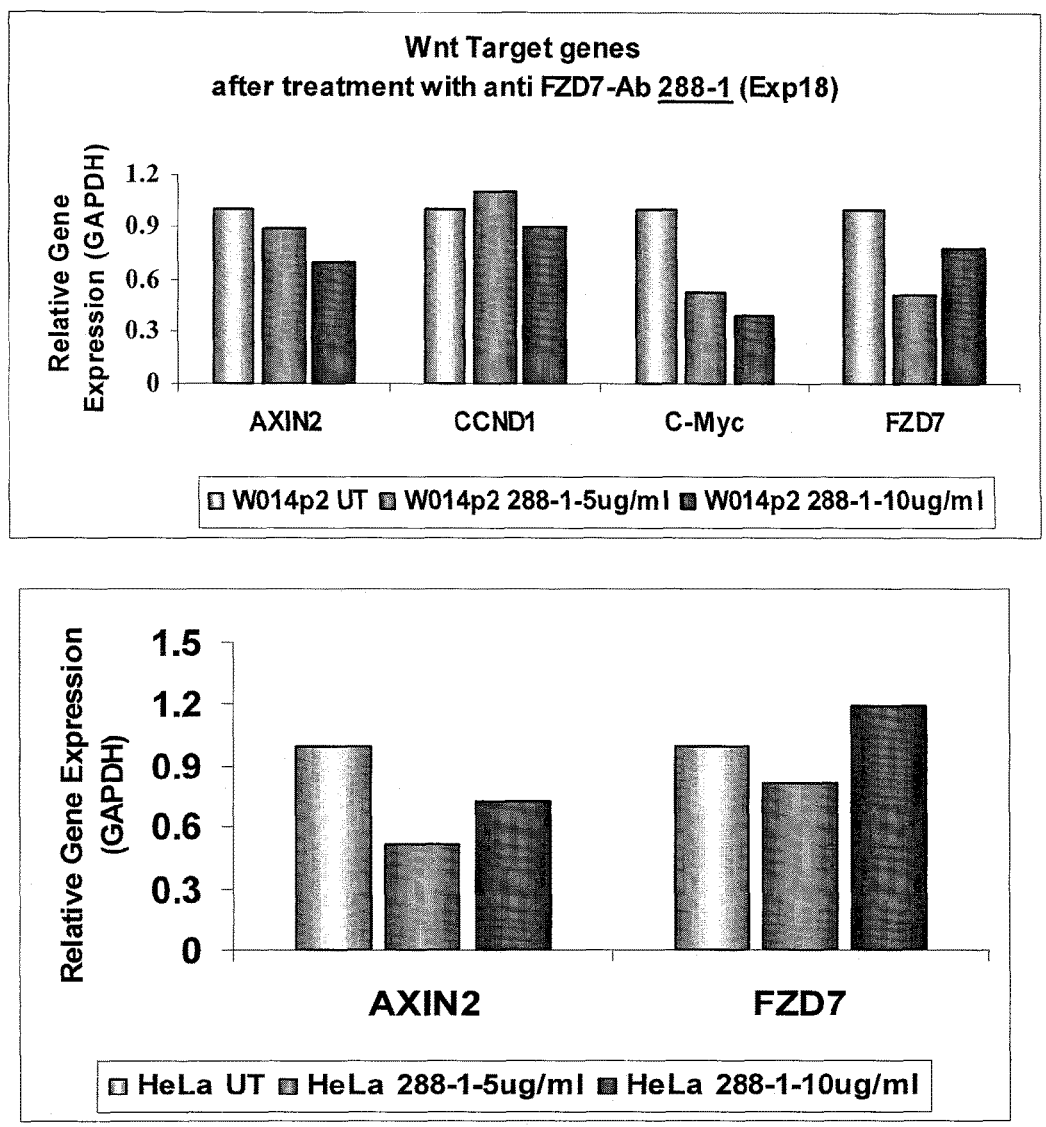

FIG. 7B shows Expression of WNT targeted genes using RQ PCR. Untreated and treated Wilms' tumor and HeLa cells.

Figure 8:
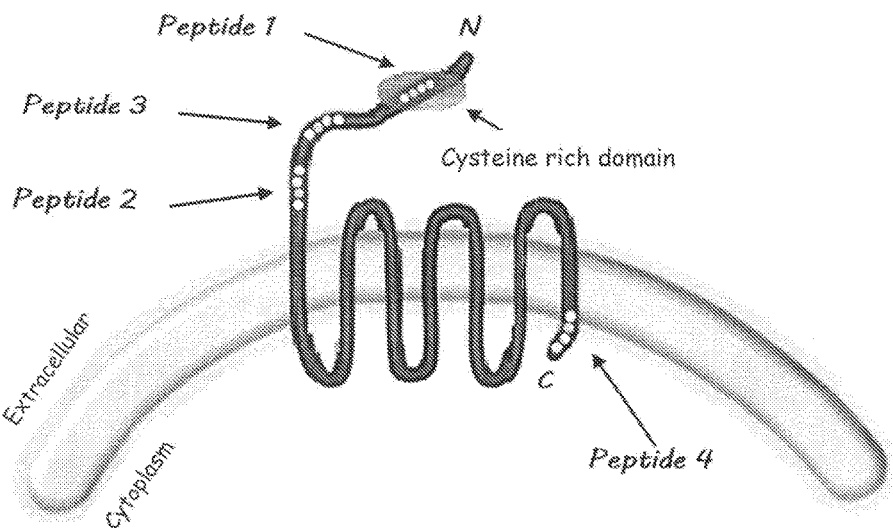

FIG. 8 illustrates the arrangement of the FZD7 polypeptide within the plasma membrane and identifies the locations of peptides 1-4.

Figure 9:
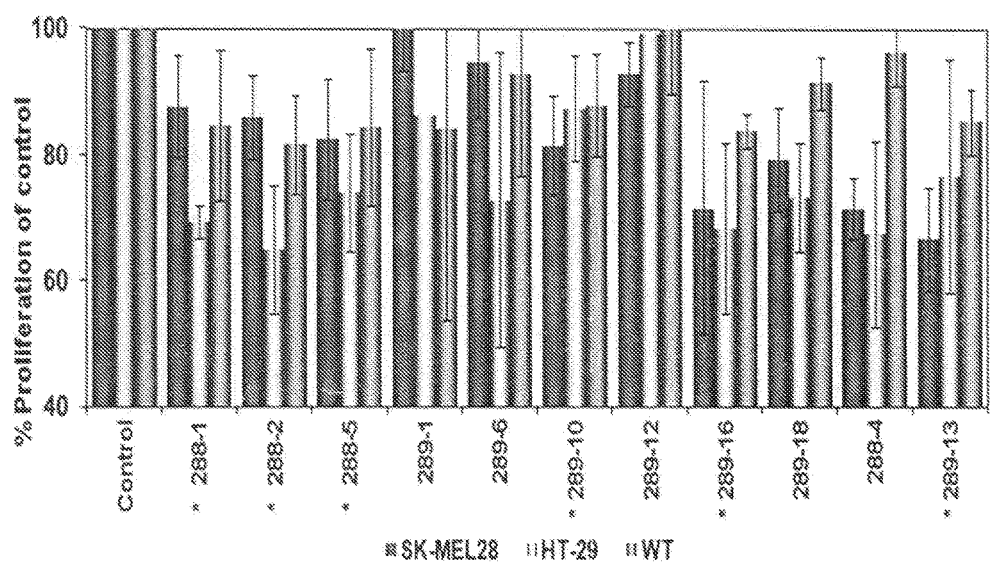

FIG. 9 presents data showing the inhibition of cell proliferation by FZD7 specific monoclonal antibodies secreted by hybridomas in relationship to percent proliferation of control.

Figure 10:
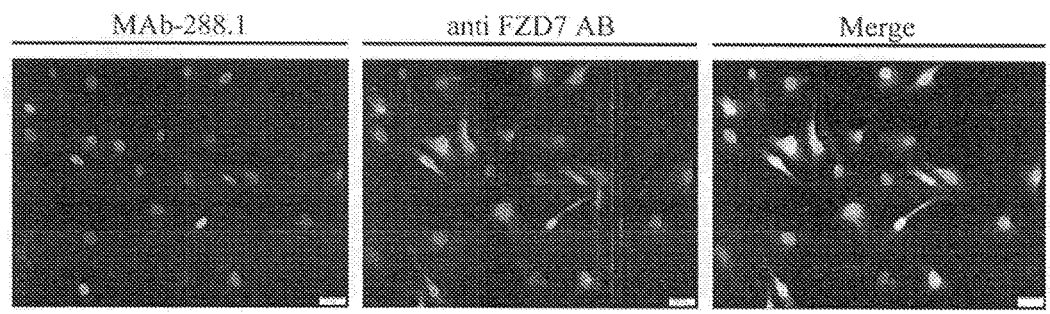

FIG. 10 presents a micrograph showing Anti FZD7 Ab288-1 double labeling with a commercial anti FZD7 antibody of SK-MEL28 cells.

Figure 11:
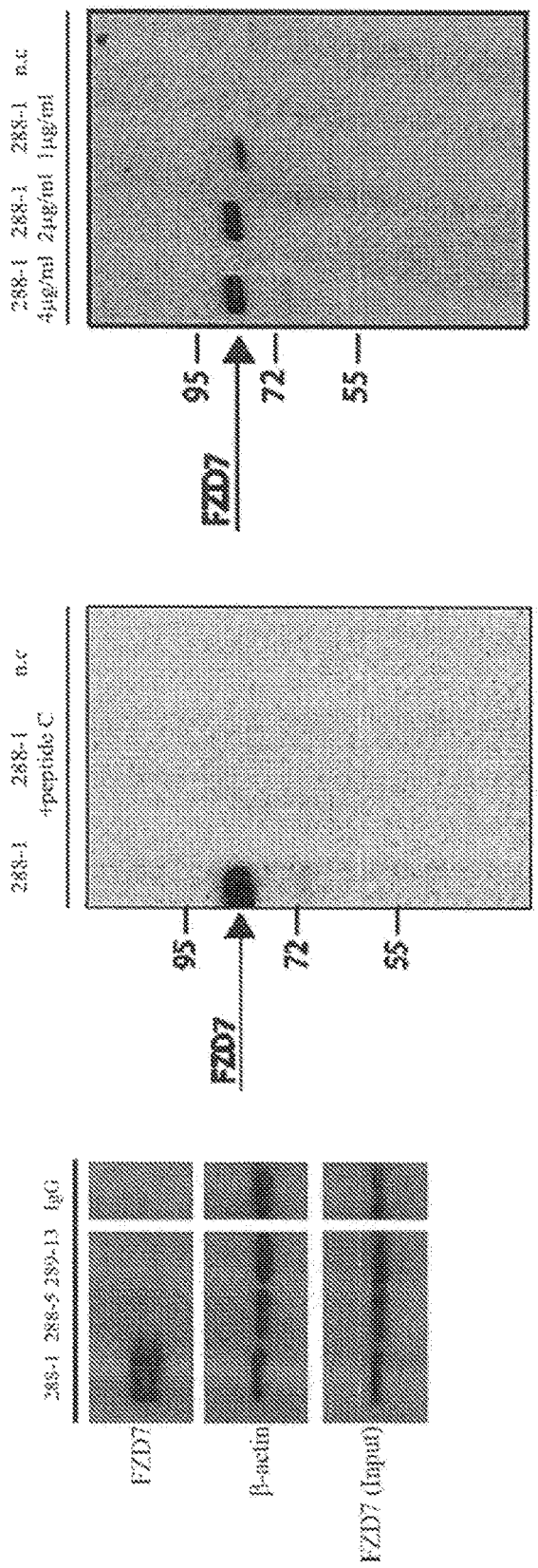

FIG. 11A presents the results of an immune-precipitation assay confirming the specificity of monoclonal antibody 228-1 binding to the FZD7 receptor in an SK-MEL28 cell lysate.

FIG. 11B presents the results of a peptide blocking assay demonstrating the specificity of monoclonal antibody 288-1 to antigen C of the FZD7 receptor.

FIG. 11C presents Western Blot data showing serial dilutions of the monoclonal antibody 288-1 (4 ug/ml, 2 ug/ml and 1 ug/ml), confirming specificity of this antibody for FZD7.

Figure 12:
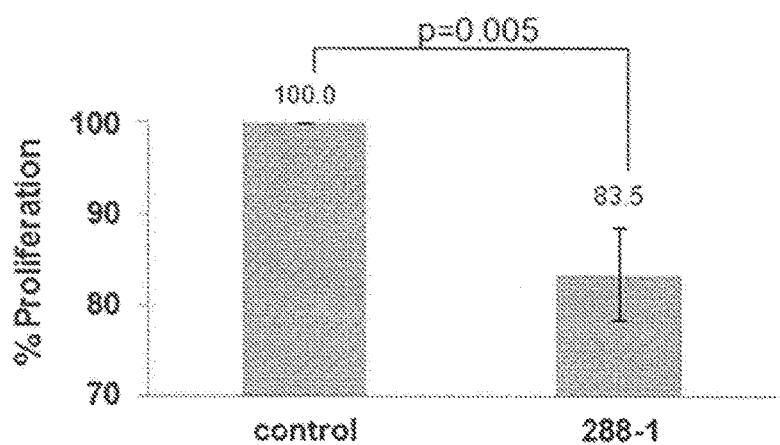

FIG. 12 presents a bar graph showing that stabilized anti FZD7 Ab 288-1 reduces proliferation in melanoma cells. Control untreated cells were set as 100%, average of % proliferation as indicated by the range markers in the bar graph.

Figure 13A:
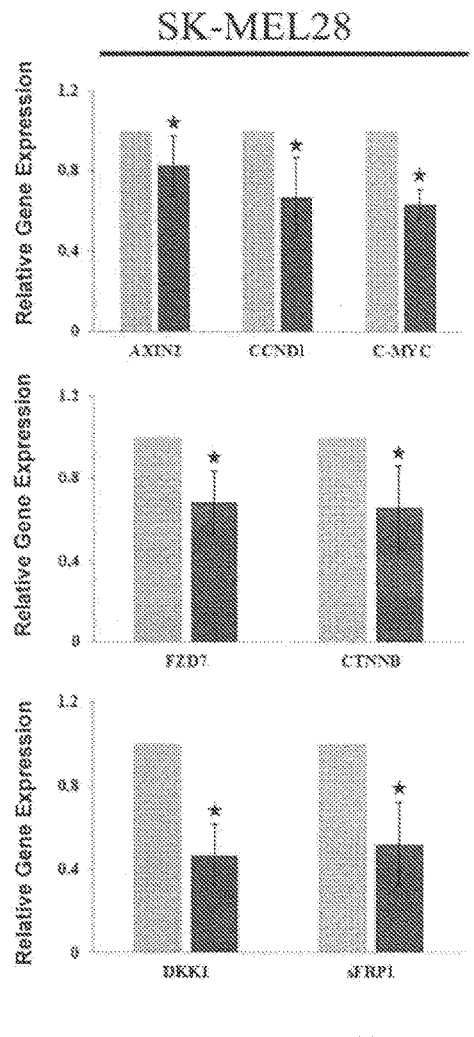

FIG. 13A presents results (bar graphs) demonstrating MAb 288-1 inhibits expression of Wnt Signaling pathway target genes AXIN, CCND1, C-MYC, FZD7, and CTNNB (β-catenin), and Wnt pathway inhibitors DKK1 and sFRP1 in SK-MEL28 cells.

Figure 13B:
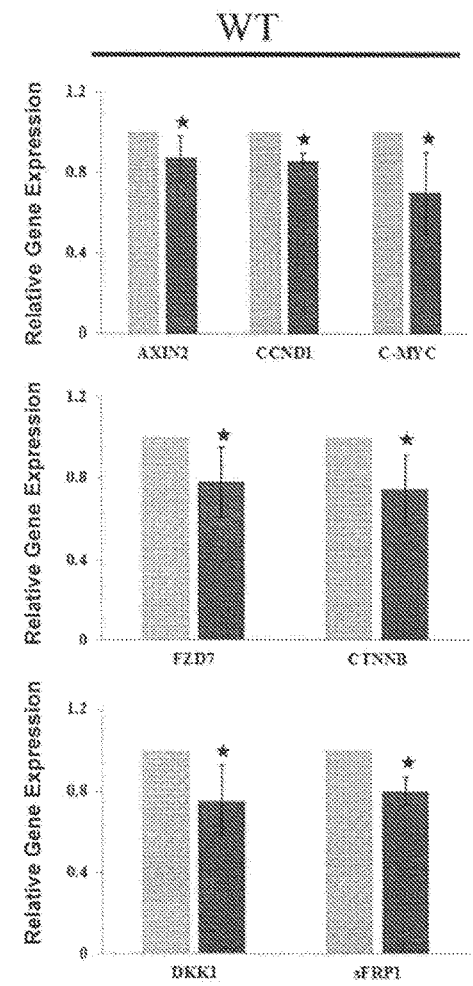

FIG. 13B presents results (bar graphs) demonstrating MAb 288-1 inhibits expression of Wnt Signaling pathway target genes: AXIN, CCND1, C-MYC; FZD7; CTNNB (β-catenin), and Wnt pathway inhibitors: DKK1 and sFRP1; in Wilms' tumor cells.

Figure 13C:
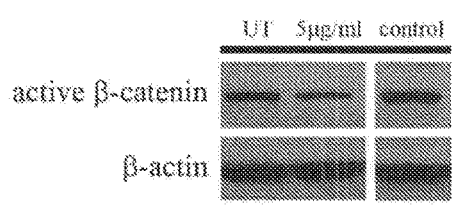
Figure 14A:
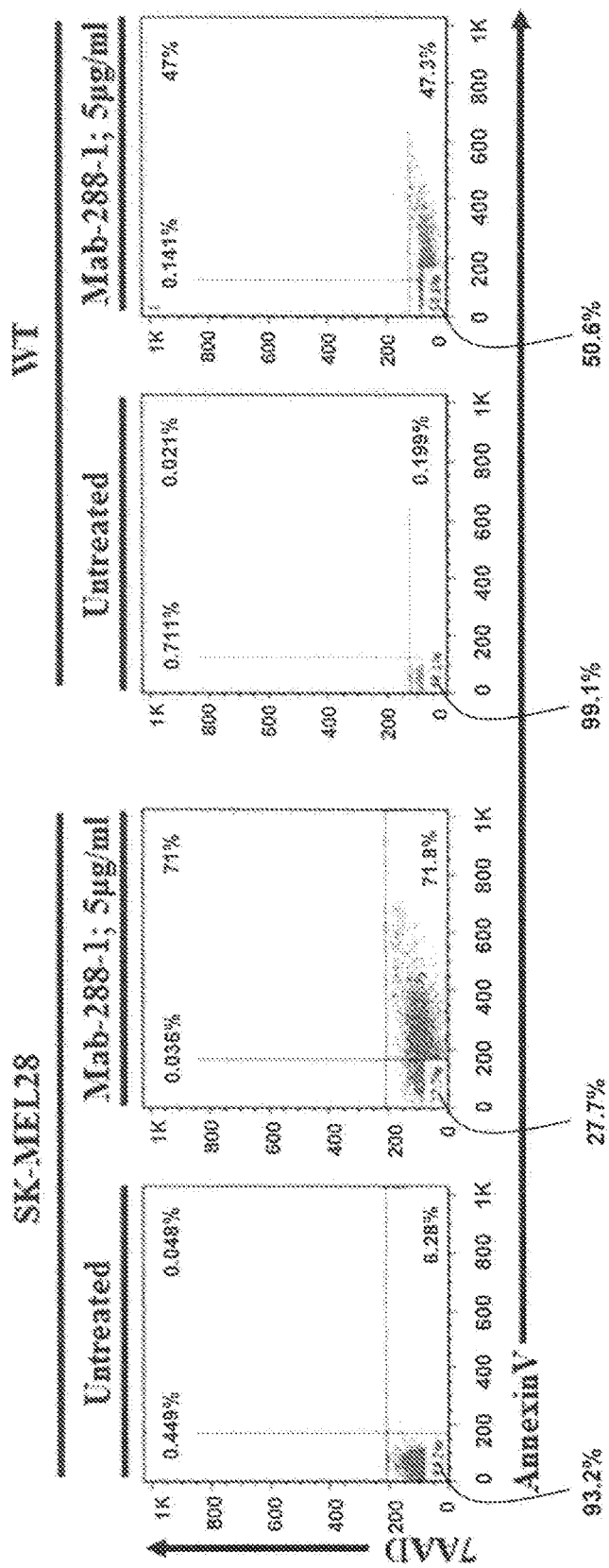

FIG. 13C presents Western blot data showing that protein levels of active β-Catenin were reduced by 5 ug/ml anti FZD7 Ab 288-1 in Wilms' tumor cells FIG. 14A shows the results of flow cytometry analysis of MAb 288-1 treated and untreated cells using annexin V and 7-Amino actinmyosin D (7AAD) staining, wherein the is an increase in the percent of pre-apoptotic cells in SK-MEL28 (71%) and WT (47%) treated cells.

Figure 14B:
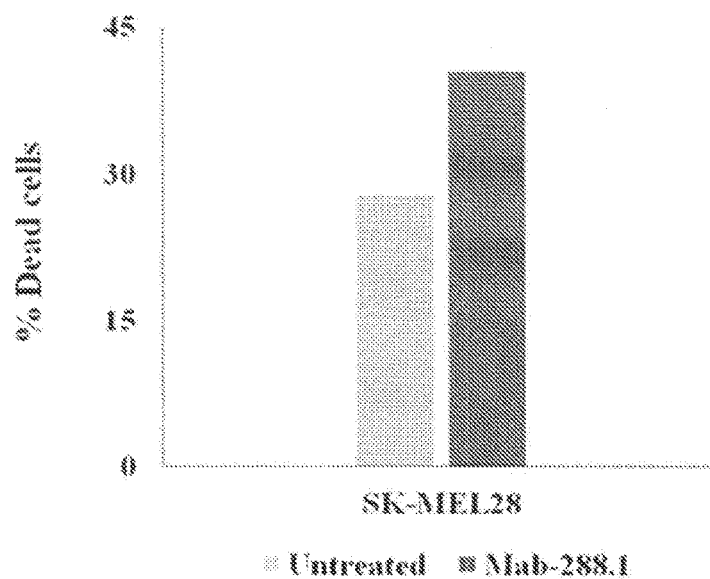

FIG. 14B presents data (bar graph) showing increased % of dead SK-MEL28 cells following MAb-288-1 treatment.

Figure 14C:
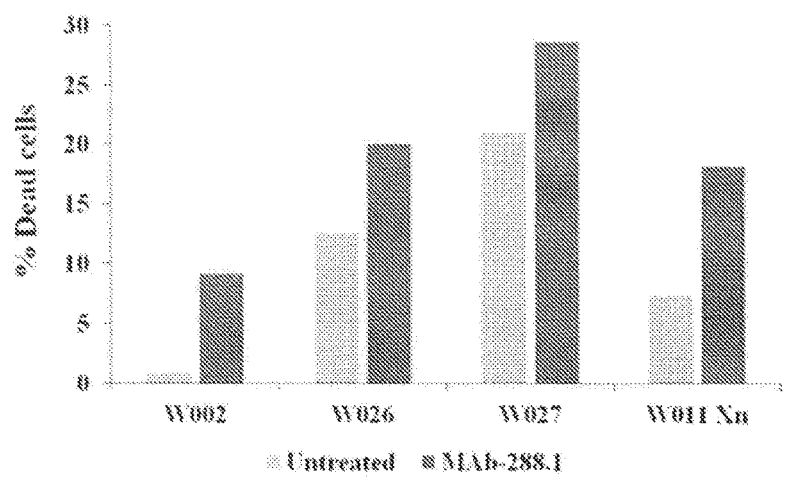

FIG. 14C presents data (bar graphs) showing increased % of dead WT cells following MAb-288-1 treatment. W002, W026, W0027 and W011Xn represent Wilms' tumor derived cells from different donors.

Figure 15A:
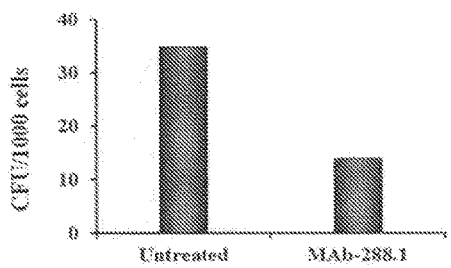

FIG. 15A presents Colony Forming Units (CFU) data (bar graph) demonstrating that the number of CFU decreased in SK-MEL28 cells treated with MAb 288.1.

Figure 15B:
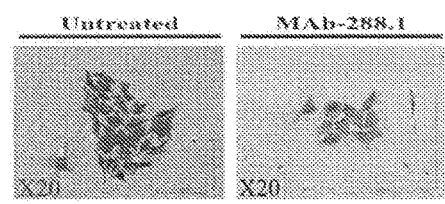

FIG. 15B shows micrographs of untreated and MAb 288.1 treated SK-MEL28 cells, demonstrating smaller colony size in SK-MEL28 cells treated with MAb 288.1.

Figure 15C:
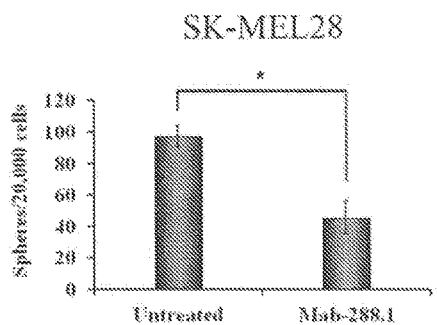

FIG. 15C presents the results of a sphere formation assay (bar graph) demonstrating that the number of spheres formed decreased in SK-MEL28 cells treated with MAb 288.1.

Figure 15D:
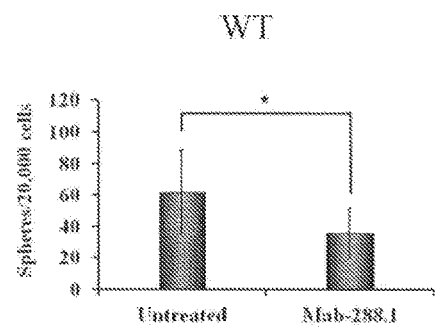

FIG. 15D presents the results of a sphere formation assay (bar graph) demonstrating that the number of spheres formed decreased in WT cells treated with MAb 288.1.

Figure 15E:
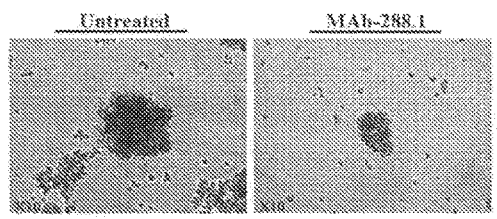

FIG. 15E shows representative micrographs of spheres formed from SK-MEL28 cells in the presence or absence (untreated) of MAb 288.1. Less condensed and smaller spheres were formed following MAb 288.1 treatment.

Figure 15F:
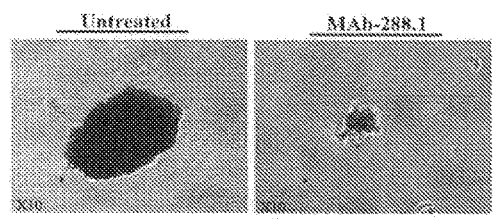

FIG. 15F shows representative micrographs of spheres formed from WT cells in the presence or absence (untreated) of MAb 288.1. Less condensed and smaller spheres were formed following MAb 288.1 treatment.

Figure 16A:
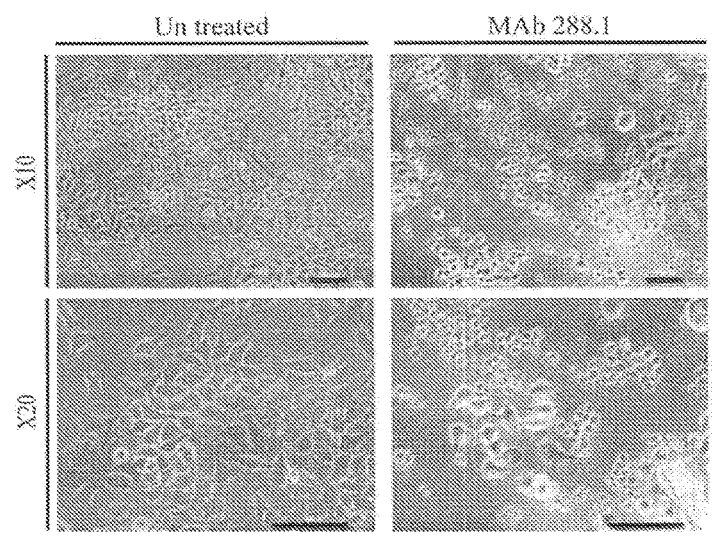

FIG. 16A presents micrographs showing morphological changes in SK-MEL28 cells treated with MAb 288.1 as compared with untreated cells.

Figure 16B:
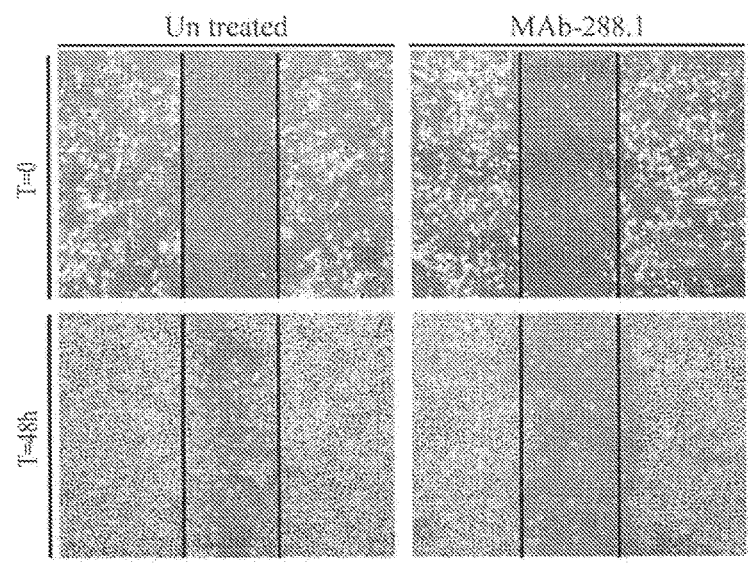

FIG. 16B presents micrographs of a wound healing migration assay showing that migration of SK-MEL28 cells treated with MAb 288.1 was significantly inhibited, as compared with untreated cells.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although examples are not limited in this regard, the terms "plurality" and "a plurality" as used herein may include, for example, "multiple" or "two or more". The terms "plurality" or "a plurality" may be used throughout the specification to describe two or more components, elements, units, parameters, or the like. Unless explicitly stated, the method examples described herein are not constrained to a particular order or sequence. Additionally, some of the described method examples or elements thereof can occur or be performed at the same point in time.

Definitions

The term "antibody," as used herein, includes whole antibodies and any antigen binding fragment (i.e., "antigen-binding portion" or "antigen-binding domain") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region (abbreviated herein as CH). Each light chain is comprised of a light chain variable region (abbreviated herein as VL) and a light chain constant region (abbreviated herein as CL). The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

The term "epitope," as used herein, means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "discontinuous epitope," as used herein, means a conformational epitope on a protein antigen which is formed from at least two separate regions in the primary sequence of the protein.

The term "isolated antibody," as used herein, is intended to refer to an antibody which is substantially free of other antibodies having different antigenic specificities (e.g., an isolated antibody that binds specifically to amino acid residues in the cytoplasmic domain of FZD7 is substantially free of antibodies that specifically bind other antigens). An isolated antibody that specifically binds to an epitope, isoform or variant of a human Frizzled receptor may, however, have cross-reactivity to other related antigens, e.g., from other species (e.g., Frizzled species homologs). An isolated antibody may have cross-reactivity with other antigens yet still remain specific, namely bind only to a particular epitope. In the case of cross-reactivity, this epitope may be present on more than one protein or antigen. Moreover, an isolated antibody may be substantially free of other cellular material and/or chemicals.

The term "monoclonal antibody," as used herein, refers to a preparation of antibody molecules of single molecular composition. A monoclonal antibody composition displays a single binding specificity and affinity for a particular epitope.

The term "subject," as used herein, includes any human or non-human animal. The term "non-human animal" includes all vertebrates, e.g., mammals and non-mammals, such as non-human primates, sheep, dog, cow, chickens, amphibians, reptiles, etc.

The following examples are presented in order to more fully illustrate the preferred embodiments of the invention. They should in no way be construed, however, as limiting the broad scope of the invention The present invention provides isolated antibodies or antigen binding domains thereof that specifically bind one or more human frizzled receptors (FZDs). In certain embodiments, the antibodies or antigen binding domains thereof specifically bind two, three, four, five, six, seven, eight, nine, or ten frizzled receptors. The human frizzled receptor or receptors bound by the antibodies may be selected from the group consisting of FZD 1, FZD2, FZD3, FZD4, FZD5, FZD6, FZD7, FZD8, FZD9, and FZD10. In certain embodiments, the one or more human frizzled receptors comprise FZD1, FZD2, FZD5, FZD7, and/or FZD8. In certain embodiments, the one or more human frizzled receptors comprise FZD7. In certain embodiments, the one or more human frizzled receptors comprise FZD7, FZD5 and/or FZD8. In certain embodiments, the antibody specifically binds FZD7. In other embodiments, the antibody specifically binds to both FZD7 and FZD1. In certain embodiments, the antibody specifically binds to both FZD7 and FZD2. In certain embodiments, the antibody specifically binds to both FZD7 and FZD3. In certain embodiments, the antibody specifically binds to both FZD7 and FZD4. In certain embodiments, the antibody specifically binds to both FZD7 and FZD5. In certain embodiments, the antibody specifically binds to both FZD7 and FZD6. In certain embodiments, the antibody specifically binds to both FZD7 and FZD8. In certain embodiments, the antibody specifically binds to both FZD7 and FZD9. In certain embodiments, the antibody specifically binds to both FZD7 and FZD10. In certain embodiments, the antibody specifically binds to FZD7, FZD1, FZD2, FZD5, FZD7, and FZD8. The full-length amino acid (AA) sequences for human FZD1-10 are known in the art and also provided herein as SEQ ID NO:5 (FZD1 AA), SEQ ID NO:6 (FZD2 AA), SEQ ID NO:7 (FZD3 AA), SEQ ID NO:8 (FZD4 AA), SEQ ID NO:9 (FZD5 AA), SEQ ID NO:10 (FZD6 AA), SEQ ID NO:11 (FZD7 AA), SEQ ID NO:12 (FZD8 AA), SEQ ID NO:13 (FZD9 AA) and SEQ ID NO:14 (FZD10 AA).

In certain embodiments, the antibody or antigen binding portion thereof described herein specifically binds to human FZD7. In other embodiments, that antibody, may further specifically bind or cross-react with one or more additional human frizzled receptors. In certain embodiments, the one or more additional human frizzled receptors are selected from the group consisting of FZD2, FZD5, and FZD8. In certain embodiments, the one or more additional human frizzled receptors are selected from the group consisting of FZD1, FZD2, FZD5, and FZD8. In certain embodiments, the one or more additional human frizzled receptors are selected from the group consisting of FZD1, FZD2, FZD5, and FZD8. In certain embodiments, the one or more additional human frizzled receptors are selected from the group consisting of FZD1, FZD2, FZD5, and FZD8. In certain embodiments, the one or more additional human frizzled receptors comprise both FZD5 and FZD8. In certain embodiments, the one or more additional human frizzled receptors comprise are selected from the group consisting of FZD1, FZD2, FZD5, and FZD8.

In certain embodiments, the antibody specifically binds to three or more human frizzled receptors. In certain embodiments, the three or more human frizzled receptors comprise three or more frizzled receptors selected from the group consisting of FZD1, FZD2, FZD5, FZD7, and FZD8. In certain embodiments, the antibody further specifically binds to one or more additional human frizzled receptors.

In certain embodiments, the antibody specifically binds to the extracellular domain within the one or more human frizzled receptors to which it binds. Sequences of the extracellular domain of each of the human frizzled receptors are known in the art.

In certain embodiments, the antibody specifically binds to the Fri domain (FRI) (also known as the cysteine-rich domain (CRD)) within the human frizzled receptor(s) to which it binds. Sequences of the Fri domain of each of the human frizzled receptors are known in the art.

In certain embodiments, the antibody specifically binds to the Fri domain (FRI) (cysteine-rich domain (CRD)) within the human frizzled 7 receptor. In certain embodiments the antibody binds specifically to SEQ ID NO:2 within the FRI domain of Frizzled 7. In certain embodiments the antibody binds specifically to all of the amino acids (AAs) of SEQ ID NO:2 within the FRI domain of Frizzled 7. In certain embodiments the antibody binds specifically to a fraction of the amino acids (AAs) of SEQ ID NO:2 within the FRI domain of Frizzled 7. In certain embodiments the antibody binds specifically to at least five contiguous or non-contiguous amino acids (AAs) of SEQ ID NO:2 within the FRI domain of Frizzled 7. In certain embodiments the antibody binds specifically to at least four contiguous or non-contiguous amino acids (AAs) of SEQ ID NO:2 within the FRI domain of Frizzled 7. In certain embodiments the antibody binds specifically to at least five contiguous or non-contiguous amino acids (AAs) of SEQ ID NO:2 within the FRI domain of Frizzled 7. In certain embodiments the antibody binds specifically to at least six contiguous or non-contiguous amino acids (AAs) of SEQ ID NO:2 within the FRI domain of Frizzled 7. In certain embodiments the antibody binds specifically to at least seven contiguous or non-contiguous amino acids (AAs) of SEQ ID NO:2 within the FRI domain of Frizzled 7. In certain embodiments the antibody binds specifically to at least eight contiguous or non-contiguous amino acids (AAs) of SEQ ID NO:2 within the FRI domain of Frizzled 7. In certain embodiments the antibody binds specifically to at least nine contiguous or non-contiguous amino acids (AAs) of SEQ ID NO:2 within the FRI domain of Frizzled 7. In certain embodiments the antibody binds specifically to at least ten contiguous or non-contiguous amino acids (AAs) of SEQ ID NO:2 within the FRI domain of Frizzled 7. In certain embodiments the antibody binds specifically to at least eleven contiguous or non-contiguous amino acids (AAs) of SEQ ID NO:2 within the FRI domain of Frizzled 7. In certain embodiments the antibody binds specifically to at least twelve contiguous or non-contiguous amino acids (AAs) of SEQ ID NO:2 within the FRI domain of Frizzled 7. In certain embodiments the antibody binds specifically to at least thirteen contiguous or non-contiguous amino acids (AAs) of SEQ ID NO:2 within the FRI domain of Frizzled 7.

In certain embodiments, the antibody specifically binds to the Fri domain (FRI) (cysteine-rich domain (CRD)) within the human frizzled 2 receptor. In certain embodiments the antibody binds specifically to SEQ ID NO:2 within the FRI domain of Frizzled 2. In certain embodiments the antibody binds specifically to all of the amino acids (AAs) of SEQ ID NO:2 within the FRI domain of Frizzled 2. In certain embodiments the antibody binds specifically to a fraction of the amino acids (AAs) of SEQ ID NO:2 within the FRI domain of Frizzled 2. In certain embodiments the antibody binds specifically to at least five contiguous or non-contiguous amino acids (AAs) of SEQ ID NO:2 within the FRI domain of Frizzled 2. In certain embodiments the antibody binds specifically to at least four contiguous or non-contiguous amino acids (AAs) of SEQ ID NO:2 within the FRI domain of Frizzled 2. In certain embodiments the antibody binds specifically to at least five contiguous or non-contiguous amino acids (AAs) of SEQ ID NO:2 within the FRI domain of Frizzled 2. In certain embodiments the antibody binds specifically to at least six contiguous or non-contiguous amino acids (AAs) of SEQ ID NO:2 within the FRI domain of Frizzled 2. In certain embodiments the antibody binds specifically to at least seven contiguous or non-contiguous amino acids (AAs) of SEQ ID NO:2 within the FRI domain of Frizzled 2. In certain embodiments the antibody binds specifically to at least eight contiguous or non-contiguous amino acids (AAs) of SEQ ID NO:2 within the FRI domain of Frizzled 2. In certain embodiments the antibody binds specifically to at least nine contiguous or non-contiguous amino acids (AAs) of SEQ ID NO:2 within the FRI domain of Frizzled 2. In certain embodiments the antibody binds specifically to at least ten contiguous or non-contiguous amino acids (AAs) of SEQ ID NO:2 within the FRI domain of Frizzled 2. In certain embodiments the antibody binds specifically to at least eleven contiguous or non-contiguous amino acids (AAs) of SEQ ID NO:2 within the FRI domain of Frizzled 2. In certain embodiments the antibody binds specifically to at least twelve contiguous or non-contiguous amino acids (AAs) of SEQ ID NO:2 within the FRI domain of Frizzled 2. In certain embodiments the antibody binds specifically to at least thirteen contiguous or non-contiguous amino acids (AAs) of SEQ ID NO:2 within the FRI domain of Frizzled 2.

In certain embodiments, the antibody specifically binds to a transmembrane portion of the human frizzled receptor(s). Sequences of the transmembrane portion of each of the human frizzled receptors are known in the art.

In certain embodiments, the antibody specifically binds to a cytoplasmic portion of the human frizzled receptor(s). Sequences of the cytoplasmic portion of each of the human frizzled receptors are known in the art.

In certain embodiments, the antibody specifically binds to a portion of the human frizzled receptor(s), wherein this portion consists of both transmembrane and cytoplasmic sections.

In certain embodiments, the antibody specifically binds to a transmembrane portion of the human frizzled 7 receptor. In certain embodiments, the antibody binds to all or part of SEQ ID NO: 1 within this transmembrane portion.

In certain embodiments, the antibody specifically binds to a cytoplasmic portion of the human frizzled 7 receptor. In certain embodiments, the antibody binds to all or part of SEQ ID NO: 1 within this cytoplasmic portion.

In certain embodiments, the antibody specifically binds to a portion of the human frizzled 7 receptor, wherein this portion consists of both transmembrane and cytoplasmic sections. In certain embodiments, the antibody binds to all or part of SEQ ID NO: 1 within this portion In certain embodiments, an individual antigen-binding site of a FZD-binding antibody described herein is capable of binding the one, two, three, four, or five or more human frizzled receptors. In certain embodiments, an individual antigen-binding site of the FZD-binding antibody is capable of specifically binding one, two, three, four, or five human frizzled receptors selected from the group consisting of FZD 1, FZD2, FZD5, FZD7, and FZD8.

In certain embodiments, the FZD-binding antibody binds to one or more (for example, two or more, three or more, or four or more) human frizzled receptors with a dissociation constant (KQ) of about 1000 nM or less, about 100 nM or less, about 40 nM or less, about 20 nM or less, or about 10 nM or less. For example, in certain embodiments, a FZD-binding antibody described herein that binds to more than one FZD receptor, binds to those FZDs receptors with a KD of about 100 nM or less, about 20 nM or less, or about 10 nM or less. In certain embodiments, the FZD-binding antibody binds to each of one or more (e.g., 1, 2, 3, 4, or 5) of the following FZDs with a dissociation constant of about 40 nM or less: FZD1, FZD2, FZD5, FZD7, and FZD8. In certain embodiments, the FZD-binding antibody binds to each of one or more of the following FZDs with a dissociation constant of about 10 nM or less: FZD1, FZD2, FZD5, FZD7, and FZD8. In certain embodiments, the FZD-binding antibody binds to each of the following FZDs with a dissociation constant of about 10 nM or less: FZD1, FZD2, FZD5, FZD7, and FZD8.

In certain embodiments, the FZD-binding antibody binds to one or more human frizzled receptors with an EC50 of about 1000 nM or less, about 100 nM or less, about 40 nM or less, about 20 nM or less, about 10 nM or less, or about 1 nM or less. For example, in certain embodiments, a FZD-binding antibody described herein that binds to more than one FZD has an EC50 of about 40 nM or less, about 20 nM or less, or about 10 nM or less, with respect to those FZDs. In certain embodiments, the FZD-binding antibody has an EC50 of about 20 nM or less with respect to one or more (e.g., 1, 2, 3, 4, or 5) of the following FZDs: FZD1, FZD2, FZD5, FZD7, and FZD8. In certain embodiments, the FZD-binding antibody has an EC50 of about 10 nM or less with respect to one or more (e.g., 1, 2, 3, 4, or 5) of the following FZDs: FZD1, FZD2, FZD5, FZD7, and FZD8.

In certain embodiments, the FZD-binding antibody specifically binds to the sequence RFYHRLSHSSKGETAV (SEQ ID NO: 1) within the human frizzled 7 receptor. In certain embodiments, the FZD-binding antibody specifically binds to a sequence comprising at least 5 amino acids of the sequence RFYHRLSHSSKGETAV (SEQ ID NO: 1) within a human frizzled receptor. In certain embodiments, these five amino acids are contiguous. In certain embodiments, these five amino acids are not contiguous. In certain embodiments, these five amino acids are contiguous amino acids RFYHR. In certain embodiments, these five amino acids are contiguous amino acids FYHRL. In certain embodiments, these five amino acids are contiguous amino acids YHRLS. In certain embodiments, these five amino acids are contiguous amino acids HRLSH. In certain embodiments, these five amino acids are contiguous amino acids RLSHS. In certain embodiments, these five amino acids are contiguous amino acids LSHSS. In certain embodiments, these five amino acids are contiguous amino acids SHSSK. In certain embodiments, these five amino acids are contiguous amino acids HSSKG. In certain embodiments, these five amino acids are contiguous amino acids SSKGE. In certain embodiments, these five amino acids are contiguous amino acids SKGET. In certain embodiments, these five amino acids are contiguous amino acids KGETA. In certain embodiments, these five amino acids are contiguous amino acids GETAV. In one embodiment, the FZD-binding antibody may be the antibody produced by the hybridoma cell line 288-1. In another embodiment, the FZD-binding antibody may be the antibody produced by the hybridoma cell line 288-2. In another embodiment, the FZD-binding antibody may be the antibody produced by the hybridoma cell line 288-5.

Hybridoma cell line 288-1 has been deposited in the American Type Culture Collection (ATCC®), Manassas, Va., USA, under Registration Number PTA-123746, on 4 Jan. 2017. The hybridoma has been deposited under the Budapest Treaty on the International Recognition of the Deposit of Microorganisms for the Purposes of Patent Procedure, and comply with the criteria set forth in 37 CFR § 1.801-1.809 regarding availability and permanency of deposits.

Hybridoma cell line 288-5 have been deposited in the American Type Culture Collection (ATCC®), Manassas, Va., USA, under Registration Number PTA-123744, on 4 Jan. 2017. The hybridoma has been deposited under the Budapest Treaty on the International Recognition of the Deposit of Microorganisms for the Purposes of Patent Procedure, and comply with the criteria set forth in 37 CFR § 1.801-1.809 regarding availability and permanency of deposits.

In certain embodiments, the FZD-binding antibody binds to at least part of a sequence in FZD1, FZD2, FZD3, FZD4, FZD5, FZD6, FZD8, FZD9 and/or FZD 10 that corresponds to the sequence RFYHRLSHSSKGETAV (SEQ ID NO: 1) in FZD7.

In certain embodiments, the FZD-binding antibody specifically binds to the sequence QEDAGLEVHQFYPL (SEQ ID NO: 2) within the human frizzled receptors 2 or 7. In certain embodiments, the FZD-binding antibody specifically binds to a sequence comprising at least 5 amino acids of the sequence QEDAGLEVHQFYPL (SEQ ID NO: 2) within a human frizzled receptor. In certain embodiments, these five amino acids are contiguous. In certain embodiments, these five amino acids are not contiguous. In certain embodiments, these five amino acids are contiguous amino acids QEDAG. In certain embodiments, these five amino acids are contiguous amino acids EDAGL. In certain embodiments, these five amino acids are contiguous amino acids DAGLE. In certain embodiments, these five amino acids are contiguous amino acids AGLEV. In certain embodiments, these five amino acids are contiguous amino acids GLEVH. In certain embodiments, these five amino acids are contiguous amino acids LEVHQ. In certain embodiments, these five amino acids are contiguous amino acids EVHQF. In certain embodiments, these five amino acids are contiguous amino acids VHQFY. In certain embodiments, these five amino acids are contiguous amino acids HQFYP. In certain embodiments, these five amino acids are contiguous amino acids QFYPL. In one embodiment the FZD-binding antibody may be the antibody produced by the hybridoma cell line 288-4. In another embodiment the FZD-binding antibody may be the antibody produced by the hybridoma cell line 289-5. In another embodiment the FZD-antibody may be the antibody produced by the hybridoma cell line number 4.

In certain embodiments, the antibody binds to at least part of a sequence in FZD1, FZD3, FZD4, FZD5, FZD6, FZD8, FZD9 and/or FZD 10 that corresponds to the sequence QEDAGLEVHQFYPL (SEQ ID NO: 2) in FZD2 or FZD7.

In certain embodiments, the FZD-binding antibody specifically binds to the sequence PGASDGRGRPAFPFS (SEQ ID NO: 3) within human frizzled receptor 7. In certain embodiments, the FZD-binding antibody specifically binds to a sequence comprising at least 5 amino acids of the sequence PGASDGRGRPAFPFS (SEQ ID NO: 3) within a human frizzled receptor. In certain embodiments, these five amino acids are contiguous. In certain embodiments, these five amino acids are not contiguous. In certain embodiments, these five amino acids are contiguous amino acids PGASD. In certain embodiments, these five amino acids are contiguous amino acids GASDG. In certain embodiments, these five amino acids are contiguous amino acids ASDGR. In certain embodiments, these five amino acids are contiguous amino acids SDGRG. In certain embodiments, these five amino acids are contiguous amino acids DGRGR. In certain embodiments, these five amino acids are contiguous amino acids GRGRP. In certain embodiments, these five amino acids are contiguous amino acids RGRPA. In certain embodiments, these five amino acids are contiguous amino acids GRPAF. In certain embodiments, these five amino acids are contiguous amino acids RPAFP. In certain embodiments, these five amino acids are contiguous amino acids PAFPF. In certain embodiments, these five amino acids are contiguous amino acids AFPFS.

In certain embodiments, the antibody binds to at least part of a sequence in FZD1, FZD3, FZD4, FZD5, FZD6, FZD8, FZD9 and/or FZD 10 that corresponds to the sequence PGASDGRGRPAFPFS (SEQ ID NO: 3) in FZD7.

In certain embodiments, the FZD-binding antibody specifically binds to the sequence DGSGGPGGGPTAYPTA (SEQ ID NO: 4) within human frizzled receptor 7. In certain embodiments, the FZD-binding antibody specifically binds to a sequence comprising at least 5 amino acids of the sequence DGSGGPGGGPTAYPTA (SEQ ID NO: 4) within a human frizzled receptor. In certain embodiments, these five amino acids are contiguous. In certain embodiments, these five amino acids are not contiguous. In certain embodiments, these five amino acids are contiguous amino acids DGSGG. In certain embodiments, these five amino acids are contiguous amino acids GSGGP. In certain embodiments, these five amino acids are contiguous amino acids SGGPG. In certain embodiments, these five amino acids are contiguous amino acids GGPGG. In certain embodiments, these five amino acids are contiguous amino acids GPGGG. In certain embodiments, these five amino acids are contiguous amino acids PGGGP. In certain embodiments, these five amino acids are contiguous amino acids GGGPT. In certain embodiments, these five amino acids are contiguous amino acids GGPTA. In certain embodiments, these five amino acids are contiguous amino acids GPTAY. In certain embodiments, these five amino acids are contiguous amino acids PTAYP. In certain embodiments, these five amino acids are contiguous amino acids TAYPT. In certain embodiments, these five amino acids are contiguous amino acids AYPTA. In one embodiment the FZD-binding antibody may be the antibody produced by the hybridoma cell line 289-6. In another embodiment the FZD-binding antibody may be the antibody produced by the hybridoma cell line 289-12. In another embodiment the FZD-binding antibody may be the antibody produced by the hybridoma cell line 289-18. In another embodiment the FZD-binding antibody may be the antibody produced by the hybridoma cell line 289-3.1 n another embodiment the FZD-antibody may be the antibody produced by the hybridoma cell line number 289-13.

Hybridoma cell line 289-13 has been deposited in the American Type Culture Collection (ATCC®), Manassas, Va., USA, under Registration Number PTA-123745, on 4 Jan. 2017. The hybridoma has been deposited under the Budapest Treaty on the International Recognition of the Deposit of Microorganisms for the Purposes of Patent Procedure, and comply with the criteria set forth in 37 CFR § 1.801-1.809 regarding availability and permanency of deposits.

In certain embodiments, the FZD-binding antibody binds to at least part of a sequence in FZD1, FZD3, FZD4, FZD5, FZD6, FZD8, FZD9 and/or FZD 10 that corresponds to the sequence DGSGGPGGGPTAYPTA (SEQ ID NO: 4) in FZD7.

In certain embodiments, the FZD-binding antibody inhibits binding of a ligand (e.g, a Wnt) to a portion of the FZD receptor (e.g, the BBS of the FZD). In certain embodiments, the FZD-binding antibody inhibits binding of a signaling molecule (e.g, dishevelled (Dvl), an intracellular protein) to a portion of the FZD receptor (e.g, the cytosolic portion).

In certain embodiments, the FZD-binding antibody is an IgG1 antibody. In certain embodiments, the FZD-binding antibody is an IgG2 antibody. In certain embodiments, the FZD-binding antibody is an IgG3 antibody. In certain embodiments, the FZD-binding antibody is an IgG4 antibody. In certain embodiments, the FZD-binding antibody is an IgA antibody. In certain embodiments, the FZD-binding antibody is an IgD antibody. In certain embodiments, the FZD-binding antibody is an IgE antibody. In certain embodiments, the FZD-binding antibody is an IgM antibody. In certain embodiments, the antibody is a monoclonal antibody. In certain embodiments, the antibody is a human antibody or a humanized antibody. In certain embodiments, the antibody is a chimeric antibody or a chimeric/humanized antibody. In certain embodiments, the antibody is an antibody fragment.

The antibodies of the present invention can be assayed for specific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitation reac-tions, gel diffusion precipitin reactions, immunodiffusion assays, agglutination assays, complement-fixation assays, immunoradiometric assays, fluorescent immunoassays, and protein A immunoassays. Such assays are routine and well known in the art.

For example, the specific binding of an antibody to a human frizzled receptor may be determined using ELISA.

An ELISA assay comprises preparing antigen, coating wells of a 96 well microtiter plate with antigen, adding the FZD-binding antibody conjugated to a detectable compound such as an enzymatic substrate (e.g. horseradish peroxidase or alkaline phosphatase) to the well, incubating for a period of time and detecting the presence of the antigen. In some embodiments, the FZD-binding antibody is not conjugated to a detectable compound, but instead a second conjugated antibody that recognizes the FZD-binding antibody is added to the well. In some embodiments, instead of coating the well with the antigen, the FZD-binding antibody can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art.

The binding affinity of an antibody to a human frizzled receptor and the off-rate of an antibody-antigen interaction can be determined by competitive binding assays. One example of a competitive binding assay is a radioimmunoassay comprising the incubation of labeled anti-gen (e.g. $^3$H or $^{125}$I), or fragment or variant thereof, with the antibody of interest in the presence of increasing amounts of unlabeled antigen followed by the detection of the antibody bound to the labeled antigen. The affinity of the antibody against a frizzled receptor and the binding off-rates can be determined from the data by scatchard plot analysis. In some embodiments, BIAcore kinetic analysis is used to determine the binding on and off rates of antibodies that bind one or more human frizzled receptors. BIAcore kinetic analysis comprises analyzing the binding and dissociation of antibodies from chips with immobilized FZD antigens on their surface.

In certain embodiments, the antibody is an antagonist of at least one human frizzled receptor (i.e., 1, 2, 3, 4, 5, 6, 7, 8, 9, or 10 FZDs) bound by the antibody. In certain embodiments, the antibody inhibits at least about 10%, at least about 20%, at least about 30%, at least about 50%, at least about 75%, at least about 90%, or about 100% of one or more activity of the bound human frizzled receptor.

In certain embodiments, the FZD-binding antibody inhibits binding of a ligand to at least one human frizzled receptor. In certain embodiments, the FZD-binding antibody inhibits binding of a ligand to the Biological Binding site (BBS) of the human frizzled receptor. In certain embodiments, the ligand is a human Wnt protein. In certain embodiments, the inhibition of binding of a particular ligand to a particular human frizzled protein provided by the FZD-binding antibody is at least about 10%, at least about 25%, at least about 50%, at least about 75%, at least about 90%, or at least about 95%. In certain embodiments, an antibody that inhibits binding of a ligand such as a Wnt to a FZD, further inhibits Wnt signaling (e g, inhibits canonical Wnt signaling).

In certain embodiments, the FZD-binding antibody inhibits Wnt signaling. It is understood that a FZD-binding antibody that inhibits Wnt signaling may, in certain embodiments, inhibit signaling by one or more Wnts, but not necessarily by all Wnts. In certain alternative embodiments, signaling by all human Wnts may be inhibited. In certain embodiments, signaling by one or more Wnts selected from the group consisting of WNT1, WNT2, WNT2B/13, WNT3, WNT3A, WNT4, WNT5A, WNT5B, WNT6, WNT7A, WNT7B, WNT8A, WNT8B, WNT9A (previously WNT 14), WNT9B (previously WNT15), WNT10A, WNT10B, WNT11, and WNT16 is inhibited. In certain embodiments, the Wnt signaling that is inhibited is signaling by WNT1, WNT2, WNT3, WNT3A, WNT7a, WNT7b, and/or WNT10B. In certain embodiments, the antibody inhibits signaling by (at least) WNT1, WNT3A, WNT7b, and WNT10B. In particular embodiments, the antibody inhibits signaling by (at least) WNT3A. In certain embodiments, the inhibition of signaling by a Wnt provided by the FZD-binding antibody is a reduction in the level of signaling by the Wnt of least about 10%, at least about 25%, at least about 50%, at least about 75%, at least about 90%, or at least about 95%. In certain embodiments, the Wnt signaling that is inhibited is canonical Wnt signaling. In certain embodiments, the Wnt signaling that is inhibited is non-canonical Wnt signaling.

In vivo and in vitro assays for determining whether a FZD-binding antibody inhibits Wnt signaling are known in the art. For example, cell-based, luciferase reporter assays utilizing a TCF/Luc reporter vector containing multiple copies of the TCF-binding domain upstream of a firefly luciferase reporter gene may be used to measure canonical Wnt signaling levels in vitro. The level of Wnt signaling in the presence of one or more Wnts with the FZD-binding antibody present is compared to the level of signaling without the FZD-binding antibody present. In addition to the TCF/luc reporter assay, the effect of a FZD-binding antibody on canonical Wnt signaling may be measured in vitro or in vivo by measuring the effect of the antibody on the level of expression of beta-catenin (as demonstrated in FIG. 6) or beta-catenin-regulated genes, such as c-myc.

In certain embodiments, the effect of an antibody on Wnt signaling may also be assessed by measuring the effect of the antibody on the phosphorylation state of Dishevelled-1, Dishevelled-2, Dishevelled-3, LRP5, LRP6, and/or beta-catenin. In still further embodiments, the effect of a FZD-binding antibody on Wnt signaling is determined by assessing the impact of the FZD-binding antibody on the expression level of one or more genes in a Wnt signature.

In certain embodiments, the FZD-binding antibodies have one or more of the following effects: inhibit proliferation of tumor cells, reduce the tumorigenecity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In certain embodiments, antibodies that specifically bind one or more human frizzled receptors trigger cell death via a conjugated toxin, chemotherapeutic antibody, radioisotope, or other such antibody. For example, in certain embodiments, an antibody to a human frizzled antibody is conjugated to a toxin that is activated in tumor cells expressing the FZD by protein internalization. In certain alternative embodiments, the antibody is not conjugated to a toxin, chemotherapeutic antibody, or radioisotope.

In another embodiment, the antibodies of the invention are antibody "fusion proteins," sometimes referred to herein as "antibody conjugates." The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. Possible conjugate partners include but are not limited to cytokines, cytotoxic antibodies, toxins, radioisotopes, chemotherapeutic antibody, anti-angiogenic antibodies, tyrosine kinase inhibitors, and other therapeutically active antibodies. The designation of an antibody as a fusion or conjugate is not meant to constrain it to any particular embodiment of the present invention. Rather, these terms are used to convey the broad concept that any antibody of the present invention may be linked genetically, chemically, or otherwise, to one or more polypeptides or molecules to provide some desirable property.

Suitable conjugates include, but are not limited to, drugs and cytotoxic antibodies including, for example, cytotoxic drugs (e.g., chemotherapeutic antibodies) or toxins or active fragments of such toxins. Cytotoxic antibodies also include radiochemicals made by conjugating radioisotopes to antibodies, or binding of a radionuclide to a chelating antibody that has been covalently attached to the antibody.

In certain embodiments, the FZD-binding antibodies are capable of inhibiting tumor growth. In certain embodiments, the FZD-binding antibodies are capable of inhibiting tumor growth in vivo (e.g, in a xenograft mouse model and/or in a human having cancer).

In certain embodiments, the FZD-binding antibodies are capable of reducing the tumorigenicity of a tumor. In certain embodiments, the antibody or antibody is capable of reducing the tumorigenicity of a tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of proliferating cancer cells is determined by a tumor cell proliferation assay. An example of a proliferation inhibition assay (MTS) used to test the efficacy of an anti-FZD antibody is provided in Example 2, below. In certain embodiments, the reduction in the number or frequency of proliferating cancer cells is determined by a tumor cell viability assay. An example of a viability assay (trypan blue) used to test the efficacy of an anti-FZD antibody is provided in Example 3, below. In certain embodiments, the reduction in the number or frequency of proliferating cancer cells is determined by a tumor cell apoptosis assay. An example of an apoptosis assay (annexin V staining) used to test the efficacy of an anti-FZD antibody is provided in Example 4, below.

In certain embodiments, antibodies to human frizzled receptors mediate cell death of a cell expressing the FZD protein via antibody-dependent cellular cytotoxicity (ADCC). ADCC involves cell lysis by effector cells that recognize the Fc portion of an antibody. Many lymphocytes, monocytes, tissue macrophages, granulocytes and eosinophils.

In certain embodiments, antibodies to one or more FZDs trigger cell death of a cell expressing the FZD protein (s) by activating complement-dependent cytotoxicity (CDC).

The ability of any particular antibody against one or more FZDs to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, the FZD-binding antibody has a circulating half-life in mice, cynomologous monkeys, or humans of at least about 10 hours, at least about 24 hours, at least about 3 days, at least about 1 week, or at least about 2 weeks. In certain embodiments, the FZD-binding antibody is an IgG antibody that has a circulating half-life in mice, cynomologous monkeys, or humans of at least about 10 hours, at least about 24 hours, at least about 3 days, at least about 1 week, or at least about 2 weeks. Methods of increasing the half-life of antibodies such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0. Known methods of increasing the circulating half-life of antibody fragments lacking the Fc region include such techniques as PEGylation.

Polyclonal antibodies can be prepared by any known method. Polyclonal antibodies are raised by immunizing an animal (e.g. a rabbit, rat, mouse, donkey, etc) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g. Complete or Incomplete Freund's Adjuvant) to km a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods or in vivo as ascites tumors in an animal. The monoclonal antibodies can then be purified from the culture medium or ascites fluid as described for polyclonal antibodies above.

Alternatively monoclonal antibodies can also be made using recombinant DNA methods. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described.

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human frizzled receptor(s) is a humanized antibody. In certain embodiments, such antibodies are used therapeutically to reduce antigenicity and HAMA (human anti-mouse antibody) responses when administered to a human subject. Humanized antibodies can be produced using various techniques known in the art. A common method for producing humanized antibodies is to graft CDR sequences from a MAb (produced by immunizing a rodent host) onto a human Ig backbone, and transfection of the chimeric genes into Chinese Hamster Ovary (CHO) cells which in turn produce a functional Ab that is secreted by the CHO cells. The methods described within this application are also useful for generating genetic alterations within Ig genes or chimeric Igs transfected within host cells. Humanized antibodies can also be made in transgenic mice containing human immunoglobulin loci that are capable upon immunization of producing the full repertoire of human antibodies in the absence of endogenous immunoglobulin production.

In certain alternative embodiments, the antibody to the human frizzled receptor(s) is a human antibody.

Human antibodies can be directly prepared using various techniques known in the art. Immortalized human B lymphocytes immunized in vitro or isolated from an immunized individual that produce an antibody directed against a target antigen can be generated Also, the human antibody can be selected from a phage library, where that phage library expresses human antibodies.

This invention also encompasses bispecific antibodies that specifically recognize a human frizzled receptor. Bispecific antibodies are antibodies that are capable of specifically recognizing and binding at least two different epitopes. The different epitopes can either be within the same molecule (e.g. the same human frizzled receptor) or on different molecules such that bispecific the antibodies can specifically recognize and bind a human frizzled receptor as well as, for example, 1) an effector molecule on a leukocyte such as a T-cell receptor (e.g. CD3) or Fc receptor (e.g. CD64, CD32, or CD16) or 2) a cytotoxic antibody as described in detail below. In certain embodiments, the bispecific antibody specifically binds at least one human frizzled receptor, as well as either VEGF, a Notch ligand, such as a delta-like ligand (for example, DLL4) or jagged, or at least one Notch receptor selected from the group consisting of Notch 1, Notch 2, Notch 3, and Notch 4. Bispecific antibodies can be intact antibodies or antibody fragments.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic antibodies to cells which express a particular antigen. These antibodies possess an antigen-binding arm and an arm which binds a cytotoxic antibody or a radionuclide chelator, such as EOTUBE, DPTA, DOTA, or TETA. Techniques for making bispecific antibodies are common in the art. Antibodies with more than two valencies are also contemplated. For example, trispecific antibodies can be prepared. Thus, in certain embodiments the antibodies to human frizzled receptor(s) are multispecific.

In certain embodiments, the antibodies described herein may be monospecific. For example, in certain embodiments, each of the one or more antigen-binding sites that an antibody contains is capable of binding the same one or more human FZD receptors (e.g, FZD1, FZD2, FZD5, FZD7, or FZD8, or a homologous epitope on some combination of the FZDs). In certain embodiments, an antigen-binding site of a monospecific antibody described herein is capable of binding one, two, three, four, or five (or more) human frizzled receptors.

According to the present invention, techniques can be adapted for the production of single-chain antibodies specific to one or more human frizzled receptors. In addition, methods can be adapted for the construction of Fab expression libraries to allow rapid and effective identification of monoclonal Fab fragments with the desired specificity for a FZD receptor, or derivatives, fragments, analogs or homologs thereof. Antibody fragments may be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing antibody, and (d) Fv fragments.

In certain embodiments, It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells. It is contemplated that the antibodies can be prepared in vitro using known methods in synthetic protein chemistry, including those involving crosslinking antibodies. For example, immunotoxins can be constructed using a disulfide exchange reaction or by forming a thioether bond.

For the purposes of the present invention, it should be appreciated that modified antibodies can comprise any type of variable region that provides for the association of the antibody with the polypeptides of a human FZD receptor. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing.

Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies dis-closed herein may comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ACH2 constructs). In some embodiments, the omitted constant region domain will be replaced by a short amino acid spacer (e.g. 10 residues) that provides some of the molecular flexibility typically imparted by the absent constant region.

In certain embodiments, the FZD-binding antibodies provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half-life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques well within the purview of the skilled artisan.

In certain embodiments, a FZD-binding antibody that is an antibody does not have one or more effector functions. For instance, in some embodiments, the antibody has no antibody-dependent cellular cytoxicity (ADCC) activity and/or no complement-dependent cytoxicity (CDC) activity. In certain embodiments, the antibody does not bind to an Fc receptor and/or complement factors. In certain embodiments, the antibody has no effector function.

It will be noted that in certain embodiments, the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic antibody. Cytotoxic antibodies include chemotherapeutic antibodies, growth inhibitory antibodies, toxins (e.g, an enzymatically active toxin of bacterial, fungal, plant, or animal origin, or fragments thereof, radioactive isotopes (i.e., a radioconjugate), etc. Chemotherapeutic antibodies useful in the generation of such immunoconjugates include, for example, methotrexate, adnamicin, doxorubicin, melphalan, mitomycin C, chlorambucil, daunorubicin or other intercalating antibodies. Enzymati-cally active toxins and fragments thereof that can be used include diphtheria A chain, non-binding active fragments of diphtheria toxin, exotoxin A chain, ricin A chain, abrin A chain, modeccin A chain, alpha-sarcin, *Aleurites fordii* pro-teins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, andthetricothecenes. A variety of radionuclides are available for the production of radioconjugated antibodies including 212Bi, 131I, 131In, 90Y, and 186Re. Conjugates of the antibody and cytotoxic antibody are made using a variety of bifunctional protein-coupling antibodies such as N-succinimidyl-3-(2-pyridyldithiol) propionate (SPDP), iminothiolane (IT), bifunctional deriva-tives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

Conjugate antibodies are composed of two covalently joined antibodies. It is contemplated that the antibodies can be prepared in vitro using known methods in synthetic protein chemistry, including those involving crosslinking antibodies. For example, immunotoxins can be constructed using a disulfide exchange reaction or by forming a thio-etherbond. Examples for this purpose include iminothiolate and methyl-4-mercaptobutyrimidate.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form. In certain embodiments, the antibodies are used in nonconjugated form to harness the subject's natural defense mechanisms including complement-dependent cytotoxicity (CDC) and antibody dependent cellular toxicity (ADCC) to eliminate the malignant cells. In some embodiments, the antibodies can be conjugated to radioisotopes, such as 90Y, 125I, 131I, 123I, 111In, 105Rh, 153Sm, 67Cu, 67Ga, 166Ga, 166Ho, 177Lu, 186Re and 188Re using anyone of a number of well-known chelators or direct labeling. In other embodiments, the dis-closed compositions can comprise antibodies coupled to drugs, prodrugs or biological response modifiers such as methotrexate, adriamycin, and lymphokines such as interferon. Still other embodiments of the present invention comprise the use of antibodies conjugated to specific biotoxins such as ricin or diphtheria toxin. In yet other embodiments the modified antibodies can be complexed with other immunologically active ligands (e.g. antibodies or fragments thereof) wherein the resulting molecule binds to both the neoplastic cell and an effector cell such as a T cell. The selection of which conjugated or unconjugated modified antibody to use will depend of the type and stage of cancer, use of adjunct treatment (e.g., chemotherapy or external radiation) and patient condition. It will be appreciated that one skilled in the art could readily make such a selection in view of the teachings herein.

The antibodies of the present invention can be recombinant antibodies, natural antibodies, or synthetic antibodies or fragment thereof, against a human FZD receptor. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a human FZD receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like.

The isolated antibodies described herein can be produced by any suitable method known in the art. Such methods range from direct protein synthetic methods to constructing a DNA sequence encoding isolated polypeptide sequences and expressing those sequences in a suitable trans-formed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof.

In some embodiments a DNA sequence encoding an antibody of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly. Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction map-ping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human frizzled receptors. Recombinant expression vectors are replicable DNA constructs which have synthetic or cDNA-derived DNA fragments encoding a polypeptide chain of an anti-FZD antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as Ml 3 and filamentous single-stranded DNA phages.

Suitable host cells for expression of a FZD-binding polypeptide or antibody (or a FZD protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are known in the art.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells and other cell lines capable of expressing an appropriate vector including, for example, L cells, C127, 3T3, Chinese hamster ovary (CHO), HeLa and BEM cell lines.

In another embodiment, the invention provides a method of producing an antibody comprising culturing the host cell comprising the vector comprising the nucleic acid sequence encoding for the antibodies of the invention under conditions permitting expression of the antibody. Following expression in a host cell maintained in a suitable medium, the polypeptide or peptide to be expressed, such as that encoding the antibodies of the invention, antibody equivalents thereof, maybe isolated from the medium, and purified by methods known in the art. If the polypeptide or peptide is not secreted into the culture medium, the host cells are lysed prior to isolation and purification.

The present invention further provides methods of screening antibodies for efficacy in inhibiting Wnt signaling, for anti-tumor efficacy, and/or efficacy against cancer stem cells. These methods include, but are not limited to, methods comprising comparing the levels of one or more differentiation markers in a first solid tumor that has been exposed to the antibody relative to the levels of the one or more differentiation markers in a second solid tumor that has not been exposed to the antibody. In certain embodiments, these methods include (a) exposing a first solid tumor, but not a second solid tumor, to the antibody; (b) assessing the levels of one or more differentiation markers in the first and second solid tumors; and (c) comparing the levels of the one or more differentiation markers in the first and second solid tumors. In certain embodiments, the antibody is an inhibitor of the canonical Wnt signaling pathway, and/or inhibits binding of one or more human Wnt proteins to one or more human frizzled receptors. In certain embodiments, the antibody is an antibody that specifically binds to one or more human frizzled receptor. In certain embodiments, increased levels of one or more differentiation markers in the first solid tumor relative to the second solid tumor indicates efficacy against solid tumor stem cells. In certain alternative embodiments, decreased levels of one or more differentiation markers (i.e., negative markers for differentiation) in the first solid tumor relative to the second solid tumor indicates efficacy against solid tumor stem cells. In certain embodiments, the solid tumor is a pancreatic tumor. In certain embodiments, the solid tumor is a pancreatic tumor and the one or more differentiation markers may comprise one or more mucins (e.g, Mud 6) and/or chromogranin A (CHGA). In certain alternative embodiments, the solid tumor is a colon tumor. In some embodiments, the solid tumor is a colon tumor and the one or more differentiation markers comprise cytokeratin 7. Other potential differentiation markers for pancreas and colon as well as other tumor types are known to those skilled in the art. The usefulness of potential differentiation markers in a screening method can be readily assessed by one skilled in the art by treating the desired tumor type with one or more of the anti-FZD antibodies disclosed herein such as 1885 and/or 44R24 and then assessing for changes in expression of the marker by the treated tumor relative to control. Non-limiting examples of such methods, can for instance, be found in the specific Examples below.

In certain embodiments, the invention encompasses polynucleotides comprising polynucleotides that encode the antibodies of the invention or antigen-binding portions thereof. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

In certain embodiments, variants of the polynucleotides of the invention can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

The FZD-binding antibodies of the invention are useful in a variety of applications including, but not limited to, therapeutic treatment methods, such as the treatment of cancer. In certain embodiments, the antibodies are useful for inhibiting Wnt signaling (e.g., canonical Wnt signaling), inhibiting tumor growth, inducing differentiation, reducing tumor volume, and/or reducing the tumorigenicity of a tumor. The methods of use may be in vitro, ex vivo, or in vivo methods. In certain embodiments, the FZD-binding antibody or polypeptide or antibody is an antagonist of the one or more human frizzled receptors to which it binds.

In certain embodiments, the FZD-binding antibodies or antagonists are used in the treatment of a disease associated with Wnt signaling activation. In particular embodiments, the disease is a disease dependent upon Wnt signaling. In particular embodiments, the Wnt signaling is canonical Wnt signaling. In certain embodiments, the FZD-binding antibodies or antagonists are used in the treatment of disorders characterized by increased levels of stem cells and/or progenitor cells.

In certain embodiments, the disease treated with the FZD-binding antibody is a cancer. In certain embodiments, the cancer is characterized by Wnt-dependent tumors. In certain embodiments, the cancer is characterized by tumors expressing one or more frizzled receptors to which the FZD-binding antibody binds. In certain embodiments, the cancer is characterized by tumors expressing one or more genes in a Wnt gene signature.

In certain embodiments, the disease treated with the FZD-binding antibody or antagonist is not a cancer. For example, the disease may be a metabolic disorder such as obesity or diabetes. Alternatively, the disease may be a bone disorder such as osteoporosis, osteoarthritis, or rheumatoid arthritis. The disease may also be a kidney disorder, such as a polycystic kidney disease. Alternatively, eye disorders including, but not limited to, macular degeneration and familial exudative vitreoretinopathy may be treated. Cardiovascular disorders, including myocardial infarction, atherosclerosis, and valve disorders, may also be treated. In some embodiments, the disease is a pulmonary disorder such as idiopathic pulmonary arterial hypertension or pulmonary fibrosis. In some embodiments, the disease treated with the FZD-binding antibody is a liver disease, such as cirrhosis or liver fibrosis.

The present invention provides for methods of treating cancer comprising administering a therapeutically effective amount of a FZD-binding antibody to a subject (e.g., a subject in need of treatment). In certain embodiments, the cancer is a cancer selected from the group consisting of colorectal cancer, pancreatic cancer, lung cancer, ovarian cancer, liver cancer, breast cancer, kidney cancer (e.g. Wilms' tumor), prostate cancer, gastrointestinal cancer, melanoma, cervical cancer, bladder cancer, glioblastoma, and head and neck cancer. In certain embodiments, the cancer is pancreatic cancer. In another embodiment, the condition is an ovarian cancer. In another embodiment, the condition is a lung cancer. In another embodiment, the condition is "lung"+"ovary" tumor. In another embodiment, the condition is a tumor metastasized from lung cancer. In another embodiment, the condition is a non-small cell lung cancer (NSCLC). In another embodiment, the condition is an NSCLC-Bev eligible (Avastin). In another embodiment, the condition is an NSCLC-Bev ineligible (Avastin). In another embodiment, the condition is a prostate cancer. In another embodiment, the condition is a tumor metastasized from prostate cancer. In another embodiment, the condition is a benign prostatic hyperplasia. In another embodiment, the condition is a hormone refractory prostate cancer (HRPC In another embodiment, the condition is a bladder cancer. In another embodiment, the condition is a gall bladder cancer. In another embodiment, the condition is a bone cancer. In another embodiment, the condition is a cervical cancer. In another embodiment, the condition is an adrenal cortical cancer. In another embodiment, the condition is an adrenal cancer. In another embodiment, the condition is a retinal cancer. In another embodiment, the condition is a retinoblastoma. In another embodiment, the condition is a gastric cancer. In another embodiment, the condition is aneuroendocrine cancer. In another embodiment, the condition is a bile duct cancer, for example, cholangiocarcinoma. In another embodiment, the condition is a myeloma. In another embodiment, the condition is an androgen-dependent tumor. In another embodiment, the condition is an androgen-independent tumor. In another embodiment, the condition is an acromegaly. In another embodiment, the condition is a synovial sarcoma. In another embodiment, the condition is a diarrhea associated with metastatic carcinoid. In another embodiment, the condition is a vasoactive intestinal peptide secreting tumor. In another embodiment, the condition is a gigantism. In another embodiment, the condition is a psoriasis. In another embodiment, the condition is an atherosclerosis. In another embodiment, the condition is a smooth muscle restenosis of blood vessels. In another embodiment, the condition is an inappropriate microvascular proliferation. In another embodiment, the condition is a neuroblastoma. In another embodiment, the condition is a glioblastoma. In another embodiment, the condition is embryonal (EMB) carcinoma. In another embodiment, the condition is ALV. In another embodiment, the condition is a medulloblastoma. In another embodiment, the condition is ependymoma. In another embodiment, the condition is aHCC/hepatocellular cancer. In another embodiment, the condition is a hepatoblastoma. In another embodiment, the condition is Wilms' cancer. In another embodiment, the condition is Ewing cancer. In another embodiment, the condition is a Rhabdoid. In another embodiment, the condition is leukemia. In another embodiment, the condition is an esophageal. In another embodiment, the condition is a pediatric solid tumor, specifically including Ewing's/PNET. In another embodiment, the condition is an adult solid tumor. In another embodiment, the condition is an osteosarcoma. In another embodiment, the condition is a rhabdomyosarcoma (RMS). In another embodiment, the condition is a soft tissue sarcoma. In another embodiment, the condition is a soft tissue sarcoma including embryonal and alveolar rhabdomyosarcoma, GIST, alveolar soft part sarcoma, and clear cell sarcoma. In another embodiment, the condition is a thymoma. In another embodiment, the condition is a thymic carcinoma. In certain embodiments, the cancer is colorectal cancer. In certain embodiments, the subject is a human.

In some embodiments, the invention provides a method for treating a tumor in a subject comprising the step of administering a therapeutically effective dose of an isolated antibody or antigen-binding portion thereof that binds to a Frizzled7 receptor. The antibody of this method may bind to the cytoplasmic portion of the receptor and, optionally, to the transmembrane portion of the receptor. In one embodiment, the antibody used in this method may be the antibody produced by the hybridoma cell line 288-1. In another embodiment, the antibody used in this method may be the antibody produced by the hybridoma cell line 288-2. In another embodiment, the antibody used in this method may be the antibody produced by the hybridoma cell line 288-5.

A method for treating a tumor in a subject, said method comprising the step of administering a therapeutically effective dose of an isolated antibody or antigen-binding portion thereof to a subject, wherein said isolated antibody binds to a sequence comprising at least a 5 amino acid portion of SEQ ID NO:1, wherein said portion of SEQ ID NO:1 is present on a Frizzled receptor, and wherein said tumor has elevated expression or activity of Frizzled receptors.

In some embodiments, the invention provides a method for treating a tumor in a subject comprising the step of administering a therapeutically effective dose of an isolated antibody or antigen-binding portion thereof that binds to a sequence comprising at least a 5 amino acid portion of SEQ ID NO:1, wherein said portion of SEQ ID NO:1 is present on a frizzled receptor. In one embodiment, the antibody used in this method may be the antibody produced by the hybridoma cell line 288-1. In another embodiment, the antibody used in this method may be the antibody produced by the hybridoma cell line 288-2. In another embodiment, the antibody used in this method may be the antibody produced by the hybridoma cell line 288-5. In one embodiment, treatment with antibody may be upon detection of an abnormal (e.g. high) level of frizzled receptor expression. In another embodiment, treatment with antibody may be upon detection of an abnormal (e.g. high) level of frizzled receptor activity.

In some embodiments, the invention provides a method for treating a tumor in a subject comprising the step of administering a therapeutically effective dose of an isolated antibody or antigen-binding portion thereof that binds to a sequence comprising at least a 5 amino acid portion of SEQ ID NO:2, wherein said portion of SEQ ID NO:2 is present on a frizzled receptor. In one embodiment, the antibody used in this method may be the antibody produced by the hybridoma cell line 288-4. In another embodiment, the antibody used in this method may be the antibody produced by the hybridoma cell line 289-5. In another embodiment, the antibody used in this method may be the antibody produced by the hybridoma cell line number 4. In one embodiment, treatment with antibody may be upon detection of an abnormal (e.g. high) level of frizzled receptor expression. In another embodiment, treatment with antibody may be upon detection of an abnormal (e.g. high) level of frizzled receptor activity.

In some embodiments, the invention provides a method for treating a tumor in a subject comprising the step of administering a therapeutically effective dose of an isolated antibody or antigen-binding portion thereof that binds to a sequence comprising at least a 5 amino acid portion of SEQ ID NO:3, wherein said portion of SEQ ID NO:3 is present on a frizzled receptor. In one embodiment, treatment with antibody may be upon detection of an abnormal (e.g. high) level of frizzled receptor expression. In another embodiment, treatment with antibody may be upon detection of an abnormal (e.g. high) level of frizzled receptor activity.

In some embodiments, the invention provides a method for treating a tumor in a subject comprising the step of administering a therapeutically effective dose of an isolated antibody or antigen-binding portion thereof that binds to a sequence comprising at least a 5 amino acid portion of SEQ ID NO:4, wherein said portion of SEQ ID NO:4 is present on a frizzled receptor. In one embodiment, the antibody used in this method may be the antibody produced by the hybridoma cell line 289-6. In another embodiment, the antibody used in this method may be the antibody produced by the hybridoma cell line 289-18. In another embodiment, the antibody used in this method may be the antibody produced by the hybridoma cell line 289-12. In another embodiment, the antibody used in this method may be the antibody produced by the hybridoma cell line 289-3. In another embodiment, the antibody used in this method may be the antibody produced by the hybridoma cell line number 289-13. In one embodiment, treatment with antibody may be upon detection of an abnormal (e.g. high) level of frizzled receptor expression. In another embodiment, treatment with antibody may be upon detection of an abnormal (e.g. high) level of frizzled receptor activity.

Treatment means any treatment of a disease in a mammal and includes: (1) preventing the disease from occurring in a mammal which may be predisposed to the disease but does not yet experience or display symptoms of the disease; e.g. prevention of the outbreak of the clinical symptoms; (2) inhibiting the disease, e.g., arresting its development; or (3) relieving the disease, e.g., causing regression of the symptoms of the disease.

Effective dosage for the treatment of a disease means that amount which, when administered to a mammal in need thereof, is sufficient to effect treatment, as defined above, for that disease. The method of treatment described herein can be used to treat any suitable mammal, preferably the mammal is a human.

The present invention further provides methods for inhibiting tumor growth using the antibodies or other antibodies described herein. In certain embodiments, the method of inhibiting the tumor growth comprises contacting the cell with a FZD-binding antibody in vitro. For example, an immortalized cell line or a cancer cell line that expresses the targeted FZD(s) is cultured in medium to which is added the antibody or other antibody to inhibit tumor growth. In some embodiments, tumor cells are isolated from a patient sample such as, for example, a tissue biopsy, pleural effusion, or blood sample and cultured in medium to which is added an FZD-binding antibody to inhibit tumor growth.

In some embodiments, the method of inhibiting tumor growth comprises contacting the tumor or tumor cells with the FZD-binding antibody in vivo. In certain embodiments, contacting a tumor or tumor cell with a FZD-binding antibody is undertaken in an animal model. For example, FZD-binding antibodies may be administered to xenografts expressing one or more FZDs that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a FZD-binding antibody to inhibit tumor cell growth. In some embodiments, the FZD-binding antibody is administered at the same time or shortly after introduction of tumorigenic cells into the animal to prevent tumor growth. In some embodiments, the FZD-binding antibody is administered as a therapeutic after the tumorigenic cells have grown to a specified size.

In certain embodiments, the method of inhibiting tumor growth comprises administering to a subject a therapeutically effective amount of a FZD-binding antibody. In certain embodiments, the subject is a human. In certain embodiments, the subject has a tumor or has had a tumor removed. In certain embodiments, the tumor is a tumor in which Wnt signaling is active. In certain embodiment, the Wnt signaling that is active is canonical Wnt signaling. In certain embodiments, the tumor is a Wnt-dependent tumor. For example, in some embodiments, the tumor is sensitive to axin overexpression. In certain embodiments, the tumor does not comprise an inactivating mutation (e.g, a truncating mutation) in the adenomatous polyposis coli (APC) tumor suppressor gene or an activating mutation in the beta-catenin gene. In certain embodiments, the tumor expresses one or more genes in a Wnt gene signature. In certain embodiments, the cancer for which a subject is being treated involves such a tumor.

In certain embodiments, the tumor expresses the one or more human frizzled receptors to which the FZD-binding antibody or antibody binds. In certain embodiments, the tumor overexpresses the human frizzled receptor(s). In certain embodiments, the tumor is a tumor selected from the group consisting of colorectal tumor, pancreatic tumor, lung tumor, ovarian tumor, liver tumor, breast tumor, kidney tumor (e.g Wilms' tumor), prostate tumor, gastrointestinal tumor, melanoma, cervical tumor, bladder tumor, glioblastoma, and head and neck tumor. In certain embodiments, the tumor is a colorectal tumor. In certain embodiments, the tumor is a pancreatic tumor.

The invention also provides a method of inhibiting Wnt signaling in a cell comprising contacting the cell with an effective amount of a FZD-binding antibody. In certain embodiments, the cell is a tumor cell. In certain embodiments, the method is an in vivo method wherein the step of contacting the cell with the antibody comprises administering a therapeutically effective amount of the antibody to the subject. In some alternative embodiments, the method is an in vitro or ex vivo method. In certain embodiments, the Wnt signaling that is inhibited is canonical Wnt signaling. In certain embodiments, the Wnt signaling is signaling by WNT1, WNT2, WNT3, WNT3A, WNT7a, WNT7b, and/or WNT10B. In certain embodiments, the Wnt signaling is signaling by WNT1, WNT3A, WNT7b, and/or WNT 1 OB.

In addition, the invention provides a method of reducing the tumorigenicity of a tumor in a subject, comprising administering a therapeutically effective amount of a FZD-binding antibody to the subject. In certain embodiments, the tumor comprises cancer stem cells. In certain embodiments, the frequency of cancer stem cells in the tumor is reduced by administration of the antibody. Thus, the invention also provides a method of reducing the frequency of cancer stem cells in a tumor, comprising contacting the tumor with an effective amount of a FZD-binding antibody. The invention further provides methods of differentiating tumorigenic cells into non-tumorigenic cells comprising contacting the tumorigenic cells with a FZD-binding antibody (for example, by administering the FZD-binding antibody to a subject that has a tumor comprising the tumorigenic cells or that has had such a tumor removed). In certain embodiments, the tumor is a pancreatic tumor. In certain other embodiments, the tumor is a colon tumor. In certain other embodiments, the tumor is a Wilms' tumor.

The use of the FZD-binding antibodies, or antigen-binding portions thereof, described herein to induce the differentiation of cells, including, but not limited to tumor cells, is also provided. For example, methods of inducing cells to differentiate comprising contacting the cells with an effective amount of a FZD-binding antibody (i.e, an anti-FZD antibody) described herein are envisioned. Methods of inducing cells in a tumor in a subject to differentiate comprising administering a therapeutically effective amount of a FZD-binding antibody, to the subject are also provided. In certain embodiments, the tumor is a pancreatic tumor. In certain other embodiments, the tumor is a colon tumor. In certain other embodiments, the tumor is a Wilms' tumor.

Methods of treating a disease or disorder in a subject, wherein the disease or disorder is associated with Wnt signaling activation and/or is characterized by an increased level of stem cells and/or progenitor cells are further provided. In some embodiments, the treatment methods comprise administering a therapeutically effective amount of the FZD-binding antibody, polypeptide, or antibody to the subject. In certain embodiments, the Wnt signaling is canonical Wnt signaling.

In another embodiment, the invention provides a method for treating a medical condition mediated by elevated expression or activity of Frizzled receptors. In one embodiment, the method comprises the step of administering, to a subject, a therapeutically effective dose of the antibody that binds specifically to SEQ ID NO:1 within FZD7. In one embodiment, the method comprises the step of administering, to a subject, a therapeutically effective dose of the antibody that binds specifically to SEQ ID NO:2 within FZD7 or FZD2. In one embodiment, the method comprises the step of administering, to a subject, a therapeutically effective dose of the antibody that binds specifically to SEQ ID NO:3 within FZD7. In one embodiment, the method comprises the step of administering, to a subject, a therapeutically effective dose of the antibody that binds specifically to SEQ ID NO:4 within FZD7. In another embodiment, the method comprises the step of administering, to a subject, a therapeutically effective dose of the antibody that binds specifically to a transmembrane domain in the FZD7 receptor. In another embodiment, the method comprises the step of administering, to a subject, a therapeutically effective dose of the antibody that binds specifically to a cytoplasmic domain with the FZD7 receptor.

The present invention further provides pharmaceutical compositions comprising one or more of the FZD-binding antibodies described herein. In certain embodiments, the pharmaceutical compositions further comprise a pharmaceutically acceptable vehicle. These pharmaceutical compositions find use in inhibiting tumor growth and treating cancer in human patients.

In certain embodiments, formulations are prepared for storage and use by combining a purified antibody of the present invention with a pharmaceutically acceptable vehicle (e.g. carrier, excipient). Suitable pharmaceutically acceptable vehicles include, but are not limited to, nontoxic buffers such as phosphate, citrate, and other organic acids; salts such as sodium chloride; anti-oxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid resi-dues); proteins such as serum albumin, gelatin, or immunoglobulins; hydrophilic polymers such as polyvinylpyrroli-done; amino acids such as glycine, glutamine, asparagine, histidine, arginine, or lysine; carbohydrates such as monosaccharides, disaccharides, glucose, mannose, or dextrins; chelating antibodies such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g, by inhalation or insufflation of powders or aerosols, including by nebulizer; intratracheal, intranasal, epidermal and transdermal); oral; or parenteral including intravenous, intraarterial, subcutaneous, intraperi-toneal or intramuscular injection or infusion; or intracranial (e.g, intrathecal or intraventricular) administration.

The therapeutic formulation of the antibodies of the invention may be in, certain embodiments, in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid pre-formulation composition containing a homogeneous mixture of a compound of the present invention, or a non-toxic pharmaceutically acceptable salt thereof. The solid preformulation composition is then subdivided into unit dosage forms of the type described above. The tablets, pills, etc of the novel composition can be coated or otherwise compounded to pro-vide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

In certain embodiments, the antibodies may also be entrapped in microcapsules. Such microcapsules are prepared, for example, by coacervation techniques or by interfacial poly-merization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in the art.

In certain embodiments, pharmaceutical formulations include antibodies of the present invention complexed with liposomes. Liposomes with enhanced circulation time are known in the art. In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

In certain embodiments, in addition to administering the FZD-binding antibody, the method or treatment further comprises administering a second anti-cancer antibody (prior to, concurrently with, and/or subsequently to administration of the FZD-binding antibody). Pharmaceutical compositions comprising the FZD-binding antibody and the second anti-cancer antibody are also provided. In selected embodiments, the FZD-binding antibodies will be administered to patients that have previously undergone treatment with the second anti-cancer antibody. In certain other embodiments, the FZD-binding antibody and the second anti-cancer antibody will be administered substantially simultaneously or concurrently. For example, a subject may be given the FZD-binding antibody while undergoing a course of treatment with the second anti-cancer antibody (e.g, chemotherapy). In certain embodiments, the FZD-binding antibody will be administered within 1 year of the treatment with the second anti-cancer antibody. In certain alternative embodiments, the FZD-binding antibody will be administered within 10, 8, 6, 4, or 2 months of any treatment with the second anti-cancer antibody. In certain other embodiments, the FZD-binding antibody will be administered within 4, 3, 2, or 1 week of any treatment with the second anti-cancer antibody. In some embodiments, the FZD-binding antibody will be administered within 5, 4, 3, 2, or 1 days of any treatment with the second anti-cancer antibody. It will further be appreciated that the two antibodies or treatment may be administered to the subject within a matter of hours or minutes (i.e., substantially simultaneously).

Useful classes of anti-cancer antibodies that may be administered in combination with the antibodies of the invention include, for example, antitubulin antibodies, auristatins, DNA minor groove binders, DNA replication inhibitors, alkylating antibodies (e.g, platinum complexes such as cis-platin, mono(platinum), bis (platinum) and tri-nuclear platinum complexes and carboplatin), anthracyclines, antibiotics antifolates, antimetabolites, chemotherapy sensitizers, duocarmycins, etoposides, fluori-nated pyrimidines, ionophores, lexitropsins, nitrosoureas, platinols, performing compounds, purine antimetabolites, puromycins, radiation sensitizers, steroids, taxanes, topoisomerase inhibitors, vinca alkaloids, or the like. In certain embodiments, the second anti-cancer antibody is an antimetabolite, an antimitotic, a topoisomerase inhibitor, or an angiogenesis inhibitor.

Anticancer antibodies that may be administered in combination with the FZD-binding antibodies include chemotherapeutic agents. Thus, in some embodiments, the method or treatment involves the combined administration of an antibody of the present invention and a chemotherapeutic agent or cocktail of multiple different chemotherapeutic agents. Treatment with an antibody can occur prior to, concurrently with, or subsequent to administration of chemotherapies. Chemotherapies contemplated by the invention include chemical substances or drugs which are known in the art and are commercially available, such as Gemcitabine, Irinotecan, Doxorubicin, 5-Fluorouracil, Cytosine arabinoside ("Ara-C"), Cyclophosphamide, Thiotepa, Busulfan, Cytoxin, TAXOL, Methotrexate, Cisplatin, Melphalan, Vinblastine and Carboplatin. Combined administration can include co-administration, either in a single pharmaceutical formulation or using separate formulations, or consecutive administration in either order but generally within a time period such that all active antibodies can exert their biological activities simultaneously.

Chemotherapeutic agents useful in the instant invention also include, but are not limited to, alkylating agents such as thiotepa and cyclosphosphamide (CY-TOXAN); alkyl sulfonates such as busulfan, improsulfanand piposulfan; aziridines such as benzodopa, carboquone, meturedopa, and uredopa; ethylenimines and methy-lamelamines including altretamine, triethylenemelamine, tri-etylenephosphoramide, triethylenethiophosphaoramide and trimethylolomelamime nitrogen mustards such as chloram-bucil, chlomaphazine, cholophosphamide, estramustine, ifosfamide, mechlorethamine, mechlorethamine oxide hydrochloride, melphalan, novembichin, phenesterine, pred-nimustine, trofosfamide, uracil mustard; nitrosureas such as carmustine, chlorozotocin, fotemustine, lomustine, nimus-tine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dro-mostanolone propionate, epitiostanol, mepitiostane, testolactone; anti-adrenals such as aminoglutethimide, mitotane, trilostane; folic acid replenisher such as frolinic acid; acegla-tone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL, Bristol-Myers Squibb Oncology, Princeton, N.J.) and doxetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Chemotherapeutic agents also include anti-hormonal antibodies that act to regulate or inhibit hormone action on tumors such as anti-estrogens including for example tamoxifen, raloxifene, aromatase inhibiting 4(5)-imidazoles, 4-hydroxy tamoxifen, trioxifene, keoxifene, LY117018, onapristone, and toremifene (Fareston); and anti-androgens such as flutamide, nilutamide, bicalutamide, leu-prolide, and goserelin; and pharmaceutically acceptable salts, acids or derivatives of any of the above. [0282] In certain embodiments, the chemotherapeutic agentis a topoisomerase inhibitor. Topoi-somerase inhibitors include, but are not limited to, doxorubicin HCL, daunorubicin citrate, mitoxantrone HCL, actino-mycin D, etoposide, Topotecan HCL, teniposide (VM-26), and irinotecan. In certain embodiments, the second anticancer agent is irinotecan. In certain embodiments, the tumor to be treated is a colorectal tumor and the second anticancer agent is a topoisomerase inhibitor, such as irinotecan. In certain embodiments, the chemotherapeutic agent is an anti-metabolite. Anti-metabolites include, but are not limited to, gemcitabine, fluorouracil, capecitabine, methotrexate sodium, ralitrexed, Pemetrexed, tegafur, cytosine arabinoside, THIOGUANINE (GlaxoSmithKline), 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second anticancer agent is gemcitabine. In certain embodiments, the tumor to be treated is a pancreatic tumor and the second anticancer agent is an anti-metabolite (e.g., gemcitabine). In certain embodiments, the chemotherapeutic agent is an antimitotic antibody, including, but not limited to, antibodies that bind tubulin. By way of non-limiting example, the agent comprises a taxane. In certain embodiments, the agent comprises paclitaxel or docetaxel, or a pharmaceutically acceptable salt, acid, or derivative of paclitaxel or docetaxel. In certain embodiments, the antibody is paclitaxel (TAXOL), docetaxel (TAXOTERE), albumin-bound paclitaxel (e.g., ABRAXANE), DHA-paclitaxel, or PG-paclitaxel. In certain alternative embodiments, the antimitotic agent comprises a vinka alkaloid, such as vincristine, binblastine, vinorelbine, or vindesine, or pharmaceutically acceptable salts, acids, or derivatives thereof. In some embodiments, the antimitotic agent is an inhibitor of Eg5 kinesin or an inhibitor of a mitotic kinase such as Aurora A or Plk1. In certain embodiments where the chemotherapeutic agent administered in combination with the FZD-binding antibody or polypeptide or antibody comprises an antimitotic agent.

In certain embodiments, the treatment of cancer or a tumor in a subject involves the combined administration of an antibody of the present invention and radiation therapy. Treatment with the antibody can occur prior to, concurrently with, or subsequent to administration of radiation therapy.

In some embodiments, the treatment can involve the combined administration of antibodies of the present invention with other antibodies against additional tumor-associated antigens including, but not limited to, antibodies that bind to EGFR, ErbB2, HER2, DLL4, Notch and/or VEGF. In certain embodiments, the second anti-cancer antibody is an antibody that is an angiogenesis inhibitor (e.g, an anti-VEGF antibody). In certain embodiments, the second anti-cancer antibody is an inhibitor of Notch signaling. In certain embodiments, the second anti-cancer antibody is AVASTIN (Bevaci-zumab), Herceptin (Trastuzumab), VECTIBIX (Panitu-mumab), or Erbitux (Cetuximab). Combined administration can include co-administration, either in a single pharmaceutical formulation or using separate formulations, or consecutive administration in either order but generally within a time period such that all active antibodies can exert their biological activities simultaneously.

Furthermore, treatment of cancer or a tumor in a subject can include administration of one or more cytokines (e.g, lymphokines, interleukins, tumor necrosis factors, and/or growth factors) or can be accompanied by surgical removal of cancer cells or any other therapy deemed necessary by a treating physician.

For the treatment of the disease, the appropriate dosage of an of the present invention depends on the type of disease to be treated, the severity and course of the disease, the responsiveness of the disease, whether the antibody or antibody is administered for therapeutic or preventative purposes, previous therapy, or patient's clinical history. The antibody or antibody can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or antibody. In certain embodiments, dosage is from 0.01 mg to 100 mg/kg of body weight, and can be given once or more daily, weekly, monthly or yearly. In certain embodiments, the FZD-binding antibody is given once every two weeks or once every three weeks. In certain embodiments, the dosage of the antibody or other FZD-binding antibody is from about 0.1 mg to about 20 mg/kg of body weight.

The present invention provides kits that comprise the antibodies described herein and that can be used to perform the methods described herein. In certain embodiments, a kit comprises at least one purified antibody against one or more human frizzled receptors in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies or antibodies of the present invention can be readily incorporated into one of the established kit formats which are well known in the art.

Further provided are kits comprising a FZD-binding antibody as well as a second anti-cancer agent. In certain embodiments, the second anti-cancer agent is a chemotherapeutic agent. In certain embodiments, the second anti-cancer agent is an angiogenesis inhibitor. In certain embodiments, the second anti-cancer agent is an inhibitor of Notch signaling (e.g, an anti-DLL4 or anti-Notch antibody).

In another embodiment, the invention provides a method of diagnosing a medical condition mediated by elevated expression or activity of frizzled receptors. The method comprises the steps of obtaining a biological sample from the subject; and testing the biological sample for a frizzled receptor with an antibody of the invention. Methods for testing a reactivity of a biological sample with antibodies are well known in the art. Examples of testing methods include, but are not limited to, enzyme-linked immunosorbant assay (ELISA), immunocytochemistry, and immunoprecipitation.

In another embodiment, the invention provides a method of diagnosing a medical condition mediated by elevated expression or activity of the frizzled 7 receptor. The method comprises the steps of obtaining a biological sample from the subject; and testing the biological sample for a frizzled 7 receptor with an antibody of the invention.

In certain embodiment, the invention provides a method of detecting a tumor in a subject. The method comprised the steps of obtaining a biological sample from the subject and testing the biological sample for frizzled 7 by an isolated antibody of the invention or antigen-binding portion thereof that binds to a frizzled 7 receptor. The antibody may bind to the cytoplasmic portion and optionally, the transmembrane portion of the receptor. In one embodiment, the presence of a tumor is determined by assessing the level of frizzled 7 expression in the obtained biological sample. If it is abnormal (e.g., high), this may indicate a malignancy. In another embodiment, the presence of a tumor is determined by assessing the level of activity of frizzled 7 in the obtained biological sample. If it is abnormal (e.g., high), this may indicate a malignancy.

In another embodiment, a method of detecting a tumor in a subject. Comprises the steps of obtaining a biological sample from the subject; and testing the biological sample for a Frizzled receptor by. an isolated antibody or antigen-binding portion thereof that binds to a sequence comprising at least a 5 amino acid portion of SEQ ID NO:1, wherein said portion of SEQ ID NO:1 is present on the Frizzled receptor. In one embodiment, the presence of a tumor is determined by assessing the level of a frizzled receptor expression in the obtained biological sample. If it is abnormal (e.g., high), this may indicate a malignancy. In another embodiment, the presence of a tumor is determined by assessing the level of activity of a frizzled receptor in the obtained biological sample. If it is abnormal (e.g., high), this may indicate a malignancy. In one embodiment the antibody used in this method may be the antibody produced by the hybridoma cell line 288-1. In another embodiment the antibody used in this method may be the antibody produced by the hybridoma cell line 288-2. In another embodiment the antibody used in this method may be the antibody produced by the hybridoma cell line 288-3. In another embodiment the antibody used in this method may be the antibody produced by the hybridoma cell line 288-5.

In another embodiment, a method of detecting a tumor in a subject. Comprises the steps of obtaining a biological sample from the subject; and testing the biological sample for a Frizzled receptor by an isolated antibody or antigen-binding portion thereof that binds to a sequence comprising at least a 5 amino acid portion of SEQ ID NO:2, wherein said portion of SEQ ID NO:2 is present on the Frizzled receptor. In one embodiment, the presence of a tumor is determined by assessing the level of a frizzled receptor expression in the obtained biological sample. If it is abnormal (e.g., high), this may indicate a malignancy. In another embodiment, the presence of a tumor is determined by assessing the level of activity of a frizzled receptor in the obtained biological sample. If it is abnormal (e.g., high), this may indicate a malignancy. In one embodiment the antibody used in this method may be the antibody produced by the hybridoma cell line 288-4. In another embodiment the antibody used in this method may be the antibody produced by the hybridoma cell line 289-5. In another embodiment the antibody used in this method may be the antibody produced by the hybridoma cell line number 4.

In another embodiment, a method of detecting a tumor in a subject. Comprises the steps of obtaining a biological sample from the subject; and testing the biological sample for a Frizzled receptor by an isolated antibody or antigen-binding portion thereof that binds to a sequence comprising at least a 5 amino acid portion of SEQ ID NO:3, wherein said portion of SEQ ID NO:3 is present on the Frizzled receptor. In one embodiment, the presence of a tumor is determined by assessing the level of a frizzled receptor expression in the obtained biological sample. If it is abnormal (e.g., high), this may indicate a malignancy. In another embodiment, the presence of a tumor is determined by assessing the level of activity of a frizzled receptor in the obtained biological sample. If it is abnormal (e.g., high), this may indicate a malignancy.

In another embodiment, a method of detecting a tumor in a subject. Comprises the steps of obtaining a biological sample from the subject; and testing the biological sample for a Frizzled receptor by an isolated antibody or antigen-binding portion thereof that binds to a sequence comprising at least a 5 amino acid portion of SEQ ID NO:4, wherein said portion of SEQ ID NO:4 is present on the Frizzled receptor. In one embodiment, the presence of a tumor is determined by assessing the level of a frizzled receptor expression in the obtained biological sample. If it is abnormal (e.g., high), this may indicate a malignancy. In another embodiment, the presence of a tumor is determined by assessing the level of activity of a frizzled receptor in the obtained biological sample. If it is abnormal (e.g., high), this may indicate a malignancy. In one embodiment the antibody used in this method may be the antibody produced by the hybridoma cell line 289-6. In another embodiment the antibody used in this method may be the antibody produced by the hybridoma cell line 289-18. In another embodiment the antibody used in this method may be the antibody produced by the hybridoma cell line 289-12. In another embodiment the antibody used in this method may be the antibody produced by the hybridoma cell line 289-3. In another embodiment the antibody used in this method may be the antibody produced by the hybridoma cell line number 289-13.

The biological sample used in the methods described herein is a body fluid that is tested by methods of the present invention is, in another embodiment, a cerebrospinal fluid (CSF). In another embodiment, the body fluid is plasma. In another embodiment, the body fluid is any other type of fluid known in the art. Each possibility represents a separate embodiment of the present invention. In another embodiment, the biological sample is amniotic fluids, blood, sera, saliva, or their combination. In another embodiment the biological sample is a tissue biopsy. In another embodiment the biological sample is obtained from stool or urine or any other excretion (e.g. perspiration).

EXAMPLES

Example 1: Selection of Epitopes for FZD7 Monoclonal Antibody Generation

Frizzled family receptors share a high level of homology. To generate monoclonal antibodies which are specific for FZD7, non-overlapping sequences between FZD7 and a different Frizzled receptor-FZD2 were identified.

Figure 1A:
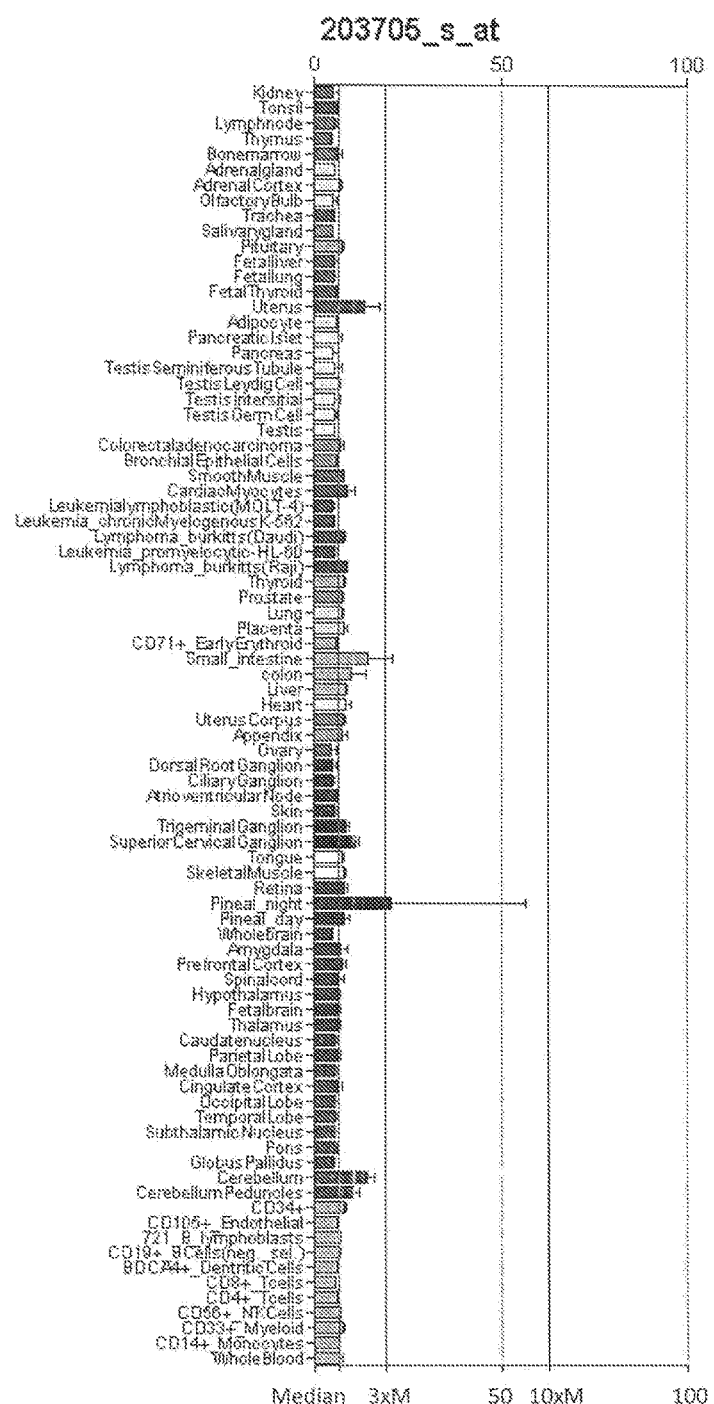
FIG. 1A shows a tissue specificity comparison between FZD7 (left) and FZD2 (right).
Figure 1A:
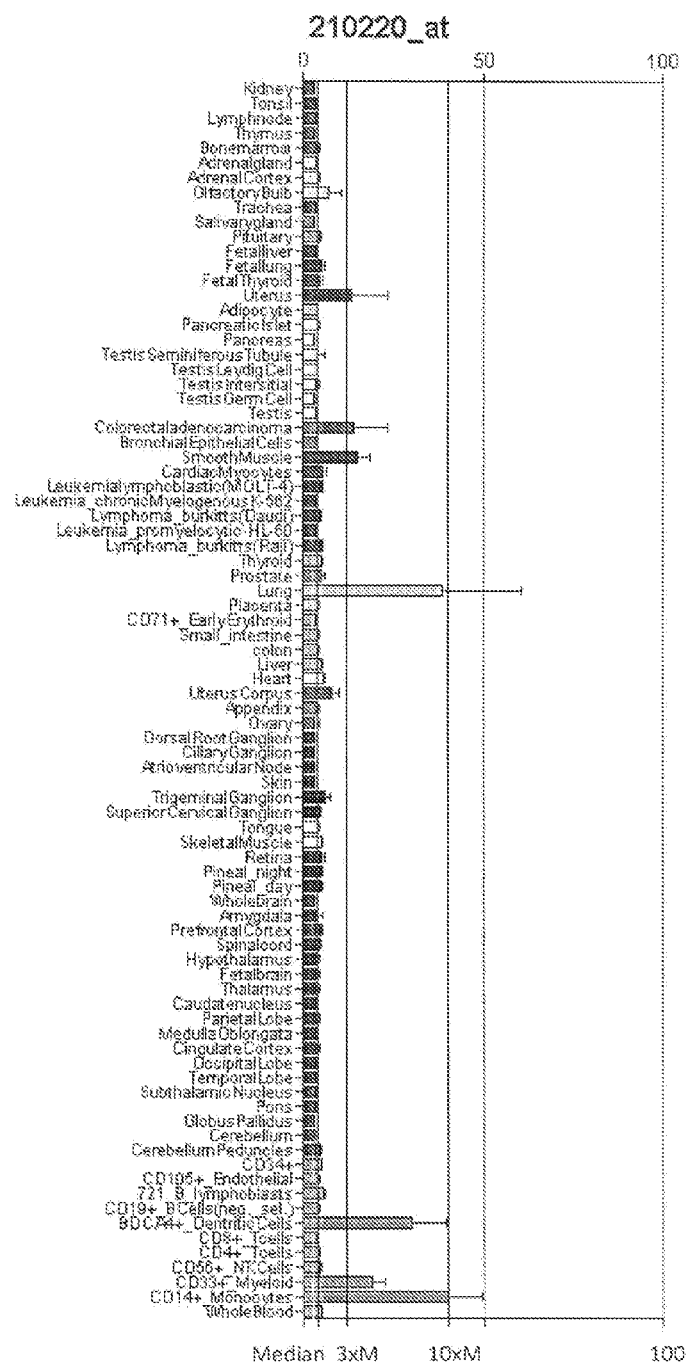
Figure 1B:
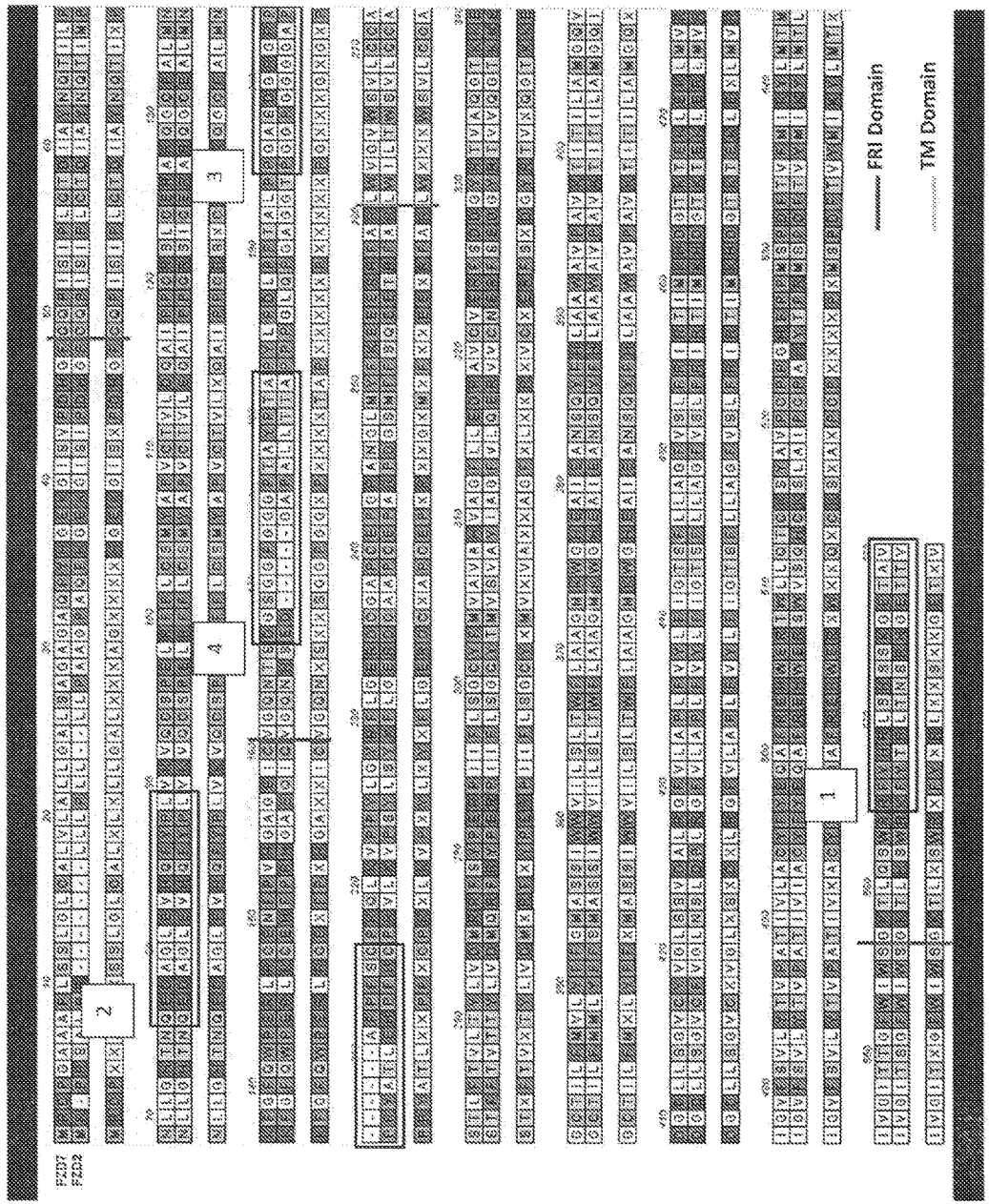
FIG. 1B shows a comparison of the 10 cysteine residues typical of the cysteine-rich extracellular domain of Fz family members between the human FZD2 and human FZD7. 95% (142/150) homology is shown. Black rectangles indicate selected epitope locations. Adjacent squares indicate the epitope's corresponding SEQ ID NO: (for example, the square with the number "1" in it labels the rectangle containing the sequence which is SEQ ID NO: 1).

The expression of the FZD2 and FZD7 genes appears to be developmentally regulated, with high levels of expression in fetal kidney and lung and in adult colon and ovary (FIG. 1A). FZD7 and FZD2 are highly homologous transmembrane proteins, especially in the ligand binding domain (FIG. 1B).

Materials and Methods

Epitope Mapping: A peptide scanning method was used for epitope mapping. This technique uses a library of many short peptide sequences of equal length of overlapping segments from a target protein and tests for their ability to bind the antibody of interest. The short overlapping peptides were designed for the desired sequenced with over hanged edges and additional external areas.

Vaccination:

Peptide(s) corresponding to sequences specific to FZD7 from 4 different areas were used for immunization. For immunization, the peptides were conjugated to KLH using Maleimide Activated BSA/KLH conjugation kit (Sigma, MBK-1). BALB/c mice were immunized and boosted.

Hybridoma Generation:

Spleens were harvested from immunized mice and cells isolated. Cells were fused with mouse myeloma cells (NS-1). Hybridoma supernatant was screened for peptide-specific antibodies by ELISA.

Antibody Purification and Screening:

The hybridomas were grown in bioreactors and the antibodies were purified from the culture supernatant using Protein A agarose columns. Screening for FZD7-specific antibodies was done by ELISA on peptide conjugated BSA and is done by the following methods:

a. ELISA on CHO cells stably expressing full length FZD7 and fixed on ELIS plates.

b. Western blotting using cell extracts of CHO cells stably expressing full length FZD7.

Clones that were positive by the 3 methods above were further assayed and validated for selectivity and efficacy.

ELISA:

BSA conjugates of the screened peptides were used, and peptide positive clones were further screened by Western blotting on cell extracts. The isotype was determined by ELISA using Mouse Monoclonal Antibody Isotyping Reantibodies (Sigma ISO-2).

Results

Towards the goal of generating FZD7 specific monoclonal antibodies, epitope mapping of the FZD7 protein was performed and generated four epitopes including those of the C- and N-terminus as well as non-overlapping sequences with FZD2 (FIG. 1B). The amino acid sequences of these four epitopes are embodied in SEQ ID NOs: 1-4. These FZD7 sequences share a 56%, 100%, 40% and 25% homology with FZD2, respectively. Epitopes were injected into mice to generate hybridomas. In addition, a FZD7 construct was cloned, which was overexpressed in CHO cells for ELISA-based screening of hybridoma clones. Moreover, a secreted FZD7 vector was cloned that included FLAG and MYC-tag. This approach enabled further purification of the MAb's generated via specific binding to secreted FZD7 on a FLAG/MYC column. Therefore, the sequenced peptides that have been selected can be tested for MAb specificity and to the degree for which they are homologous, with FZD2.

Overall, from the hybridomas generated, twenty clones were chosen for in-vitro studies. The selected clones, were those that were positive in ELISA testing for their respective specific antigen (peptide). Table 1 shows the selected hybridomas and the specificity of the monoclonal antibody they produce. Ten (10) additional hybridomas tested did not show antigen specificity in ELISA assays.

TABLE 1

| Clone Number | Antigen Specificity |
|---|---|
| 288-1[1] | RFYHRLSHSSKGETAV (SEQ ID NO: 1) |
| 288-2 | RFYHRLSHSSKGETAV (SEQ ID NO: 1) |
| 288-3 | RFYHRLSHSSKGETAV (SEQ ID NO: 1) |
| 288-5 | RFYHRLSHSSKGETAV (SEQ ID NO: 1) |
| 289-6 | DGSGGPGGGPTAYPTA (SEQ ID NO: 4) |
| 289-12 | DGSGGPGGGPTAYPTA (SEQ ID NO: 4) |
| 289-18 | DGSGGPGGGPTAYPTA (SEQ ID NO: 4) |

[1]Being deposited with ATCC (an International Depository Authority) for the Purposes of Patent Procedure. ATCC Patent Depository 10801 University Blvd. Manassas, VA 20110

Conclusions

Hybridomas producing monoclonal antibodies which are specific for four different epitopes on the Frizzled 7 receptor have been produced. The likelihood of specificity of these antibodies to FZD7 is inversely related to the homology of the epitope sequences between FZD7 and FZD2.

Example 2: Effect of FZD7 Monoclonal Antibodies on Malignant Cell Proliferation

FZD7 monoclonal antibodies generated as described in Example 1 were evaluated for their ability to inhibit proliferation of both primary malignant tissue and malignant cell lines.

Materials and Methods

MTS Assay:

Cells were seeded on a 96 well plates in triplicates. After 24 hours cells were treated with the desired antibody at increasing concentrations for 48 hours and evaluated by the CellTiter 96® AQueous Non-Radioactive Cell Proliferation Assay (MTS) kit (Promega).

Results

Figure 2:
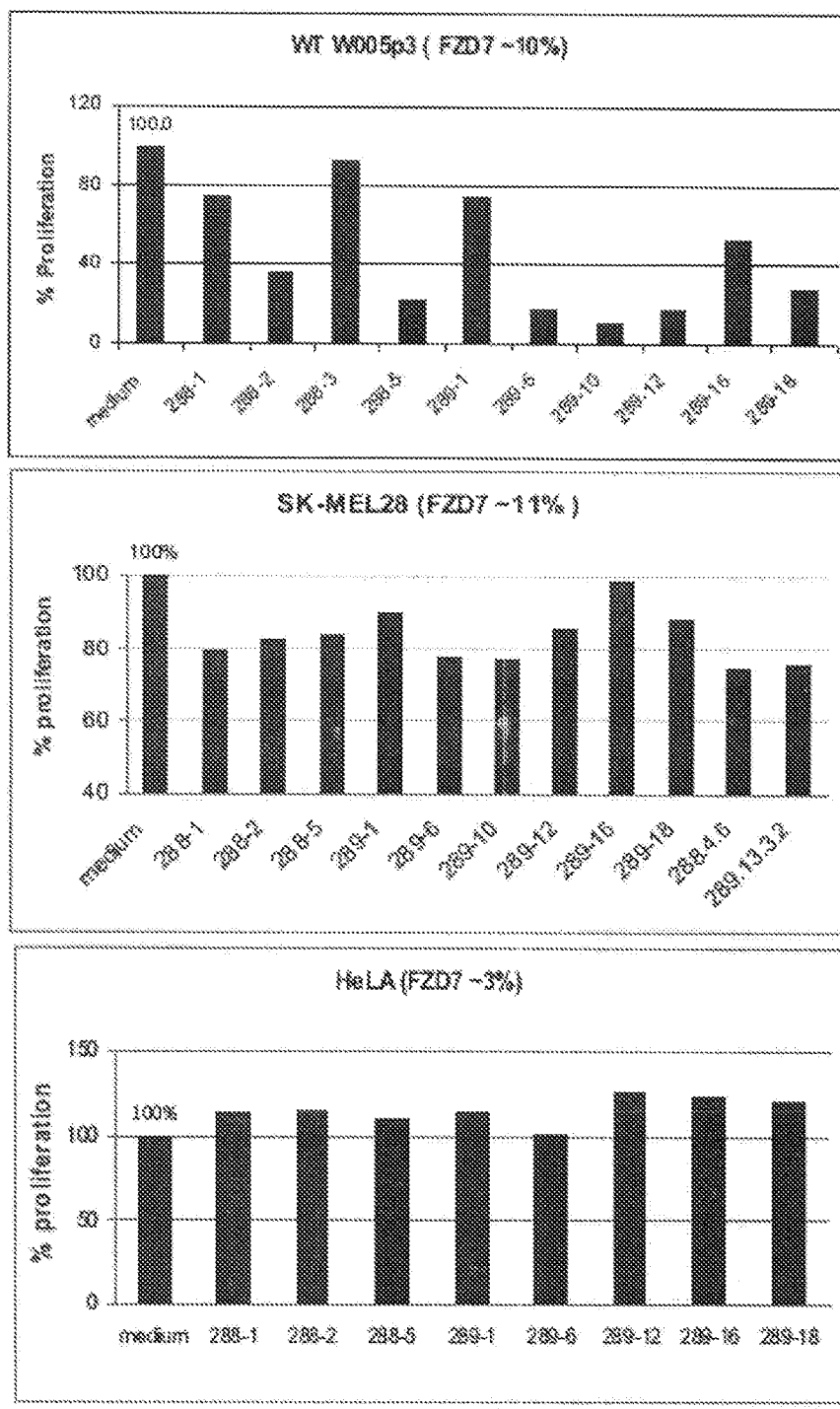
FIG. 2 shows inhibition of malignant cell proliferation by FZD7-specific monoclonal antibodies produced by hybridoma clones generated with selected epitopes. Numbers indicate the hybridoma clone from which an antibody was taken (for example, 288-1 indicates a monoclonal antibody generated by hybridoma clone 288-1). Wilms' Tumor cells (W005) were seeded in 96-well plates and were incubated with antibodies for 48 hours and then were assayed by MTS (cell proliferation assay). Same was done in melanoma cell line cells (SK-MEL28), Wilms Tumor cells (WT): and in HeLa cervical cancer cells. FZD7 expression levels for the Wilms' Tumor cells (WT), SK-MEL-28 cells and HeLA cells are 10%, 11% and 3% respectively.
Figure 3:
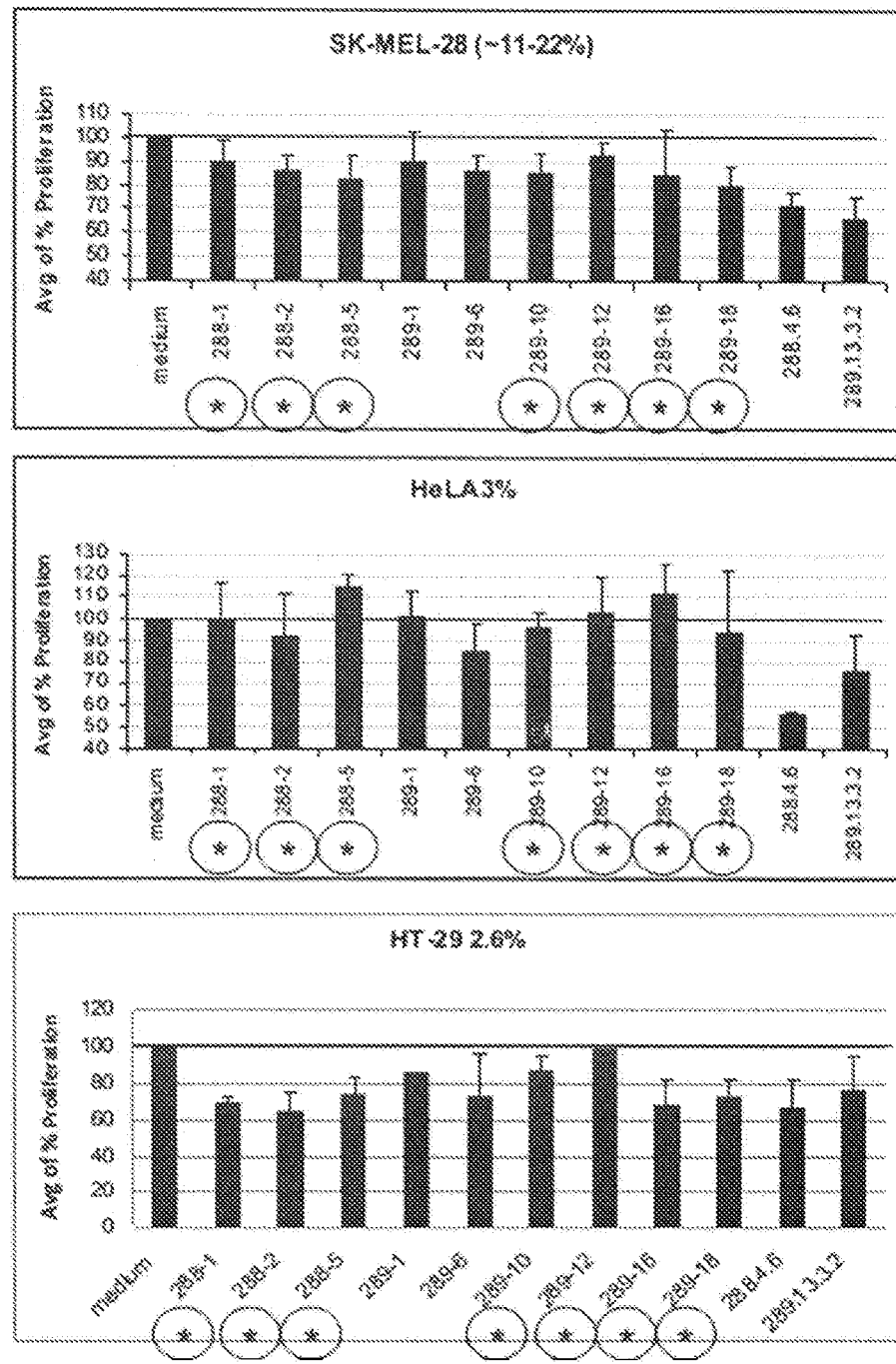
FIG. 3 shows inhibition of malignant cell proliferation by FZD7-specific antibodies from selected hybridoma clones. SK-MEL-28 melanoma cells were seeded in 96 well plates. Cells were incubated with antibodies from the indicated clones for 48 hours and then were assayed by MTS (cell proliferation assay). Same was done in HeLa and in HT-29 colorectal adenocarcinoma cells. FZD7 expression levels are indicated for SK-MEL-28 (11-22%), HeLA (3%) and HT-29 (2.6%). The circled stars indicate the clones shown to be effective. (n=5)

FZD7 monoclonal antibodies were assayed for their ability to inhibit proliferation of malignant cells of different FZD7 expression levels. The analysis was performed on the following cell types: primary Wilms' tumor cells, melanoma (SK-MEL-28), colon (HT29), glioblastoma (U87) and a negative control HeLa cells (express low levels of FZD7). FACS analysis was used to determine FZD7 levels in each of the tumor types: approximately 10% for Wilms' tumor, 11% for melanoma, 2.6% for colon cancer and 3% for HeLa cells. The MTS assay was used to assess inhibition of malignant cell proliferation. Data are shown in FIG. 2 on Wilms' tumor (WT), melanoma (SK-MEL-28) and cervical cancer (HeLA) cells and in FIG. 3 on melanoma (SK-MEL-28), cervical cancer (HeLA) and colon cancer (HT-29). Note how inhibition is associated with expression level of frizzled 7.

Conclusions

Hybridoma clones were isolated that produce monoclonal antibodies that show beneficial effects in vitro on the inhibition of proliferation of tumor cells. Frizzled7-expressing tumor cell are especially vulnerable to the activity of the antibodies.

Example 3: Effect of FZD7 Monoclonal Antibodies on Malignant Cell Viability

FZD7 monoclonal antibodies generated as described in Example 1 were evaluated for their ability to induce cell death of both primary malignant tissue and malignant cell lines.

Materials and Methods

MTS Assay:

Cells were seeded on a 96 well plates in triplicates. After 24 hours cells were treated with the desired antibody at increasing concentrations for 48 hours and evaluated by the CellTiter 96® AQueous Non-Radioactive Cell Proliferation Assay (MTS) kit (Promega).

Results

FZD7 monoclonal antibodies were assayed for their ability to kill malignant cells of different FZD7 expression levels. First, killing of primary tumor malignant cells by the different FZD7-specific monoclonal antibodies was evaluated. As a source of primary tumor, Wilms' tumor, which has an approximately 10% expression level of FZD7, was used. Antibodies were the FZD7-specific monoclonal antibodies produced by hybridoma clones generated with selected epitopes as described in Example 1. After 48 hours of incubation with antibodies cells were assayed for viability by trypan blue. Percent of live cells from total cells for each monoclonal Ab used is shown in FIG. 4A. Next, killing of SK-MEL-28 and SK-MEL-29 melanoma cells by the FZD7-specific monoclonal antibodies was evaluated. SK-MEL-28 and SK-MEL-cells were seeded in 96-well plates and were incubated with antibodies for 48 hours and then were assayed for viability by trypan blue. Absolute cell counts of live cells are shown in FIG. 4B. Finally, microimages of SK-MEL-28 cells after treatment with one of the monoclonal antibodies (clone 288-2) or without antibody treatment were obtained. Cell death and was readily visible in treated cells (FIG. 4C).

Example 4: Determination of Optimal Concentration of FZD7 Monoclonal Antibodies for Induction of Tumor Inhibition FZD7 monoclonal antibodies generated as described in Example 1 were evaluated at different concentrations for their ability to inhibit of malignant cell proliferation.

Materials and Methods

MTS Assay:

Cells were seeded on a 96 well plates in triplicates. After 24 hours cells were treated with the desired antibody at increasing concentrations for 48 hours and evaluated by the CellTiter 96® AQueous Non-Radioactive Cell Proliferation Assay (MTS) kit (Promega).

Results

The dose response in terms of inhibition of cell proliferation upon exposure to different concentrations of anti FZD7 monoclonal antibody produced in clones 288-1 and 288-5 was determined. The response of a high FZD7-expressing malignant tissue (SK-MEL28, melanoma cells) was compared with that of a low FZD7-expressing malignant tissue (HeLa, cervical cancer cells). Cells were exposed to antibody for 48 h and proliferation was assessed by the MTS assay and compared to cells not treated with antibody. Proliferation was inhibited in the presence of either FZD7 antibody in high FZD7 expressing cells but not in low expressing cells such as HeLa (FIG. 5A). Optimal inhibition of proliferation was observed at an antibody concentration of about 5 ug/ml. Data shown is normalized to control untreated cells for each cell line. FIG. 5B shows the data from FIG. 5A in a way which highlights the effect the culturing density of SK-MEL28 melanoma cells has on the level of inhibition of proliferation by 5 ug/ml of the FZD7 monoclonal Ab produced by hybridoma clones 288-1 and 288-5. It is observed that at this Ab concentration, inhibition is greater when a 4000 cell/well density is employed in the case of 288-5 and similar in the case of 288-1.

Conclusions

Optimal concentration of monoclonal antibodies isolated from hybridoma clones for inducing cell death in tumor cells was determined. This is shown both in cell lines and in primary tumors.

Example 5: Effect of FZD7 Monoclonal Antibodies on Malignant Cell Wnt Signaling

FZD7 monoclonal antibodies generated as described in Example 1 were evaluated for their ability to inhibit Wnt signaling of malignant cells.

Results:

Western blot analysis was performed for active β-Catenin (millipore 05665) in HeLa and SK-MEL28 cells after 48 h treatment with 288-1 Ab at the indicated concentration (FIG. 6). β-catenin inhibition by the 288-1 FZD7 mAb is demonstrated. Also, in FIG. 7B the expression of WNT targeted genes was evaluated using RQ PCR in Untreated & antibody treated Wilms tumor & HeLa cells (FIG. 7B).

Conclusion

FZD7 monoclonal antibodies generated as described in Example 1 were able to inhibit Wnt signaling upon binding the receptor. This inhibition is associated with malignant cell death as demonstrated in Example 3 and apotosis as demonstrated in Example 6 below.

Example 6: Induction of Apoptosis in Malignant Cells by FZD7 Monoclonal Antibodies The ability of antibodies of the invention to induce apoptosis in malignant cells was determined.
Results
Apoptosis of malignant cells treated with antibodies of the invention was observed (FIG. 7A). Specifically, Flow cytometry of APC conjugated Annexin V binding to Melanoma and HeLa cells is shown. Levels of Annexin staining are compared in the presence of the monoclonal antibody produced by hybridoma 288-1 at different concentrations or without antibody (FIG. 7A).

Conclusion

The ability of antibodies of the invention to induce apoptosis in malignant cells was observed.

Example 7: Inhibition of Cell Proliferation by FZD7 Specific Monoclonal Antibodies Secreted by Hybridoma Clones The ability of specific monoclonal antibodies of the invention to inhibit proliferation in cancer cells was determined. Cells were seeded in 96 well plates. Melanoma cell line (SK-MEL28), Colon cancer cell line (HT-29), and primary Wilms' tumor (WT) cells were incubated with antibodies from the indicated clones for 48 hours and then were assayed by the cell proliferation assay (PROMEGA).
Results:
FIG. 8 depicts the arrangement of the FZD7 polypeptide within the plasma membrane and identifies the locations of peptides 1-4. The homology between these peptides and other members of the Frizzled family of receptors is shown in the table below, wherein "Homology" indicates the number of amino acid residues that are similar between the peptide and the antigen area of the indicated FZD receptor:

| Frizzled receptor | Peptide 1 Homology | % | Peptide 2 Homology | % | Peptide 3 Homology | % | Peptide 4 Homology | % |
|---|---|---|---|---|---|---|---|---|
| FZD1 | 14 | 100 | 6 | 38 | 4 | 25 | 9 | 56 |
| FZD2 | 14 | 100 | 8 | 50 | 4 | 25 | 9 | 56 |
| FZD3 | 5 | 36 | 1 | 6 | 1 | 6 | 5 | 31 |
| FZD4 | 7 | 50 | 2 | 13 | 4 | 25 | 8 | 50 |
| FZD5 | 11 | 79 | 4 | 25 | 3 | 19 | 6 | 38 |
| FZD6 | 6 | 43 | 3 | 19 | 1 | 6 | 8 | 50 |
| FZD7 | 14 | 100 | 16 | 100 | 16 | 100 | 16 | 100 |
| FZD8 | 11 | 79 | 6 | 38 | 3 | 19 | 5 | 31 |
| FZD9 | 6 | 43 | 6 | 38 | 4 | 25 | 3 | 19 |
| FZD10 | 6 | 43 | 2 | 13 | 5 | 31 | 3 | 19 |
| FZD11 (SMO) (SEQ ID NO: 15) | 2 | 14 | 1 | 6 | 2 | 13 | 4 | 25 |

FIG. 9 shows the inhibition of cell proliferation by FZD7 specific monoclonal antibodies secreted by hybridomas in relationship to percent proliferation of control. The numbers indicate the hybridoma clone from which the antibody was taken and "*" indicates the effective clones to be 288-1, 288-2, 288-5, 289-10, 289-16 and 289-13. The classification of the effective clones by peptide matching and isotype is presented in the table below:

| Anti FZD7-Ab | Clone Isotype | Peptide |
|---|---|---|
| 288-5 | IgG1 | 4 |
| 288-1 | IgG2b | 4 |
| 289-13 | IgG1 | 3 |
| 288-2 | UD | 4 |
| 289-10 | UD | UD |
| 289-16 | UD | UD |

Example 8: Anti FZD7 Antibody 288-1 Specificity—Specificity of Anti-FZD7 Monoclonal Antibody 288-1 for C-Terminus Antigen of FZD7 Receptor Protein A protein immunoprecipitation assay was used to validate specificity of monoclonal antibody (MAb) MAb-288.1, MAb-288.5, and MAb-289.13 binding to the FZD7 receptor in SK-MEL28 cell lysate.
Methods:
For immunization mice were injected with both peptide 1 and peptide 4. In order to determine antibody specificity a blocking assay was performed. Briefly, cells' lysate was incubated with the peptide to block the binding antigen, then a Western Blot analysis was performed using the indicated anti-FZD7 Ab. FZD7 Input (total cell lysate), and FZD7 bound fractions were separated by 10% SDS-PAGE followed by Western Blotting and detected using an anti-FZD7 antibodies. Following an overnight incubation with the different MAbs, proteins were immune-precipitated using protein A agarose beads. Mouse IgG served as negative control. A peptide block assay was performed to verify the specificity of MAb-288.1 to antigen C of the FZD7 receptor. MAb-288.1 was incubated with the immunizing peptide for 4 h. Lysate of HEK 293 cells was separated by 10% SDS-PAGE followed by Western Blotting. The detection of the FZD7 protein was done by either using MAb-288.1, MAb-288.1+peptide C or a negative control Ab. MAb-288.1 binding to the FZD7 receptor was examined using HEK 293 cells over expressing FZD7. Cell extract was separated on SDS-PAGE and probed with different concentrations of MAb-288.1.

In order to further confirm specificity, immuno-precipitation (IP) was performed. Protein IP was performed on the melanoma cell-line cells using the indicated Abs.
Results:
FIG. 11A shows the results for IP by WB analysis. FIG. 11B shows that anti-FZD7 288-1 antibody binding site was blocked by peptide 4 and not by peptide 1. IP was successful when using 288-1 Ab. (Input—untreated fraction taken from cell lysate before IP was preformed; IP—immuno-precipitated fraction; control—nonspecific Ab control; mock—mouse anti human IgG control). FIG. 11A demonstrates that Anti FZD7 Ab 288-1 specifically immuno-precipitates the FZD7 protein. Antibody labeling of melanoma cells shows that an anti FZD7 Ab 288-1 conjugated to Cy3 labels melanoma cells (FIG. 10).

Conclusion

Specific binding of the Ab to FZD7 expressing cells was observed. FIG. 11A validates specific MAb-288.1 binding to FZD7 receptor. Further, the results shown in FIG. 11B demonstrate that MAb 288-1 binding FZD7 is blocked by peptide-C. FIG. 11C presents additional Western Blot results supporting specificity of MAb 288-1, wherein serial dilution of antibody corresponds with reduced signal.

Example 9: Functional Effect of Anti FZD7 Antibody 288-1 In Vitro

Percent (%) proliferation inhibition was measured in melanoma cells. Average % proliferation (n>5) in melanoma cell-line cells was measured by incubating cells for 48 hours in the absence (untreated) or in the presence of anti FZD7-Ab 288-1 at 5 µg/ml. Control untreated cells were set as 100%, average of % proliferation as indicated by the range markers in the bar graphs FIG. 12

Results:

FIG. 12 shows that anti FZD7 Ab 288-1 reduces proliferation in melanoma cells.

Example 10: Monoclonal Antibody 288-1 Inhibits Malignant Cells' Wnt Signaling In Vitro Expression of Wnt pathway target genes (AXIN2, CCND1, MYC-C), FZD7, 13-catenin, and Wnt pathway inhibitors (DKK1, sFRP1) was measured in SK-MEL28 (FIG. 13A) and WT cells (FIG. 13B).

Western Blot analysis was performed to identify active β-Catenin in melanoma cell-line cells and in Wilms' tumor cells after incubation for 48 hours in the absence (untreated) or in the presence of the anti FZD7 Ab 288-1 at the indicated concentrations. (FIGS. 6 and 13C)

Results:

Results presented in FIGS. 13A and 13B show MAb-288.1 inhibits expression of Wnt pathway related genes. For each cell type data were calculated as mean±S.E.M of five separate experiments, p<0.05. This correlates well with the reduction of active β-catenin expression shown in FIG. 6 and FIG. 13C.

Example 11: Monoclonal Antibody 288-1 Induces Apoptosis in Malignant Cells

Targeting FZD7 with MAb-288.1 induced cell death of SK-MEL28 and WT cells.

Methods:

Cell were treated with 5 µg/ml MAb-288.1 for 48 h and then stained for annexinV and 7AAD. Flow cytometry analysis of melanoma cell-line cells and Wilms' tumor cells was used. Cells stained positive for annexinV antibodies are either at pre-apoptotic, apoptotic, or necrotic stages. Gates were placed according to isotype control staining (IC<1%)

Results:

FIG. 14A presents the flow cytometry analysis of annexinV staining of cells following treatment with MAb-288.1. Results show a marked increase in % of pre-apoptotic cells in SK-MEL28 cells (left panels) as well as in WT cells (right panels). Further, Cells were treated with MAb-288.1, stained with 0.4% trypan blue and counted. % of dead cells was calculated. Results show % of dead cells was significantly lower in both SK-MEL28 (FIG. 14B) and WT (FIG. 14C) cells (p<0.05; n=4).

Example 12: Monoclonal Antibody 288-1 Prompts Depletion of Stemness Traits In Vitro In vitro treatment with MAb-288.1 diminished sternness traits. Colony forming ability (CFU) was compared between untreated and treated SK-MEL28 cells. The results presented in FIG. 15A demonstrate that the number of colonies formed by the treated cells was significantly lower than the untreated cells. Representative phase-contrast images of colonies formed from treated and untreated SK-MEL28 cells showing smaller colonies in the treated cells are presented in FIG. 15B. (scale bars=100 µm, magnification ×20). Sphere formation assays were performed on SK-MEL28 and WT cells. Number of spheres formed from the treated cells was significantly reduced in both SK-MEL28 (FIG. 15C) and WT (FIG. 15D) cells. Data is presented as mean±SEM of at least three experiments performed in triplicates (p=0.00098, p=0.00065, respectively). Representative phase-contrast images of spheres formed from treated and untreated SK-MEL28 cells (FIG. 15E) and WT cells (FIG. 15F) show much smaller, less condensed spheres in the treated cells (scale bars=100 µm, magnification ×10).

Example 13: Monoclonal Antibody 288-1 Treatment of SK-MEL28 Cells Demonstrates a Functional Effect-Inhibition of Cell Migration MAb-288.1 treatment of SK-MEL28 growth in tissue culture induced morphological changes on SK-MEL28 cells, as seen in FIG. 16A, wherein treated cells show a reduced spreading phenotype. Scale bar, 100 m. FIG. 16B presents the results of a migration assay, demonstrating that 5 µg/ml MAb-288.1 treatment of SK-MEL28 for 48 h significantly inhibited SK-MEL28 cells' migration capacity, as compared to untreated cells. Scale bar, 1000 µm.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for treating a tumor characterized by elevated expression of a Frizzled7 receptor in a subject, said method comprising the step of administering a therapeutically effective dose of an isolated antibody or antigen-binding portion thereof that binds to a Frizzled7 receptor, wherein the antibody binds to the cytoplasmic portion of said receptor and wherein the antibody has complementarity determining regions (CDRs) of the antibody produced by the hybridoma cell line 288-1 deposited in the American Type Culture Collection, Manassas, Va., USA, under the Registration Number PTA-123746; or the antibody produced by the hybridoma cell line 288-5 deposited in the American Type Culture Collection, Manassas, Va., USA, under the Registration Number PTA-123744.

2. The method of claim 1, wherein the isolated antibody or antigen-binding portion thereof is coupled to a cytotoxic moiety.

3. The method of claim 1, wherein the isolated antibody is recombinant antibody.

4. The method of claim 3, wherein the isolated antibody is a single chain antibody, Fab, Fv, diabody or triabody.

5. The method of claim 1, wherein said antibody is humanized, chimeric or chimeric/humanized.

6. The method of claim 1, wherein said tumor is Wilm's tumor.

7. The method of claim 1, wherein said tumor is comprised of melanoma cells.

8. The method of claim 1, wherein the method further comprises the step of administering a chemotherapy antibody.

9. The method of claim 1, wherein the method comprises the step of administering a second antibody or antigen-binding portion thereof.

10. The method of claim 1, wherein the isolated antibody is a whole antibody.

11. The method of claim 1, wherein the isolated antibody is IgG1, IgG2, IgG3 or IgG4.

12. The method of claim 1, wherein the isolated antibody induces antibody-dependent cellular cytotoxicity (ADCC).

* * * * *

UNITED STATES PATENT AND TRADEMARK OFFICE
CERTIFICATE OF CORRECTION

PATENT NO. : 10,465,004 B2  
APPLICATION NO. : 15/109173  
DATED : November 5, 2019  
INVENTOR(S) : Benjamin Dekel et al.

Page 1 of 1

It is certified that error appears in the above-identified patent and that said Letters Patent is hereby corrected as shown below:

On the Title Page

Item (72) Inventors:  
Line 3, "Harai" should be changed to --Harari--

Signed and Sealed this  
Twenty-fifth Day of February, 2020

Andrei Iancu  
*Director of the United States Patent and Trademark Office*

SEQUENCE LISTING

```
<160> NUMBER OF SEQ ID NOS: 15

<210> SEQ ID NO 1
<211> LENGTH: 16
<212> TYPE: PRT
<213> ORGANISM: Artificial Sequence
<220> FEATURE:
<223> OTHER INFORMATION: peptide

<400> SEQUENCE: 1

Arg Phe Tyr His Arg Leu Ser His Ser Ser Lys Gly Glu Thr Ala Val
```

```
<210> SEQ ID NO 2
<211> LENGTH: 14
<212> TYPE: PRT
<213> ORGANISM: Artificial Sequence
<220> FEATURE:
<223> OTHER INFORMATION: peptide

<400> SEQUENCE: 2

Gln Glu Asp Ala Gly Leu Glu Val His Gln Phe Tyr Pro Leu
1               5                   10

<210> SEQ ID NO 3
<211> LENGTH: 15
<212> TYPE: PRT
<213> ORGANISM: Artificial Sequence
<220> FEATURE:
<223> OTHER INFORMATION: peptide

<400> SEQUENCE: 3

Pro Gly Ala Ser Asp Gly Arg Gly Arg Pro Ala Phe Pro Phe Ser
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: peptide

<400> SEQUENCE: 4

Asp Gly Ser Gly Gly Pro Gly Gly Gly Pro Thr Ala Tyr Pro Thr Ala
1               5                   10                  15

<210> SEQ ID NO 5
<211> LENGTH: 647
<212> TYPE: PRT
<213> ORGANISM: Homo sapiens
<220> FEATURE:
<221> NAME/KEY: MISC_FEATURE
<223> OTHER INFORMATION: Frizzled -1 encoded by FZD1

<400> SEQUENCE: 5

Met Ala Glu Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
                20                  25                  30

Glu Gly Ser Gly Asp Ala Gly Gly Arg Arg Pro Pro Val Asp Pro
                35                  40                  45

Arg Arg Leu Ala Arg Gln Leu Leu Leu Leu Trp Leu Leu Glu Ala
        50                  55                  60

Pro Leu Leu Leu Gly Val Arg Ala Gln Ala Ala Gly Gln Gly Pro Gly
65                  70                  75                  80

Gln Gly Pro Gly Pro Gly Gln Gln Pro Pro Pro Gln Gln Gln
                85                  90                  95

Gln Ser Gly Gln Gln Tyr Asn Gly Glu Arg Gly Ile Ser Val Pro Asp
                100                 105                 110

His Gly Tyr Cys Gln Pro Ile Ser Ile Pro Leu Cys Thr Asp Ile Ala
                115                 120                 125

Tyr Asn Gln Thr Ile Met Pro Asn Leu Leu Gly His Thr Asn Gln Glu
        130                 135                 140
```

```
Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
            165                 170                 175

Cys Thr Val Leu Glu Gln Ala Leu Pro Pro Cys Arg Ser Leu Cys Glu
                180                 185                 190

Arg Ala Arg Gln Gly Cys Glu Ala Leu Met Asn Lys Phe Gly Phe Gln
            195                 200                 205

Trp Pro Asp Thr Leu Lys Cys Glu Lys Phe Pro His Gly Ala Gly
        210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly
            245                 250                 255

Gly His Arg Gly Gly Phe Pro Gly Gly Ala Gly Ala Ser Glu Arg Gly
                260                 265                 270

Lys Phe Ser Cys Pro Arg Ala Leu Lys Val Pro Ser Tyr Leu Asn Tyr
            275                 280                 285

His Phe Leu Gly Glu Lys Asp Cys Gly Ala Pro Cys Glu Pro Thr Lys
        290                 295                 300

Val Tyr Gly Leu Met Tyr Phe Gly Pro Glu Glu Leu Arg Phe Ser Arg
305                 310                 315                 320

Thr Trp Ile Gly Ile Trp Ser Val Leu Cys Cys Ala Ser Thr Leu Phe
            325                 330                 335

Thr Val Leu Thr Tyr Leu Val Asp Met Arg Arg Phe Ser Tyr Pro Glu
                340                 345                 350

Arg Pro Ile Ile Phe Leu Ser Gly Cys Tyr Thr Ala Val Ala Val Ala
            355                 360                 365

Tyr Ile Ala Gly Phe Leu Leu Glu Asp Arg Val Val Cys Asn Asp Lys
        370                 375                 380

Phe Ala Glu Asp Gly Ala Arg Thr Val Ala Gln Gly Thr Lys Lys Glu
385                 390                 395                 400

Gly Cys Thr Ile Leu Phe Met Met Leu Tyr Phe Phe Ser Met Ala Ser
            405                 410                 415

Ser Ile Trp Trp Val Ile Leu Ser Leu Thr Trp Phe Leu Ala Ala Gly
                420                 425                 430

Met Lys Trp Gly His Glu Ala Ile Glu Ala Asn Ser Gln Tyr Phe His
        435                 440                 445

Leu Ala Ala Trp Ala Val Pro Ala Ile Lys Thr Ile Thr Ile Leu Ala
    450                 455                 460

Leu Gly Gln Val Asp Gly Asp Val Leu Ser Gly Val Cys Phe Val Gly
465                 470                 475                 480

Leu Asn Asn Val Asp Ala Leu Arg Gly Phe Val Leu Ala Pro Leu Phe
            485                 490                 495

Val Tyr Leu Phe Ile Gly Thr Ser Phe Leu Leu Ala Gly Phe Val Ser
                500                 505                 510

Leu Phe Arg Ile Arg Thr Ile Met Lys His Asp Gly Thr Lys Thr Glu
            515                 520                 525

Lys Leu Glu Lys Leu Met Val Arg Ile Gly Val Phe Ser Val Leu Tyr
        530                 535                 540

Thr Val Pro Ala Thr Ile Val Ile Ala Cys Tyr Phe Tyr Glu Gln Ala
545                 550                 555                 560

Phe Arg Asp Gln Trp Glu Arg Ser Trp Val Ala Gln Ser Cys Lys Ser
```

```
                    565                 570                 575
Tyr Ala Ile Pro Cys Pro His Leu Gln Ala Gly Gly Ala Pro Pro
                580                 585                 590

His Pro Pro Met Ser Pro Asp Phe Thr Val Phe Met Ile Lys Tyr Leu
                595                 600                 605

Met Thr Leu Ile Val Gly Ile Thr Ser Gly Phe Trp Ile Trp Ser Gly
                610                 615                 620

Lys Thr Leu Asn Ser Trp Arg Lys Phe Tyr Thr Arg Leu Thr Asn Ser
625                 630                 635                 640

Lys Gln Gly Glu Thr Thr Val
                645

<210> SEQ ID NO 6
<211> LENGTH: 565
<212> TYPE: PRT
<213> ORGANISM: Homo sapiens
<220> FEATURE:
<221> NAME/KEY: MISC_FEATURE
<223> OTHER INFORMATION: frizzled-2 encoded by FZD2

<400> SEQUENCE: 6

Met Arg Pro Arg Ser Ala Leu Pro Arg Leu Leu Leu Pro Leu Leu Leu
1               5                   10                  15

Leu Pro Ala Ala Gly Pro Ala Gln Phe His Gly Glu Lys Gly Ile Ser
                20                  25                  30

Ile Pro Asp His Gly Phe Cys Gln Pro Ile Ser Ile Pro Leu Cys Thr
                35                  40                  45

Asp Ile Ala Tyr Asn Gln Thr Ile Met Pro Asn Leu Leu Gly His Thr
                50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95

Ala Pro Val Cys Thr Val Leu Glu Gln Ala Ile Pro Pro Cys Arg Ser
                100                 105                 110

Ile Cys Glu Arg Ala Arg Gln Gly Cys Glu Ala Leu Met Asn Lys Phe
                115                 120                 125

Gly Phe Gln Trp Pro Glu Arg Leu Arg Cys Glu His Phe Pro Arg His
                130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
                165                 170                 175

Gly Gly Thr Pro Gly Gly Pro Gly Gly Gly Ala Pro Pro Arg Tyr
                180                 185                 190

Ala Thr Leu Glu His Pro Phe His Cys Pro Arg Val Leu Lys Val Pro
                195                 200                 205

Ser Tyr Leu Ser Tyr Lys Phe Leu Gly Glu Arg Asp Cys Ala Ala Pro
                210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr Trp Ser Val Leu Cys Cys
                245                 250                 255

Ala Ser Thr Phe Phe Thr Val Thr Thr Tyr Leu Val Asp Met Gln Arg
                260                 265                 270
```

```
Phe Arg Tyr Pro Glu Arg Pro Ile Ile Phe Leu Ser Gly Cys Tyr Thr
                275                 280                 285

Met Val Ser Val Ala Tyr Ile Ala Gly Phe Val Leu Gln Glu Arg Val
        290                 295                 300

Val Cys Asn Glu Arg Phe Ser Glu Asp Gly Tyr Arg Thr Val Val Gln
305                 310                 315                 320

Gly Thr Lys Lys Glu Gly Cys Thr Ile Leu Phe Met Met Leu Tyr Phe
                325                 330                 335

Phe Ser Met Ala Ser Ser Ile Trp Trp Val Ile Leu Ser Leu Thr Trp
                340                 345                 350

Phe Leu Ala Ala Gly Met Lys Trp Gly His Glu Ala Ile Glu Ala Asn
                355                 360                 365

Ser Gln Tyr Phe His Leu Ala Ala Trp Ala Val Pro Ala Val Lys Thr
        370                 375                 380

Ile Thr Ile Leu Ala Met Gly Gln Ile Asp Gly Asp Leu Leu Ser Gly
385                 390                 395                 400

Val Cys Phe Val Gly Leu Asn Ser Leu Asp Pro Leu Arg Gly Phe Val
                405                 410                 415

Leu Ala Pro Leu Phe Val Tyr Leu Phe Ile Gly Thr Ser Phe Leu Leu
                420                 425                 430

Ala Gly Phe Val Ser Leu Phe Arg Ile Arg Thr Ile Met Lys His Asp
        435                 440                 445

Gly Thr Lys Thr Glu Lys Leu Glu Arg Leu Met Val Arg Ile Gly Val
                450                 455                 460

Phe Ser Val Leu Tyr Thr Val Pro Ala Thr Ile Val Ile Ala Cys Tyr
465                 470                 475                 480

Phe Tyr Glu Gln Ala Phe Arg Glu His Trp Glu Arg Ser Trp Val Ser
                485                 490                 495

Gln His Cys Lys Ser Leu Ala Ile Pro Cys Pro Ala His Tyr Thr Pro
                500                 505                 510

Arg Met Ser Pro Asp Phe Thr Val Tyr Met Ile Lys Tyr Leu Met Thr
                515                 520                 525

Leu Ile Val Gly Ile Thr Ser Gly Phe Trp Ile Trp Ser Gly Lys Thr
                530                 535                 540

Leu His Ser Trp Arg Lys Phe Tyr Thr Arg Leu Thr Asn Ser Arg His
545                 550                 555                 560

Gly Glu Thr Thr Val
                565

<210> SEQ ID NO 7
<211> LENGTH: 666
<212> TYPE: PRT
<213> ORGANISM: Homo sapiens
<220> FEATURE:
<221> NAME/KEY: MISC_FEATURE
<223> OTHER INFORMATION: Frizzled 3 encoded by FZD3

<400> SEQUENCE: 7

Met Ala Met Thr Trp Ile Val Phe Ser Leu Trp Pro Leu Thr Val Phe
1               5                   10                  15

Met Gly His Ile Gly Gly His Ser Leu Phe Ser Cys Glu Pro Ile Thr
                20                  25                  30

Leu Arg Met Cys Gln Asp Leu Pro Tyr Asn Thr Thr Phe Met Pro Asn
                35                  40                  45

Leu Leu Asn His Tyr Asp Gln Gln Thr Ala Ala Leu Ala Met Glu Pro
        50                  55                  60
```

-continued

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
            85                  90                  95

Leu Pro Cys Arg Arg Leu Cys Gln Arg Ala Tyr Ser Glu Cys Ser Lys
        100                 105                 110

Leu Met Glu Met Phe Gly Val Pro Trp Pro Glu Asp Met Glu Cys Ser
    115                 120                 125

Arg Phe Pro Asp Cys Asp Glu Pro Tyr Pro Arg Leu Val Asp Leu Asn
130                 135                 140

Leu Ala Gly Glu Pro Thr Glu Gly Ala Pro Val Ala Val Gln Arg Asp
145                 150                 155                 160

Tyr Gly Phe Trp Cys Pro Arg Glu Leu Lys Ile Asp Pro Asp Leu Gly
            165                 170                 175

Tyr Ser Phe Leu His Val Arg Asp Cys Ser Pro Pro Cys Pro Asn Met
        180                 185                 190

Tyr Phe Arg Arg Glu Glu Leu Ser Phe Ala Arg Tyr Phe Ile Gly Leu
    195                 200                 205

Ile Ser Ile Ile Cys Leu Ser Ala Thr Leu Phe Thr Phe Leu Thr Phe
210                 215                 220

Leu Ile Asp Val Thr Arg Phe Arg Tyr Pro Glu Arg Pro Ile Ile Phe
225                 230                 235                 240

Tyr Ala Val Cys Tyr Met Met Val Ser Leu Ile Phe Phe Ile Gly Phe
            245                 250                 255

Leu Leu Glu Asp Arg Val Ala Cys Asn Ala Ser Ile Pro Ala Gln Tyr
        260                 265                 270

Lys Ala Ser Thr Val Thr Gln Gly Ser His Asn Lys Ala Cys Thr Met
    275                 280                 285

Leu Phe Met Ile Leu Tyr Phe Phe Thr Met Ala Gly Ser Val Trp Trp
290                 295                 300

Val Ile Leu Thr Ile Thr Trp Phe Leu Ala Ala Val Pro Lys Trp Gly
305                 310                 315                 320

Ser Glu Ala Ile Glu Lys Lys Ala Leu Leu Phe His Ala Ser Ala Trp
            325                 330                 335

Gly Ile Pro Gly Thr Leu Thr Ile Ile Leu Leu Ala Met Asn Lys Ile
        340                 345                 350

Glu Gly Asp Asn Ile Ser Gly Val Cys Phe Val Gly Leu Tyr Asp Val
    355                 360                 365

Asp Ala Leu Arg Tyr Phe Val Leu Ala Pro Leu Cys Leu Tyr Val Val
    370                 375                 380

Val Gly Val Ser Leu Leu Leu Ala Gly Ile Ile Ser Leu Asn Arg Val
385                 390                 395                 400

Arg Ile Glu Ile Pro Leu Glu Lys Glu Asn Gln Asp Lys Leu Val Lys
            405                 410                 415

Phe Met Ile Arg Ile Gly Val Phe Ser Ile Leu Tyr Leu Val Pro Leu
        420                 425                 430

Leu Val Val Ile Gly Cys Tyr Phe Tyr Glu Gln Ala Tyr Arg Gly Ile
    435                 440                 445

Trp Glu Thr Thr Trp Ile Gln Glu Arg Cys Arg Glu Tyr His Ile Pro
    450                 455                 460

Cys Pro Tyr Gln Val Thr Gln Met Ser Arg Pro Asp Leu Ile Leu Phe
465                 470                 475                 480

```
Leu Met Lys Tyr Leu Met Ala Leu Ile Val Gly Ile Pro Ser Val Phe
                485                 490                 495

Trp Val Gly Ser Lys Lys Thr Cys Phe Glu Trp Ala Ser Phe Phe His
            500                 505                 510

Gly Arg Arg Lys Lys Glu Ile Val Asn Glu Ser Arg Gln Val Leu Gln
            515                 520                 525

Glu Pro Asp Phe Ala Gln Ser Leu Leu Arg Asp Pro Asn Thr Pro Ile
        530                 535                 540

Ile Arg Lys Ser Arg Gly Thr Ser Thr Gln Gly Thr Ser Thr His Ala
545                 550                 555                 560

Ser Ser Thr Gln Leu Ala Met Val Asp Asp Gln Arg Ser Lys Ala Gly
                565                 570                 575

Ser Ile His Ser Lys Val Ser Ser Tyr His Gly Ser Leu His Arg Ser
                580                 585                 590

Arg Asp Gly Arg Tyr Thr Pro Cys Ser Tyr Arg Gly Met Glu Glu Arg
                595                 600                 605

Leu Pro His Gly Ser Met Ser Arg Leu Thr Asp His Ser Arg His Ser
            610                 615                 620

Ser Ser His Arg Leu Asn Glu Gln Ser Arg His Ser Ser Ile Arg Asp
625                 630                 635                 640

Leu Ser Asn Asn Pro Met Thr His Ile Thr His Gly Thr Ser Met Asn
                645                 650                 655

Arg Val Ile Glu Glu Asp Gly Thr Ser Ala
                660                 665

<210> SEQ ID NO 8
<211> LENGTH: 537
<212> TYPE: PRT
<213> ORGANISM: Homo sapiens
<220> FEATURE:
<221> NAME/KEY: MISC_FEATURE
<223> OTHER INFORMATION: Frizzled-4 encoded by FZD4

<400> SEQUENCE: 8

Met Ala Trp Arg Gly Ala Gly Pro Ser Val Pro Gly Ala Pro Gly Gly
1               5                   10                  15

Val Gly Leu Ser Leu Gly Leu Leu Leu Gln Leu Leu Leu Leu Leu Gly
                20                  25                  30

Pro Ala Arg Gly Phe Gly Asp Glu Glu Glu Arg Arg Cys Asp Pro Ile
            35                  40                  45

Arg Ile Ser Met Cys Gln Asn Leu Gly Tyr Asn Val Thr Lys Met Pro
        50                  55                  60

Asn Leu Val Gly His Glu Leu Gln Thr Asp Ala Glu Leu Gln Leu Thr
65                  70                  75                  80

Thr Phe Thr Pro Leu Ile Gln Tyr Gly Cys Ser Ser Gln Leu Gln Phe
                85                  90                  95

Phe Leu Cys Ser Val Tyr Val Pro Met Cys Thr Glu Lys Ile Asn Ile
            100                 105                 110

Pro Ile Gly Pro Cys Gly Gly Met Cys Leu Ser Val Lys Arg Arg Cys
        115                 120                 125

Glu Pro Val Leu Lys Glu Phe Gly Phe Ala Trp Pro Glu Ser Leu Asn
    130                 135                 140

Cys Ser Lys Phe Pro Pro Gln Asn Asp His Asn His Met Cys Met Glu
145                 150                 155                 160

Gly Pro Gly Asp Glu Glu Val Pro Leu Pro His Lys Thr Pro Ile Gln
                165                 170                 175
```

Pro Gly Glu Glu Cys His Ser Val Gly Thr Asn Ser Asp Gln Tyr Ile
            180                 185                 190

Trp Val Lys Arg Ser Leu Asn Cys Val Leu Lys Cys Gly Tyr Asp Ala
        195                 200                 205

Gly Leu Tyr Ser Arg Ser Ala Lys Glu Phe Thr Asp Ile Trp Met Ala
    210                 215                 220

Val Trp Ala Ser Leu Cys Phe Ile Ser Thr Ala Phe Thr Val Leu Thr
225                 230                 235                 240

Phe Leu Ile Asp Ser Ser Arg Phe Ser Tyr Pro Glu Arg Pro Ile Ile
                245                 250                 255

Phe Leu Ser Met Cys Tyr Asn Ile Tyr Ser Ile Ala Tyr Ile Val Arg
            260                 265                 270

Leu Thr Val Gly Arg Glu Arg Ile Ser Cys Asp Phe Glu Glu Ala Ala
        275                 280                 285

Glu Pro Val Leu Ile Gln Glu Gly Leu Lys Asn Thr Gly Cys Ala Ile
    290                 295                 300

Ile Phe Leu Leu Met Tyr Phe Phe Gly Met Ala Ser Ser Ile Trp Trp
305                 310                 315                 320

Val Ile Leu Thr Leu Thr Trp Phe Leu Ala Ala Gly Leu Lys Trp Gly
                325                 330                 335

His Glu Ala Ile Glu Met His Ser Ser Tyr Phe His Ile Ala Ala Trp
            340                 345                 350

Ala Ile Pro Ala Val Lys Thr Ile Val Ile Leu Ile Met Arg Leu Val
        355                 360                 365

Asp Ala Asp Glu Leu Thr Gly Leu Cys Tyr Val Gly Asn Gln Asn Leu
    370                 375                 380

Asp Ala Leu Thr Gly Phe Val Val Ala Pro Leu Phe Thr Tyr Leu Val
385                 390                 395                 400

Ile Gly Thr Leu Phe Ile Ala Ala Gly Leu Val Ala Leu Phe Lys Ile
                405                 410                 415

Arg Ser Asn Leu Gln Lys Asp Gly Thr Lys Thr Asp Lys Leu Glu Arg
            420                 425                 430

Leu Met Val Lys Ile Gly Val Phe Ser Val Leu Tyr Thr Val Pro Ala
        435                 440                 445

Thr Cys Val Ile Ala Cys Tyr Phe Tyr Glu Ile Ser Asn Trp Ala Leu
    450                 455                 460

Phe Arg Tyr Ser Ala Asp Asp Ser Asn Met Ala Val Glu Met Leu Lys
465                 470                 475                 480

Ile Phe Met Ser Leu Leu Val Gly Ile Thr Ser Gly Met Trp Ile Trp
                485                 490                 495

Ser Ala Lys Thr Leu His Thr Trp Gln Lys Cys Ser Asn Arg Leu Val
            500                 505                 510

Asn Ser Gly Lys Val Lys Arg Glu Lys Arg Gly Asn Gly Trp Val Lys
        515                 520                 525

Pro Gly Lys Gly Ser Glu Thr Val Val
    530                 535

<210> SEQ ID NO 9
<211> LENGTH: 585
<212> TYPE: PRT
<213> ORGANISM: Homo sapiens
<220> FEATURE:
<221> NAME/KEY: MISC_FEATURE
<223> OTHER INFORMATION: Frizzled-5 encoded by FZD5

```
<400> SEQUENCE: 9

Met Ala Arg Pro Asp Pro Ser Ala Pro Pro Ser Leu Leu Leu Leu
1               5                   10                  15

Leu Ala Gln Leu Val Gly Arg Ala Ala Ala Ser Lys Ala Pro Val
                20                  25                  30

Cys Gln Glu Ile Thr Val Pro Met Cys Arg Gly Ile Gly Tyr Asn Leu
                35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
                100                 105                 110

Lys Ala Gly Cys Ser Pro Leu Met Arg Gln Tyr Gly Phe Ala Trp Pro
                115                 120                 125

Glu Arg Met Ser Cys Asp Arg Leu Pro Val Leu Gly Arg Asp Ala Glu
130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
                180                 185                 190

Arg Glu Pro Phe Val Pro Ile Leu Lys Glu Ser His Pro Leu Tyr Asn
                195                 200                 205

Lys Val Arg Thr Gly Gln Val Pro Asn Cys Ala Val Pro Cys Tyr Gln
                210                 215                 220

Pro Ser Phe Ser Ala Asp Glu Arg Thr Phe Ala Thr Phe Trp Ile Gly
225                 230                 235                 240

Leu Trp Ser Val Leu Cys Phe Ile Ser Thr Ser Thr Thr Val Ala Thr
                245                 250                 255

Phe Leu Ile Asp Met Glu Arg Phe Arg Tyr Pro Glu Arg Pro Ile Ile
                260                 265                 270

Phe Leu Ser Ala Cys Tyr Leu Cys Val Ser Leu Gly Phe Leu Val Arg
                275                 280                 285

Leu Val Val Gly His Ala Ser Val Ala Cys Ser Arg Glu His Asn His
                290                 295                 300

Ile His Tyr Glu Thr Thr Gly Pro Ala Leu Cys Thr Ile Val Phe Leu
305                 310                 315                 320

Leu Val Tyr Phe Phe Gly Met Ala Ser Ser Ile Trp Trp Val Ile Leu
                325                 330                 335

Ser Leu Thr Trp Phe Leu Ala Ala Gly Met Lys Trp Gly Asn Glu Ala
                340                 345                 350

Ile Ala Gly Tyr Ala Gln Tyr Phe His Leu Ala Ala Trp Leu Ile Pro
                355                 360                 365

Ser Val Lys Ser Ile Thr Ala Leu Ala Leu Ser Ser Val Asp Gly Asp
                370                 375                 380

Pro Val Ala Gly Ile Cys Tyr Val Gly Asn Gln Asn Leu Asn Ser Leu
385                 390                 395                 400

Arg Gly Phe Val Leu Gly Pro Leu Val Leu Tyr Leu Leu Val Gly Thr
                405                 410                 415
```

```
Leu Phe Leu Leu Ala Gly Phe Val Ser Leu Phe Arg Ile Arg Ser Val
                420                 425                 430
Ile Lys Gln Gly Gly Thr Lys Thr Asp Lys Leu Glu Lys Leu Met Ile
            435                 440                 445
Arg Ile Gly Ile Phe Thr Leu Leu Tyr Thr Val Pro Ala Ser Ile Val
450                 455                 460
Val Ala Cys Tyr Leu Tyr Glu Gln His Tyr Arg Glu Ser Trp Glu Ala
465                 470                 475                 480
Ala Leu Thr Cys Ala Cys Pro Gly His Asp Thr Gly Gln Pro Arg Ala
                485                 490                 495
Lys Pro Glu Tyr Trp Val Leu Met Leu Lys Tyr Phe Met Cys Leu Val
            500                 505                 510
Val Gly Ile Thr Ser Gly Val Trp Ile Trp Ser Gly Lys Thr Val Glu
        515                 520                 525
Ser Trp Arg Arg Phe Thr Ser Arg Cys Cys Arg Pro Arg Arg Gly
530                 535                 540
His Lys Ser Gly Gly Ala Met Ala Ala Gly Asp Tyr Pro Glu Ala Ser
545                 550                 555                 560
Ala Ala Leu Thr Gly Arg Thr Gly Pro Pro Gly Pro Ala Ala Thr Tyr
                565                 570                 575
His Lys Gln Val Ser Leu Ser His Val
            580                 585

<210> SEQ ID NO 10
<211> LENGTH: 706
<212> TYPE: PRT
<213> ORGANISM: Homo sapiens
<220> FEATURE:
<221> NAME/KEY: MISC_FEATURE
<223> OTHER INFORMATION: Frizzled-6 encoded by FZD6

<400> SEQUENCE: 10

Met Glu Met Phe Thr Phe Leu Leu Thr Cys Ile Phe Leu Pro Leu Leu
1               5                   10                  15
Arg Gly His Ser Leu Phe Thr Cys Glu Pro Ile Thr Val Pro Arg Cys
            20                  25                  30
Met Lys Met Ala Tyr Asn Met Thr Phe Phe Pro Asn Leu Met Gly His
        35                  40                  45
Tyr Asp Gln Ser Ile Ala Ala Val Glu Met Glu His Phe Leu Pro Leu
    50                  55                  60
Ala Asn Leu Glu Cys Ser Pro Asn Ile Glu Thr Phe Leu Cys Lys Ala
65                  70                  75                  80
Phe Val Pro Thr Cys Ile Glu Gln Ile His Val Val Pro Pro Cys Arg
                85                  90                  95
Lys Leu Cys Glu Lys Val Tyr Ser Asp Cys Lys Lys Leu Ile Asp Thr
            100                 105                 110
Phe Gly Ile Arg Trp Pro Glu Glu Leu Glu Cys Asp Arg Leu Gln Tyr
        115                 120                 125
Cys Asp Glu Thr Val Pro Val Thr Phe Asp Pro His Thr Glu Phe Leu
    130                 135                 140
Gly Pro Gln Lys Lys Thr Glu Gln Val Gln Arg Asp Ile Gly Phe Trp
145                 150                 155                 160
Cys Pro Arg His Leu Lys Thr Ser Gly Gly Gln Gly Tyr Lys Phe Leu
                165                 170                 175
Gly Ile Asp Gln Cys Ala Pro Pro Cys Pro Asn Met Tyr Phe Lys Ser
```

```
            180                 185                 190
Asp Glu Leu Glu Phe Ala Lys Ser Phe Ile Gly Thr Val Ser Ile Phe
            195                 200                 205

Cys Leu Cys Ala Thr Leu Phe Thr Phe Leu Thr Phe Leu Ile Asp Val
            210                 215                 220

Arg Arg Phe Arg Tyr Pro Glu Arg Pro Ile Ile Tyr Tyr Ser Val Cys
225                 230                 235                 240

Tyr Ser Ile Val Ser Leu Met Tyr Phe Ile Gly Phe Leu Leu Gly Asp
                245                 250                 255

Ser Thr Ala Cys Asn Lys Ala Asp Glu Lys Leu Glu Leu Gly Asp Thr
                260                 265                 270

Val Val Leu Gly Ser Gln Asn Lys Ala Cys Thr Val Leu Phe Met Leu
                275                 280                 285

Leu Tyr Phe Phe Thr Met Ala Gly Thr Val Trp Val Ile Leu Thr
            290                 295                 300

Ile Thr Trp Phe Leu Ala Ala Gly Arg Lys Trp Ser Cys Glu Ala Ile
305                 310                 315                 320

Glu Gln Lys Ala Val Trp Phe His Ala Val Ala Trp Gly Thr Pro Gly
                325                 330                 335

Phe Leu Thr Val Met Leu Leu Ala Met Asn Lys Val Glu Gly Asp Asn
                340                 345                 350

Ile Ser Gly Val Cys Phe Val Gly Leu Tyr Asp Leu Asp Ala Ser Arg
            355                 360                 365

Tyr Phe Val Leu Leu Pro Leu Cys Leu Cys Val Phe Val Gly Leu Ser
            370                 375                 380

Leu Leu Leu Ala Gly Ile Ile Ser Leu Asn His Val Arg Gln Val Ile
385                 390                 395                 400

Gln His Asp Gly Arg Asn Gln Glu Lys Leu Lys Lys Phe Met Ile Arg
                405                 410                 415

Ile Gly Val Phe Ser Gly Leu Tyr Leu Val Pro Leu Val Thr Leu Leu
            420                 425                 430

Gly Cys Tyr Val Tyr Glu Gln Val Asn Arg Ile Thr Trp Glu Ile Thr
            435                 440                 445

Trp Val Ser Asp His Cys Arg Gln Tyr His Ile Pro Cys Pro Tyr Gln
450                 455                 460

Ala Lys Ala Lys Ala Arg Pro Glu Leu Ala Leu Phe Met Ile Lys Tyr
465                 470                 475                 480

Leu Met Thr Leu Ile Val Gly Ile Ser Ala Val Phe Trp Val Gly Ser
                485                 490                 495

Lys Lys Thr Cys Thr Glu Trp Ala Gly Phe Phe Lys Arg Asn Arg Lys
                500                 505                 510

Arg Asp Pro Ile Ser Glu Ser Arg Arg Val Leu Gln Glu Ser Cys Glu
            515                 520                 525

Phe Phe Leu Lys His Asn Ser Lys Val Lys His Lys Lys His Tyr
            530                 535                 540

Lys Pro Ser Ser His Lys Leu Lys Val Ile Ser Lys Ser Met Gly Thr
545                 550                 555                 560

Ser Thr Gly Ala Thr Ala Asn His Gly Thr Ser Ala Val Ala Ile Thr
                565                 570                 575

Ser His Asp Tyr Leu Gly Gln Glu Thr Leu Thr Glu Ile Gln Thr Ser
            580                 585                 590

Pro Glu Thr Ser Met Arg Glu Val Lys Ala Asp Gly Ala Ser Thr Pro
            595                 600                 605
```

```
Arg Leu Arg Glu Gln Asp Cys Gly Glu Pro Ala Ser Pro Ala Ala Ser
            610                 615                 620
Ile Ser Arg Leu Ser Gly Glu Gln Val Asp Gly Lys Gly Gln Ala Gly
625                 630                 635                 640
Ser Val Ser Glu Ser Ala Arg Ser Glu Gly Arg Ile Ser Pro Lys Ser
                645                 650                 655
Asp Ile Thr Asp Thr Gly Leu Ala Gln Ser Asn Asn Leu Gln Val Pro
            660                 665                 670
Ser Ser Ser Glu Pro Ser Ser Leu Lys Gly Ser Thr Ser Leu Leu Val
        675                 680                 685
His Pro Val Ser Gly Val Arg Lys Glu Gln Gly Gly Gly Cys His Ser
    690                 695                 700
Asp Thr
705

<210> SEQ ID NO 11
<211> LENGTH: 574
<212> TYPE: PRT
<213> ORGANISM: Homo sapiens
<220> FEATURE:
<221> NAME/KEY: MISC_FEATURE
<223> OTHER INFORMATION: Frizzled-7 encoded by FZD7

<400> SEQUENCE: 11

Met Arg Asp Pro Gly Ala Ala Ala Pro Leu Ser Ser Leu Gly Leu Cys
1               5                   10                  15
Ala Leu Val Leu Ala Leu Leu Gly Ala Leu Ser Ala Gly Ala Gly Ala
            20                  25                  30
Gln Pro Tyr His Gly Glu Lys Gly Ile Ser Val Pro Asp His Gly Phe
        35                  40                  45
Cys Gln Pro Ile Ser Ile Pro Leu Cys Thr Asp Ile Ala Tyr Asn Gln
    50                  55                  60
Thr Ile Leu Pro Asn Leu Leu Gly His Thr Asn Gln Glu Asp Ala Gly
65                  70                  75                  80
Leu Glu Val His Gln Phe Tyr Pro Leu Val Lys Val Gln Cys Ser Pro
                85                  90                  95
Glu Leu Arg Phe Phe Leu Cys Ser Met Tyr Ala Pro Val Cys Thr Val
            100                 105                 110
Leu Asp Gln Ala Ile Pro Pro Cys Arg Ser Leu Cys Glu Arg Ala Arg
        115                 120                 125
Gln Gly Cys Glu Ala Leu Met Asn Lys Phe Gly Phe Gln Trp Pro Glu
    130                 135                 140
Arg Leu Arg Cys Glu Asn Phe Pro Val His Gly Ala Gly Glu Ile Cys
145                 150                 155                 160
Val Gly Gln Asn Thr Ser Asp Gly Ser Gly Gly Pro Gly Gly Gly Pro
                165                 170                 175
Thr Ala Tyr Pro Thr Ala Pro Tyr Leu Pro Asp Leu Pro Phe Thr Ala
            180                 185                 190
Leu Pro Pro Gly Ala Ser Asp Gly Arg Gly Arg Pro Ala Phe Pro Phe
        195                 200                 205
Ser Cys Pro Arg Gln Leu Lys Val Pro Pro Tyr Leu Gly Tyr Arg Phe
    210                 215                 220
Leu Gly Glu Arg Asp Cys Gly Ala Pro Cys Glu Pro Gly Arg Ala Asn
225                 230                 235                 240
Gly Leu Met Tyr Phe Lys Glu Glu Glu Arg Arg Phe Ala Arg Leu Trp
```

-continued

```
                245                 250                 255
Val Gly Val Trp Ser Val Leu Cys Cys Ala Ser Thr Leu Phe Thr Val
            260                 265                 270

Leu Thr Tyr Leu Val Asp Met Arg Arg Phe Ser Tyr Pro Glu Arg Pro
        275                 280                 285

Ile Ile Phe Leu Ser Gly Cys Tyr Phe Met Val Ala Val His Val
    290                 295                 300

Ala Gly Phe Leu Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
            325                 330                 335

Thr Ile Leu Phe Met Val Leu Tyr Phe Phe Gly Met Ala Ser Ser Ile
        340                 345                 350

Trp Trp Val Ile Leu Ser Leu Thr Trp Phe Leu Ala Ala Gly Met Lys
    355                 360                 365

Trp Gly His Glu Ala Ile Glu Ala Asn Ser Gln Tyr Phe His Leu Ala
370                 375                 380

Ala Trp Ala Val Pro Ala Val Lys Thr Ile Thr Ile Leu Ala Met Gly
385                 390                 395                 400

Gln Val Asp Gly Asp Leu Leu Ser Gly Val Cys Tyr Val Gly Leu Ser
            405                 410                 415

Ser Val Asp Ala Leu Arg Gly Phe Val Leu Ala Pro Leu Phe Val Tyr
        420                 425                 430

Leu Phe Ile Gly Thr Ser Phe Leu Leu Ala Gly Phe Val Ser Leu Phe
    435                 440                 445

Arg Ile Arg Thr Ile Met Lys His Asp Gly Thr Lys Thr Glu Lys Leu
450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
            485                 490                 495

Glu His Trp Glu Arg Thr Trp Leu Leu Gln Thr Cys Lys Ser Tyr Ala
        500                 505                 510

Val Pro Cys Pro Pro Gly His Phe Pro Pro Met Ser Pro Asp Phe Thr
    515                 520                 525

Val Phe Met Ile Lys Tyr Leu Met Thr Met Ile Val Gly Ile Thr Thr
530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
            565                 570
```

<210> SEQ ID NO 12
<211> LENGTH: 694
<212> TYPE: PRT
<213> ORGANISM: Homo sapiens
<220> FEATURE:
<221> NAME/KEY: MISC_FEATURE
<223> OTHER INFORMATION: Frizzled-8 encoded by FZD8

<400> SEQUENCE: 12

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30
```

-continued

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
 50                  55                  60

Ala Gly Leu Glu Val His Gln Phe Trp Pro Leu Val Glu Ile Gln Cys
 65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
                100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
        195                 200                 205

Ala Arg Gly Gly Gly Gly Gly Lys Ala Arg Pro Pro Gly Gly Gly
    210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
    275                 280                 285

Phe Val Ser Thr Phe Ala Thr Val Ser Thr Phe Leu Ile Asp Met Glu
290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Ala Pro Gly Ala Gly Gly Ala Gly Gly
            340                 345                 350

Ala Gly Gly Ala Ala Gly Ala Gly Ala Gly Ala Gly Ala Gly
        355                 360                 365

Gly Pro Gly Gly Arg Gly Glu Tyr Glu Glu Leu Gly Ala Val Glu Gln
    370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
            420                 425                 430

Ala Ile Ala Gly Tyr Ser Gln Tyr Phe His Leu Ala Ala Trp Leu Val
        435                 440                 445

Pro Ser Val Lys Ser Ile Ala Val Leu Ala Leu Ser Ser Val Asp Gly

```
                450                 455                 460
Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
                485                 490                 495

Thr Met Phe Leu Leu Ala Gly Phe Val Ser Leu Phe Arg Ile Arg Ser
                500                 505                 510

Val Ile Lys Gln Gln Asp Gly Pro Thr Lys Thr His Lys Leu Glu Lys
                515                 520                 525

Leu Met Ile Arg Leu Gly Leu Phe Thr Val Leu Tyr Thr Val Pro Ala
                530                 535                 540

Ala Val Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
                565                 570                 575

Gln Ala Arg Arg Pro Asp Tyr Ala Val Phe Met Leu Lys Tyr Phe Met
                580                 585                 590

Cys Leu Val Val Gly Ile Thr Ser Gly Val Trp Val Trp Ser Gly Lys
                595                 600                 605

Thr Leu Glu Ser Trp Arg Ser Leu Cys Thr Arg Cys Cys Trp Ala Ser
                610                 615                 620

Lys Gly Ala Ala Val Gly Gly Ala Gly Ala Thr Ala Ala Gly Gly
625                 630                 635                 640

Gly Gly Gly Pro Gly Gly Gly Gly Gly Pro Gly Gly Gly
                645                 650                 655

Gly Pro Gly Gly Gly Gly Ser Leu Tyr Ser Asp Val Ser Thr Gly
                660                 665                 670

Leu Thr Trp Arg Ser Gly Thr Ala Ser Ser Val Ser Tyr Pro Lys Gln
                675                 680                 685

Met Pro Leu Ser Gln Val
                690

<210> SEQ ID NO 13
<211> LENGTH: 591
<212> TYPE: PRT
<213> ORGANISM: Homo sapiens
<220> FEATURE:
<221> NAME/KEY: MISC_FEATURE
<223> OTHER INFORMATION: Frizzled-9 encoded by FZD9

<400> SEQUENCE: 13

Met Ala Val Ala Pro Leu Arg Gly Ala Leu Leu Leu Trp Gln Leu Leu
1               5                   10                  15

Ala Ala Gly Gly Ala Ala Leu Glu Ile Gly Arg Phe Asp Pro Glu Arg
                20                  25                  30

Gly Arg Gly Ala Ala Pro Cys Gln Ala Val Glu Ile Pro Met Cys Arg
                35                  40                  45

Gly Ile Gly Tyr Asn Leu Thr Arg Met Pro Asn Leu Leu Gly His Thr
                50                  55                  60

Ser Gln Gly Glu Ala Ala Ala Glu Leu Ala Glu Phe Ala Pro Leu Val
65                  70                  75                  80

Gln Tyr Gly Cys His Ser His Leu Arg Phe Phe Leu Cys Ser Leu Tyr
                85                  90                  95

Ala Pro Met Cys Thr Asp Gln Val Ser Thr Pro Ile Pro Ala Cys Arg
                100                 105                 110
```

-continued

```
Pro Met Cys Glu Gln Ala Arg Leu Arg Cys Ala Pro Ile Met Glu Gln
        115                 120                 125
Phe Asn Phe Gly Trp Pro Asp Ser Leu Asp Cys Ala Arg Leu Pro Thr
130                 135                 140
Arg Asn Asp Pro His Ala Leu Cys Met Glu Ala Pro Glu Asn Ala Thr
145                 150                 155                 160
Ala Gly Pro Ala Glu Pro His Lys Gly Leu Gly Met Leu Pro Val Ala
                165                 170                 175
Pro Arg Pro Ala Arg Pro Gly Asp Leu Gly Pro Gly Ala Gly Gly
            180                 185                 190
Ser Gly Thr Cys Glu Asn Pro Glu Lys Phe Gln Tyr Val Glu Lys Ser
        195                 200                 205
Arg Ser Cys Ala Pro Arg Cys Gly Pro Gly Val Glu Val Phe Trp Ser
    210                 215                 220
Arg Arg Asp Lys Asp Phe Ala Leu Val Trp Met Ala Val Trp Ser Ala
225                 230                 235                 240
Leu Cys Phe Phe Ser Thr Ala Phe Thr Val Leu Thr Phe Leu Leu Glu
                245                 250                 255
Pro His Arg Phe Gln Tyr Pro Glu Arg Pro Ile Ile Phe Leu Ser Met
            260                 265                 270
Cys Tyr Asn Val Tyr Ser Leu Ala Phe Leu Ile Arg Ala Val Ala Gly
        275                 280                 285
Ala Gln Ser Val Ala Cys Asp Gln Glu Ala Gly Ala Leu Tyr Val Ile
    290                 295                 300
Gln Glu Gly Leu Glu Asn Thr Gly Cys Thr Leu Val Phe Leu Leu Leu
305                 310                 315                 320
Tyr Tyr Phe Gly Met Ala Ser Ser Leu Trp Trp Val Val Leu Thr Leu
                325                 330                 335
Thr Trp Phe Leu Ala Ala Gly Lys Lys Trp Gly His Glu Ala Ile Glu
            340                 345                 350
Ala His Gly Ser Tyr Phe His Met Ala Ala Trp Gly Leu Pro Ala Leu
        355                 360                 365
Lys Thr Ile Val Ile Leu Thr Leu Arg Lys Val Ala Gly Asp Glu Leu
    370                 375                 380
Thr Gly Leu Cys Tyr Val Ala Ser Thr Asp Ala Ala Ala Leu Thr Gly
385                 390                 395                 400
Phe Val Leu Val Pro Leu Ser Gly Tyr Leu Val Leu Gly Ser Ser Phe
                405                 410                 415
Leu Leu Thr Gly Phe Val Ala Leu Phe His Ile Arg Lys Ile Met Lys
            420                 425                 430
Thr Gly Gly Thr Asn Thr Glu Lys Leu Glu Lys Leu Met Val Lys Ile
        435                 440                 445
Gly Val Phe Ser Ile Leu Tyr Thr Val Pro Ala Thr Cys Val Ile Val
    450                 455                 460
Cys Tyr Val Tyr Glu Arg Leu Asn Met Asp Phe Trp Arg Leu Arg Ala
465                 470                 475                 480
Thr Glu Gln Pro Cys Ala Ala Ala Gly Pro Gly Arg Arg Asp
                485                 490                 495
Cys Ser Leu Pro Gly Gly Ser Val Pro Thr Val Ala Val Phe Met Leu
            500                 505                 510
Lys Ile Phe Met Ser Leu Val Val Gly Ile Thr Ser Gly Val Trp Val
        515                 520                 525
Trp Ser Ser Lys Thr Phe Gln Thr Trp Gln Ser Leu Cys Tyr Arg Lys
```

```
                    530                535                540
Ile Ala Ala Gly Arg Ala Arg Ala Lys Ala Cys Arg Ala Pro Gly Ser
545                 550                555                560

Tyr Gly Arg Gly Thr His Cys His Tyr Lys Ala Pro Thr Val Val Leu
                565                570                575

His Met Thr Lys Thr Asp Pro Ser Leu Glu Asn Pro Thr His Leu
                580                585                590

<210> SEQ ID NO 14
<211> LENGTH: 581
<212> TYPE: PRT
<213> ORGANISM: Homo sapiens
<220> FEATURE:
<221> NAME/KEY: MISC_FEATURE
<223> OTHER INFORMATION: Frizzled-10 encoded by FZD10

<400> SEQUENCE: 14

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
                20                  25                  30

Lys Cys Gln Pro Ile Glu Ile Pro Met Cys Lys Asp Ile Gly Tyr Asn
            35                  40                  45

Met Thr Arg Met Pro Asn Leu Met Gly His Glu Asn Gln Arg Glu Ala
50                  55                  60

Ala Ile Gln Leu His Glu Phe Ala Pro Leu Val Glu Tyr Gly Cys His
65              70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
                165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
        195                 200                 205

Pro Leu Cys Thr Pro Gly Val Asp Val Tyr Trp Ser Arg Glu Asp Lys
    210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
            260                 265                 270

Tyr Ser Val Gly Tyr Leu Ile Arg Leu Phe Ala Gly Ala Glu Ser Ile
        275                 280                 285

Ala Cys Asp Arg Asp Ser Gly Gln Leu Tyr Val Ile Gln Glu Gly Leu
    290                 295                 300
```

```
Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
            325                 330                 335

Ala Ala Gly Lys Lys Trp Gly His Glu Ala Ile Glu Ala Asn Ser Ser
            340                 345                 350

Tyr Phe His Leu Ala Ala Trp Ala Ile Pro Ala Val Lys Thr Ile Leu
            355                 360                 365

Ile Leu Val Met Arg Arg Val Ala Gly Asp Glu Leu Thr Gly Val Cys
            370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
            405                 410                 415

Phe Val Ala Leu Phe His Ile Arg Arg Val Met Lys Thr Gly Gly Glu
            420                 425                 430

Asn Thr Asp Lys Leu Glu Lys Leu Met Val Arg Ile Gly Leu Phe Ser
            435                 440                 445

Val Leu Tyr Thr Val Pro Ala Thr Cys Val Ile Ala Cys Tyr Phe Tyr
450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
            485                 490                 495

Ser Ile Pro Ala Val Glu Ile Phe Met Val Lys Ile Phe Met Leu Leu
            500                 505                 510

Val Val Gly Ile Thr Ser Gly Met Trp Ile Trp Thr Ser Lys Thr Leu
            515                 520                 525

Gln Ser Trp Gln Gln Val Cys Ser Arg Arg Leu Lys Lys Lys Ser Arg
            530                 535                 540

Arg Lys Pro Ala Ser Val Ile Thr Ser Gly Gly Ile Tyr Lys Lys Ala
545                 550                 555                 560

Gln His Pro Gln Lys Thr His His Gly Lys Tyr Glu Ile Pro Ala Gln
            565                 570                 575

Ser Pro Thr Cys Val
            580

<210> SEQ ID NO 15
<211> LENGTH: 787
<212> TYPE: PRT
<213> ORGANISM: Homo sapiens
<220> FEATURE:
<221> NAME/KEY: MISC_FEATURE
<223> OTHER INFORMATION: smoothened homolog precursor encoded by SMO
      (FZD11)

<400> SEQUENCE: 15

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
            20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
50                  55                  60

Gly Arg Ala Ala Pro Cys Glu Pro Leu Arg Tyr Asn Val Cys Leu Gly
```

-continued

```
                65                  70                  75                  80
        Ser Val Leu Pro Tyr Gly Ala Thr Ser Thr Leu Leu Ala Gly Asp Ser
                            85                  90                  95

Asp Ser Gln Glu Glu Ala His Gly Lys Leu Val Leu Trp Ser Gly Leu
                            100                 105                 110

Arg Asn Ala Pro Arg Cys Trp Ala Val Ile Gln Pro Leu Leu Cys Ala
                            115                 120                 125

Val Tyr Met Pro Lys Cys Glu Asn Asp Arg Val Glu Leu Pro Ser Arg
            130                 135                 140

Thr Leu Cys Gln Ala Thr Arg Gly Pro Cys Ala Ile Val Glu Arg Glu
        145                 150                 155                 160

Arg Gly Trp Pro Asp Phe Leu Arg Cys Thr Pro Asp Arg Phe Pro Glu
                            165                 170                 175

Gly Cys Thr Asn Glu Val Gln Asn Ile Lys Phe Asn Ser Ser Gly Gln
                            180                 185                 190

Cys Glu Val Pro Leu Val Arg Thr Asp Asn Pro Lys Ser Trp Tyr Glu
                            195                 200                 205

Asp Val Glu Gly Cys Gly Ile Gln Cys Gln Asn Pro Leu Phe Thr Glu
            210                 215                 220

Ala Glu His Gln Asp Met His Ser Tyr Ile Ala Ala Phe Gly Ala Val
        225                 230                 235                 240

Thr Gly Leu Cys Thr Leu Phe Thr Leu Ala Thr Phe Val Ala Asp Trp
                            245                 250                 255

Arg Asn Ser Asn Arg Tyr Pro Ala Val Ile Leu Phe Tyr Val Asn Ala
                            260                 265                 270

Cys Phe Phe Val Gly Ser Ile Gly Trp Leu Ala Gln Phe Met Asp Gly
                    275                 280                 285

Ala Arg Arg Glu Ile Val Cys Arg Ala Asp Gly Thr Met Arg Leu Gly
                    290                 295                 300

Glu Pro Thr Ser Asn Glu Thr Leu Ser Cys Val Ile Ile Phe Val Ile
        305                 310                 315                 320

Val Tyr Tyr Ala Leu Met Ala Gly Val Val Trp Phe Val Val Leu Thr
                            325                 330                 335

Tyr Ala Trp His Thr Ser Phe Lys Ala Leu Gly Thr Thr Tyr Gln Pro
                            340                 345                 350

Leu Ser Gly Lys Thr Ser Tyr Phe His Leu Leu Thr Trp Ser Leu Pro
                    355                 360                 365

Phe Val Leu Thr Val Ala Ile Leu Ala Val Ala Gln Val Asp Gly Asp
                    370                 375                 380

Ser Val Ser Gly Ile Cys Phe Val Gly Tyr Lys Asn Tyr Arg Tyr Arg
        385                 390                 395                 400

Ala Gly Phe Val Leu Ala Pro Ile Gly Leu Val Leu Ile Val Gly Gly
                            405                 410                 415

Tyr Phe Leu Ile Arg Gly Val Met Thr Leu Phe Ser Ile Lys Ser Asn
                            420                 425                 430

His Pro Gly Leu Leu Ser Glu Lys Ala Ala Ser Lys Ile Asn Glu Thr
                    435                 440                 445

Met Leu Arg Leu Gly Ile Phe Gly Phe Leu Ala Phe Gly Phe Val Leu
        450                 455                 460

Ile Thr Phe Ser Cys His Phe Tyr Asp Phe Phe Asn Gln Ala Glu Trp
        465                 470                 475                 480

Glu Arg Ser Phe Arg Asp Tyr Val Leu Cys Gln Ala Asn Val Thr Ile
                    485                 490                 495
```

-continued

```
Gly Leu Pro Thr Lys Gln Pro Ile Pro Asp Cys Glu Ile Lys Asn Arg
            500             505             510

Pro Ser Leu Leu Val Glu Lys Ile Asn Leu Phe Ala Met Phe Gly Thr
            515             520             525

Gly Ile Ala Met Ser Thr Trp Val Trp Thr Lys Ala Thr Leu Leu Ile
            530             535             540

Trp Arg Arg Thr Trp Cys Arg Leu Thr Gly Gln Ser Asp Asp Glu Pro
545             550             555             560

Lys Arg Ile Lys Lys Ser Lys Met Ile Ala Lys Ala Phe Ser Lys Arg
            565             570             575

His Glu Leu Leu Gln Asn Pro Gly Gln Glu Leu Ser Phe Ser Met His
            580             585             590

Thr Val Ser His Asp Gly Pro Val Ala Gly Leu Ala Phe Asp Leu Asn
            595             600             605

Glu Pro Ser Ala Asp Val Ser Ser Ala Trp Ala Gln His Val Thr Lys
            610             615             620

Met Val Ala Arg Arg Gly Ala Ile Leu Pro Gln Asp Ile Ser Val Thr
625             630             635             640

Pro Val Ala Thr Pro Val Pro Pro Glu Glu Gln Ala Asn Leu Trp Leu
            645             650             655

Val Glu Ala Glu Ile Ser Pro Glu Leu Gln Lys Arg Leu Gly Arg Lys
            660             665             670

Lys Lys Arg Arg Lys Arg Lys Lys Glu Val Cys Pro Leu Ala Pro Pro
            675             680             685

Pro Glu Leu His Pro Pro Ala Pro Ala Pro Ser Thr Ile Pro Arg Leu
            690             695             700

Pro Gln Leu Pro Arg Gln Lys Cys Leu Val Ala Ala Gly Ala Trp Gly
705             710             715             720

Ala Gly Asp Ser Cys Arg Gln Gly Ala Trp Thr Leu Val Ser Asn Pro
            725             730             735

Phe Cys Pro Glu Pro Ser Pro Pro Gln Asp Pro Phe Leu Pro Ser Ala
            740             745             750

Pro Ala Pro Val Ala Trp Ala His Gly Arg Arg Gln Gly Leu Gly Pro
            755             760             765

Ile His Ser Arg Thr Asn Leu Met Asp Thr Glu Leu Met Asp Ala Asp
770             775             780

Ser Asp Phe
785
```